(12) United States Patent
Kim et al.

(10) Patent No.: US 10,686,142 B2
(45) Date of Patent: *Jun. 16, 2020

(54) CONDENSED CYCLIC COMPOUND AND ORGANIC LIGHT EMITTING DEVICE INCLUDING THE SAME

(71) Applicant: Samsung Electronics Co., Ltd., Suwon-si, Gyeonggi-do (KR)

(72) Inventors: Soyeon Kim, Anyang-si (KR); Sunyoung Lee, Seoul (KR); Yoonhyun Kwak, Seoul (KR); Sangyeob Lee, Hwaseong-si (KR); Kyuhyun Im, Yongin-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 321 days.

This patent is subject to a terminal disclaimer.

(21) Appl. No.: 14/692,991

(22) Filed: Apr. 22, 2015

(65) Prior Publication Data

US 2016/0118600 A1 Apr. 28, 2016

(30) Foreign Application Priority Data

Oct. 22, 2014 (KR) ........................ 10-2014-0143686

(51) Int. Cl.
| | | |
|---|---|---|
| H01L 51/00 | (2006.01) | |
| C07D 487/06 | (2006.01) | |
| C09K 11/06 | (2006.01) | |
| C07D 471/04 | (2006.01) | |
| C07D 495/04 | (2006.01) | |
| C07D 491/048 | (2006.01) | |
| H01L 51/50 | (2006.01) | |

(52) U.S. Cl.
CPC ........ H01L 51/0072 (2013.01); C07D 471/04 (2013.01); C07D 487/06 (2013.01); C07D 491/048 (2013.01); C07D 495/04 (2013.01); C09K 11/06 (2013.01); H01L 51/0052 (2013.01); H01L 51/0071 (2013.01); C09K 2211/1007 (2013.01); C09K 2211/1029 (2013.01); C09K 2211/1033 (2013.01); C09K 2211/1037 (2013.01); C09K 2211/1044 (2013.01); C09K 2211/1048 (2013.01); C09K 2211/1051 (2013.01); H01L 51/0085 (2013.01); H01L 51/0087 (2013.01); H01L 51/5016 (2013.01)

(58) Field of Classification Search
CPC .................................................. H01L 51/0072
See application file for complete search history.

(56) References Cited

U.S. PATENT DOCUMENTS

| | | | | |
|---|---|---|---|---|
| 5,059,863 | A | * | 10/1991 | Tashiro ................. C09K 11/06 252/301.26 |
| 5,645,948 | A | | 7/1997 | Shi et al. |
| 5,972,247 | A | | 10/1999 | Shi et al. |
| 6,465,115 | B2 | | 10/2002 | Shi et al. |
| 6,596,415 | B2 | | 7/2003 | Shi et al. |
| 7,737,627 | B2 | | 6/2010 | Hwang et al. |
| 7,833,634 | B2 | * | 11/2010 | Suzuki ................. C07D 471/04 257/E51.05 |
| 9,771,373 | B2 | * | 9/2017 | Lee ....................... C07D 487/06 |
| 10,593,890 | B2 | * | 3/2020 | Zeng ................... H01L 51/0072 |
| 2012/0075273 | A1 | * | 3/2012 | Abe ..................... C07D 487/06 345/205 |
| 2013/0320839 | A1 | | 12/2013 | Watanabe et al. |
| 2015/0333273 | A1 | * | 11/2015 | Lee ..................... H01L 51/0072 257/40 |

FOREIGN PATENT DOCUMENTS

| | | |
|---|---|---|
| JP | 812600 | 1/1996 |
| JP | 20003782 | 1/2000 |
| JP | 201272099 | 4/2012 |
| JP | 2012191031 | * 10/2012 |
| KR | 100573137 | 4/2006 |
| KR | 1020120087935 | 8/2012 |
| KR | 1020130130635 | 12/2013 |

OTHER PUBLICATIONS

C.W. Tang, et al., "Organic electroluminescent diodes", Appl. Phys. Lett. 51 (12). Sep. 21, 1987, pp. 913-915.
Chihaya Adachi, et al., "Confinement of charge carriers and molecular excitons within 5-nm-thick emitter layer in organic electroluminescent devices with a double heterostructure", Appl. Phys. Lett. 57 (6) Aug. 1990, pp. 531-533.
Shigehiro Yamaguchi, et al., "Diphenylamino-Substituted 2,5-Diarylsiloles for Single-Layer Organic Electroluminescent Devices", Chemistry Letters Nov. 10, 2000, pp. 98-101.
Youichi Sakamoto et al. "Synthesis, Characterization, and Electron-Transport Property of Perfluorinated Phenylene Dendrimers", J. Am. Chem. Soc. 2000, 122, 1832-1833.

* cited by examiner

Primary Examiner — Irina Krylova
(74) Attorney, Agent, or Firm — Cantor Colburn LLP

(57) ABSTRACT

A condensed cyclic compound represented by Formula 1:

Formula 1

(Continued)

wherein in Formula 1, groups and variables are the same as defined in the specification.

9 Claims, 1 Drawing Sheet

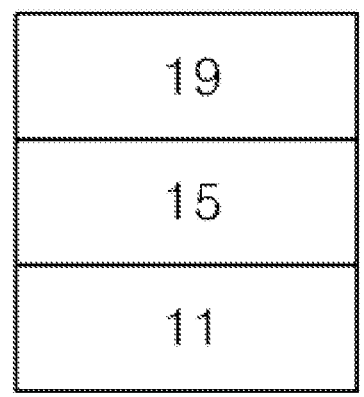

CONDENSED CYCLIC COMPOUND AND ORGANIC LIGHT EMITTING DEVICE INCLUDING THE SAME

CROSS-REFERENCE TO RELATED APPLICATION

This application claims priority to Korean Patent Application No. 10-2014-0143686, filed on Oct. 22, 2014, in the Korean Intellectual Property Office, and all the benefits accruing therefrom under 35 U.S.C. § 119, the content of which is incorporated herein in its entirety by reference.

BACKGROUND

1. Field

The present disclosure relates to a condensed cyclic compound and an organic light-emitting device including the same.

2. Description of the Related Art

Organic light emitting devices (OLEDs) are self-emission devices that have wide viewing angles, high contrast ratios, and short response times. In addition, the OLEDs exhibit excellent luminance, driving voltage, and response speed characteristics, and produce full-color images.

A typical organic light-emitting device includes an anode, a cathode, and an organic layer that is disposed between the anode and the cathode and includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. The holes and the electrons are recombined in the emission layer to produce excitons. These excitons change from an excited state to a ground state, thereby generating light.

Various types of organic light emitting devices are known. However, there still remains a need in OLEDs having low driving voltage, high efficiency, high brightness, and long lifespan.

SUMMARY

Provided are a condensed cyclic compound and an organic light-emitting device including the same.

Additional aspects will be set forth in part in the description which follows and, in part, will be apparent from the description, or may be learned by practice of the presented exemplary embodiments.

According to an exemplary embodiment, a condensed cyclic compound represented by Formula 1 is provided:

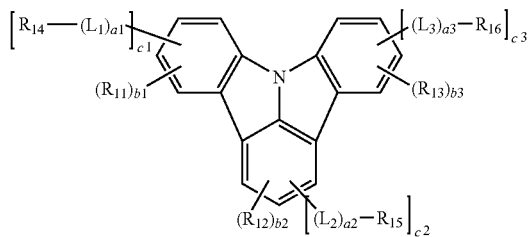

Formula 1

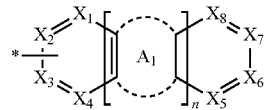

Formula 2 wherein in Formulae 1 and 2, ring $A_1$ is selected from a substituted or unsubstituted 5-membered carbocyclic group, a substituted or unsubstituted 6-membered carbocyclic group, a substituted or unsubstituted 5-membered heterocyclic group, and a substituted or unsubstituted 6-membered heterocyclic group, wherein the substituted or unsubstituted 5-membered heterocyclic group and the substituted or unsubstituted 6-membered heterocyclic group includes a heteroatom selected from the group consisting of O, S, and $N(R_9)$, n is an integer selected from 0 to 5, provided that when n is 2 or more, ring $A_1$ are identical to or different from each other, $X_1$ is N, $C(R_1)$, or C,
$X_2$ is N, $C(R_2)$, or C,
$X_3$ is N, $C(R_3)$, or C,
$X_4$ is N, $C(R_4)$, or C,
$X_5$ is N or $C(R_5)$,
$X_6$ is N or $C(R_6)$,
$X_7$ is N or $C(R_7)$,
$X_8$ is N or $C(R_8)$,
provided that
when $X_1$ is C, $X_1$ is linked to $(L_1)_{a1}$, $(L_2)_{a2}$, or $(L_3)_{a3}$,
when $X_2$ is C, $X_2$ is linked to $(L_1)_{a1}$, $(L_2)_{a2}$, or $(L_3)_{a3}$,
when $X_3$ is C, $X_3$ is linked to $(L_1)_{a1}$, $(L_2)_{a2}$, or $(L_3)_{a3}$,
when $X_4$ is C, $X_4$ is linked to $(L_1)_{a1}$, $(L_2)_{a2}$, or $(L_3)_{a3}$,
at least one selected from $X_1$ to $X_4$ is C, and
at least one selected from $X_1$ to $X_8$ is N, $L_1$ to $L_3$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{14}$ arylene group, a substituted or unsubstituted $C_1$-$C_{13}$ heteroarylene group, a substituted or unsubstituted divalent non-aromatic condensed polycyclic group, and a substituted or unsubstituted divalent non-aromatic condensed heteropolycyclic group, a1 to a3 are each independently 0, 1, or 2, $R_1$ to $R_9$ and $R_{11}$ to $R_{13}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{14}$ aryl group, a substituted or unsubstituted $C_6$-$C_{14}$ aryloxy group, a substituted or unsubstituted $C_6$-$C_{14}$ arylthio group, a substituted or unsubstituted $C_1$-$C_{13}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$), wherein $R_{14}$ to $R_{16}$ are each independently a group represented by Formula 2, b1, b3, c1, and c3 are each independently an integer selected from 1 to 4, b2 and c2 are each independently an integer selected from 0 to 3, and c1+c2+c3≥1, at least one of substituents of the substituted 5-membered carbocyclic group, substituted 6-membered carbocyclic group, substituted 5-membered heterocyclic group, substituted 6-membered heterocyclic group, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{14}$ arylene group, substituted $C_1$-$C_{13}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{14}$ aryl group, substituted $C_6$-$C_{14}$ aryloxy group, substituted $C_6$-$C_{14}$ arylthio group, substituted $C_1$-$C_{13}$ heteroaryl group, substituted monovalent non-aromatic condensed polycyclic group, and substituted monovalent non-aromatic condensed heteropolycyclic group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_6$-$C_{14}$ aryloxy group, a $C_6$-$C_{14}$ arylthio group, a $C_1$-$C_{13}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{14}$ alkyl group, a $C_2$-$C_{14}$ alkenyl group, a $C_2$-$C_{14}$ alkynyl group, a $C_1$-$C_{13}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_6$-$C_{14}$ aryloxy group, a $C_6$-$C_{14}$ arylthio group, a $C_1$-$C_{13}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$); and —N($Q_{21}$)($Q_{22}$), —Si($Q_{23}$)($Q_{24}$)($Q_{25}$), and —B($Q_{26}$)($Q_{27}$);

wherein $Q_1$ to $Q_7$, $Q_{11}$ to $Q_{17}$, and $Q_{21}$ to $Q_{27}$ are each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{13}$ heteroaryl group, a monovalent non-aromatic condensed polycyclic group, and a monovalent non-aromatic condensed heteropolycyclic group, wherein the number of rings that are condensed with each other in the divalent non-aromatic condensed polycyclic group, divalent non-aromatic condensed heteropolycyclic group, monovalent non-aromatic condensed polycyclic group, and monovalent non-aromatic condensed heteropolycyclic group is 2 or 3.

According to another exemplary embodiment, an organic light-emitting device includes:

a first electrode;

a second electrode; and an organic layer disposed between the first electrode and the second electrode, wherein the organic layer includes an emission layer and at least one condensed cyclic compound represented by Formula 1.

BRIEF DESCRIPTION OF THE DRAWINGS

These and/or other aspects will become apparent and more readily appreciated from the following description of the exemplary embodiments, taken in conjunction with the accompanying drawings in which:

FIG. 1 is a schematic cross-sectional view of an organic light-emitting device according to an embodiment.

DETAILED DESCRIPTION

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the FIGURES, to explain aspects. As used herein, the term "and/or" includes any and all combinations of one or more of the associated listed items.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Spatially relative terms, such as "beneath," "below," "lower," "above," "upper" and the like, may be used herein for ease of description to describe one element or feature's relationship to another element(s) or feature(s) as illustrated in the FIGURES. It will be understood that the spatially relative terms are intended to encompass different orientations of the device in use or operation in addition to the orientation depicted in the FIGURES. For example, if the device in the FIGURES is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

A condensed cyclic compound may be represented by Formula 1:

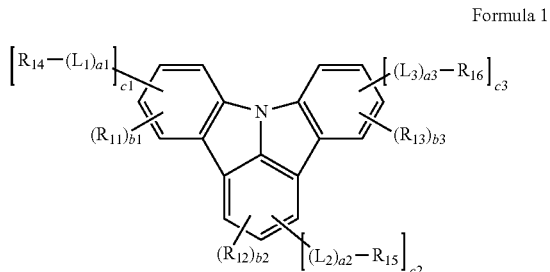

Formula 1

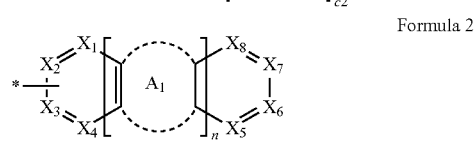

Formula 2 wherein $R_{14}$ to $R_{16}$ in Formula 1 may be each independently a group represented by Formula 2. Formula 2 may be understood by referring to the descriptions below.

In Formula 2, ring $A_1$ may be selected from a substituted or unsubstituted 5-membered carbocyclic group, a substituted or unsubstituted 6-membered carbocyclic group, a substituted or unsubstituted 5-membered heterocyclic group, and a substituted or unsubstituted 6-membered heterocyclic group, wherein the substituted or unsubstituted 5-membered heterocyclic group and the substituted or unsubstituted 6-membered heterocyclic group may be selected from the group consisting of O, S, and $N(R_9)$.

In some embodiments, ring $A_1$ in Formula 2 may be selected from
a 5-membered carbocyclic group, a 6-membered carbocyclic group, a 5-membered heterocyclic group, and a 6-membered heterocyclic group; and
a 5-membered carbocyclic group, a 6-membered carbocyclic group, a 5-membered heterocyclic group, and a 6-membered heterocyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a pyridinyl group, a pyrimidinyl group, a pyrazinyl group, and a triazinyl group.

n in Formula 2 may be an integer selected from 0 to 5, and when n is 2 or more, rings $A_1$ may be identical or different. In some embodiments, n in Formula 2 may be 0 or 1.

Ring $A_1$ may be a ring condensed with two 6-membered rings respectively positioned on both sides of ring $A_1$ by sharing a carbon atom.

When n in Formula 2 is 0, ring $A_1$ is not present, therefore, the two 6-membered rings may be condensed with each other.

In Formula 2, $X_1$ may be N, $C(R_1)$, or C, $X_2$ may be N, $C(R_2)$, or C, $X_3$ may be N, $C(R_3)$, or C, $X_4$ may be N, $C(R_4)$, or C, $X_5$ may be N or $C(R_5)$, $X_6$ may be N or $C(R_6)$, $X_7$ may be N or $C(R_7)$, and $X_8$ may be N or $C(R_8)$.

In Formula 2, when $X_1$ is C, $X_1$ may bind to $(L_1)_{a1}$, $(L_2)_{a2}$, or $(L_3)_{a3}$, when $X_2$ is C, $X_2$ may bind to $(L_1)_{a1}$, $(L_2)_{a2}$, or $(L_3)_{a3}$, when $X_3$ is C, $X_3$ may bind to $(L_1)_{a1}$, $(L_2)_{a2}$, or $(L_3)_{a3}$, when $X_4$ is C, $X_4$ may bind to $(L_1)_{a1}$, $(L_2)_{a2}$, or $(L_3)_{a3}$, and at least one selected from $X_1$ to $X_4$ may be C.

At least one selected from $X_1$ to $X_8$ in Formula 2 may be N.

In some embodiments, one, two, or three of $X_1$ to $X_8$ in Formula 2 may be N.

In some embodiments, one or two of $X_1$ to $X_8$ in Formula 2 may be N, but it is not limited thereto.

In Formula 1, $L_1$ to $L_3$ may be each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{14}$ arylene group, a substituted or unsubstituted $C_1$-$C_{13}$ heteroarylene group, a substituted or unsubstituted divalent non-aromatic condensed polycyclic group, and a substituted or unsubstituted divalent non-aromatic condensed heteropolycyclic group.

In some embodiments, $L_1$ to $L_3$ in Formula 1 may be each independently selected from a cyclopentylene group, a cyclohexylene group, a cyclopentenylene group, a cyclohexenylene group, a cycloheptenylene group, a phenylene group, a naphthylene group, a fluorenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a quinoxalinylene group, a quinazolinylene group, a carbazolylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, an imidazopyrimidinylene group, and an imidazopyridinylene group; and a cyclopentylene group, a cyclohexylene group, a cyclopentenylene group, a cyclohexenylene group, a cycloheptenylene group, a phenylene group, a naphthylene group, a fluorenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a quinoxalinylene group, a quinazolinylene group, a carbazolylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, an imidazopyrimidinylene group, and an imidazopyridinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cyclopentenyl group, a cyclohexenyl group, a cycloheptenyl group, a phenyl group, a naphthyl group, a fluorenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a quinoxalinyl group, a quinazolinyl group, a carbazolyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyrimidinyl group, an imidazopyridinyl group, and —Si($Q_{23}$)($Q_{24}$)($Q_{25}$);

wherein $Q_{23}$ to $Q_{25}$ may be each independently selected from a hydrogen, a $C_1$-$C_{20}$ alkyl group, a $C_1$-$C_{20}$ alkoxy group, a phenyl group, a naphthyl group, a pyridinyl group, a pyrimidinyl group, and a triazinyl group.

In some embodiments, $L_1$ to $L_3$ in Formula 1 may be each independently selected from a phenylene group, a naphthylene group, a fluorenylene group, a pyridinylene group, a pyrazinylene group, a pyrimidinylene group, a pyridazinylene group, a quinolinylene group, an isoquinolinylene group, a quinoxalinylene group, a quinazolinylene group, a furanylene group, a benzofuranylene group, a thiophenylene group, a benzothiophenylene group, a thiazolylene group, an isothiazolylene group, an isoxazolylene group, an oxazolylene group, an oxadiazolylene group, a triazinylene group, a dibenzofuranylene group, and a dibenzothiophenylene group; and a phenylene group, a naphthylene group, a fluorenylene group, a pyridinylene group, a pyrazinylene group, a pyrimidinylene group, a pyridazinylene group, a quinolinylene group, an isoquinolinylene group, a quinoxalinylene group, a quinazolinylene group, a furanylene group, a benzofuranylene group, a thiophenylene group, a benzothiophenylene group, a thiazolylene group, an isothiazolylene group, an isoxazolylene group, an oxazolylene group, an oxadiazolylene group, a triazinylene group, a dibenzofuranylene group, and a dibenzothiophenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a triazinyl group, and —Si($Q_{23}$)($Q_{24}$)($Q_{25}$);

wherein $Q_{23}$ to $Q_{25}$ may be each independently selected from a hydrogen, a $C_1$-$C_{10}$ alkyl group, a $C_1$-$C_{10}$ alkoxy group, a phenyl group, a naphthyl group, a pyridinyl group, a pyrimidinyl group, and a triazinyl group.

In some embodiments, $L_1$ to $L_3$ in Formula 1 may be each independently selected from a phenylene group, a naphthylene group, a fluorenylene group, a pyridinylene group, a pyrazinylene group, a pyrimidinylene group, a pyridazinylene group, a triazinylene group, a dibenzofuranylene group, and a dibenzothiophenylene group; and a phenylene group, a naphthylene group, a fluorenylene group, a pyridinylene group, a pyrazinylene group, a pyrimidinylene group, a pyridazinylene group, a triazinylene group, a dibenzofuranylene group, and a dibenzothiophenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a triazinyl group, and —Si($Q_{23}$)($Q_{24}$)($Q_{25}$);

wherein $Q_{23}$ to $Q_{25}$ may be each independently selected from a hydrogen, a $C_1$-$C_{10}$ alkyl group, a $C_1$-$C_{10}$ alkoxy group, a phenyl group, a naphthyl group, a pyridinyl group, a pyrimidinyl group, and a triazinyl group, but they are not limited thereto.

In some embodiments, $L_1$ to $L_3$ in Formula 1 may be each independently a group represented by one of Formulae 5-1 to 5-9, but they are not limited thereto:

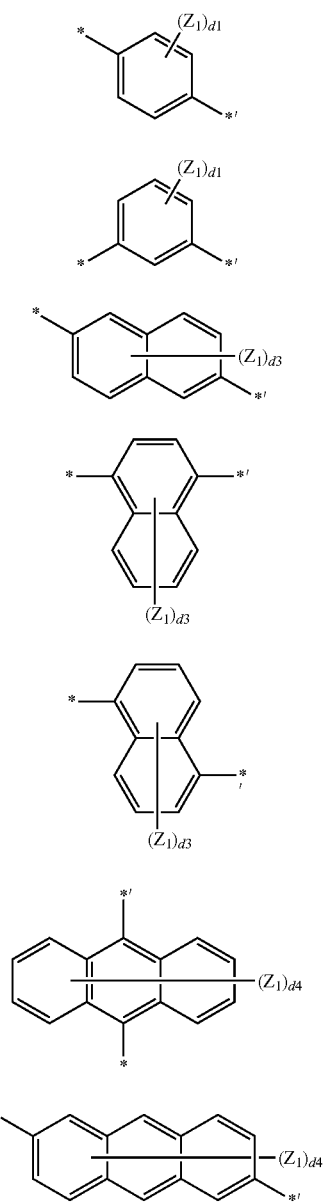

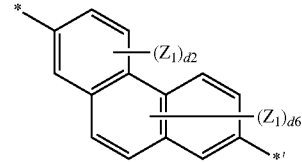

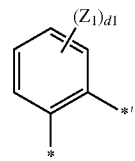

wherein in Formulae 5-1 to 5-9, $Z_1$ and $Z_2$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a triazinyl group, and —Si($Q_{23}$)($Q_{24}$)($Q_{25}$);

wherein $Q_{23}$ to $Q_{25}$ may be each independently selected from a hydrogen, a $C_1$-$C_{10}$ alkyl group, a $C_1$-$C_{10}$ alkoxy group, a phenyl group, a naphthyl group, a pyridinyl group, a pyrimidinyl group, and a triazinyl group;

d1 may be an integer selected from 1 to 4, d2 may be an integer selected from 1 to 3, d3 may be an integer selected from 1 to 6, d4 may be an integer selected from 1 to 8, and d6 may be an integer of 1 to 5; and

* and *' each indicates a binding site to a neighboring atom.

a1 to a3 in Formula 1 may be each independently 0, 1, or 2. When a1 is 0, -($L_1$)$_{a1}$-*' in Formula 1 may be a single bond, when a2 is 0, *-($L_2$)$_{a2}$-*' in Formula 1 may be a single bond, and when a3 is 0, *-($L_3$)$_{a3}$-*' in Formula 1 may be a single bond. When a1 is 2 or more, groups $L_1$ may be identical to or different from each other, when a2 is 2 or more, groups $L_2$ may be identical to or different from each other, and when a3 is 2 or more, groups $L_3$ may be identical to or different from each other. In some embodiments, a1 to a3 in Formula 1 may be each independently 0 or 1.

In Formulae 1 and 2, $R_1$ to $R_9$ and $R_{11}$ to $R_{13}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{14}$ aryl group, a substituted or unsubstituted $C_6$-$C_{14}$ aryloxy group, a substituted or unsubstituted $C_6$-$C_{14}$ arylthio group, a substituted or unsubstituted $C_1$-$C_{13}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$).

In some embodiments, in Formulae 1 and 2, $R_1$ to $R_9$ and $R_{11}$ to $R_{13}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a cyclopentyl group, a cyclohexyl group, a cyclopentenyl group, a cyclohexenyl group, a cycloheptenyl group, a phenyl group, a naphthyl group, a fluorenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a quinoxalinyl group, a quinazolinyl group, a carbazolyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyrimidinyl group, and an imidazopyridinyl group;

a cyclopentyl group, a cyclohexyl group, a cyclopentenyl group, a cyclohexenyl group, a cycloheptenyl group, a phenyl group, a naphthyl group, a fluorenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a quinoxalinyl group, a quinazolinyl group, a carbazolyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyrimidinyl group, and an imidazopyridinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cyclopentenyl group, a cyclohexenyl group, a cycloheptenyl group, a phenyl group, a naphthyl group, a fluorenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a quinoxalinyl group, a quinazolinyl group, a carbazolyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyrimidinyl group, an imidazopyridinyl group, a biphenyl group, a terphenyl group, and —Si($Q_{23}$)($Q_{24}$)($Q_{25}$); and —Si($Q_3$)($Q_4$)($Q_5$);

wherein $Q_3$ to $Q_5$ and $Q_{23}$ to $Q_{25}$ may be each independently selected from a hydrogen, a $C_1$-$C_{20}$ alkyl group, a $C_1$-$C_{20}$ alkoxy group, a phenyl group, a naphthyl group, a pyridinyl group, a pyrimidinyl group, and a triazinyl group.

In some embodiments, in Formulae 1 and 2, $R_1$ to $R_8$ and $R_{11}$ to $R_{13}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group;

a $C_1$-$C_{10}$ alkyl group and a $C_1$-$C_{10}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, a fluorenyl group, a pyridinyl group, a pyrazinyl group, a pyrimidinyl group, a pyridazinyl group, a quinolinyl group, an isoquinolinyl group, a quinoxalinyl group, a quinazolinyl group, a furanylene group, a benzofuranyl group, a thiophenyl group, a benzothiophenyl group, a thiazolyl group, an isothiazolyl group, an isoxazolyl group, an oxazolyl group, an oxadiazolyl group, a triazinyl group, a dibenzofuranyl group, and a dibenzothiophenyl group;

a phenyl group, a naphthyl group, a fluorenyl group, a pyridinyl group, a pyrazinyl group, a pyrimidinyl group, a pyridazinyl group, a quinolinyl group, an isoquinolinyl group, a quinoxalinyl group, a quinazolinyl group, a furanylene group, a benzofuranyl group, a thiophenyl group, a benzothiophenyl group, a thiazolyl group, an isothiazolyl group, an isoxazolyl group, an oxazolyl group, an oxadiazolyl group, a triazinyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a triazinyl group, a biphenyl group, a terphenyl group, and —Si($Q_{23}$)($Q_{24}$)($Q_{25}$); and —Si($Q_3$)($Q_4$)($Q_5$);

wherein $R_9$ may be selected from a phenyl group, a naphthyl group, a fluorenyl group, a pyridinyl group, a pyrazinyl group, a pyrimidinyl group, a pyridazinyl group, a quinolinyl group, an isoquinolinyl group, a quinoxalinyl group, a quinazolinyl group, a furanylene group, a benzofuranyl group, a thiophenyl group, a benzothiophenyl group, a thiazolyl group, an isothiazolyl group, an isoxazolyl group, an oxazolyl group, an oxadiazolyl group, a triazinyl group, a dibenzofuranyl group, and a dibenzothiophenyl group; and a phenyl group, a naphthyl group, a fluorenyl group, a pyridinyl group, a pyrazinyl group, a pyrimidinyl group, a pyridazinyl group, a quinolinyl group, an isoquinolinyl group, a quinoxalinyl group, a quinazolinyl group, a furanylene group, a benzofuranyl group, a thiophenyl group, a benzothiophenyl group, a thiazolyl group, an isothiazolyl group, an isoxazolyl group, an oxazolyl group, an oxadiazolyl group, a triazinyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a triazinyl group, a biphenyl group, a terphenyl group, and —Si($Q_{23}$)($Q_{24}$)($Q_{25}$);

wherein $Q_3$ to $Q_5$ and $Q_{23}$ to $Q_{25}$ may be each independently selected from a hydrogen, a $C_1$-$C_{10}$ alkyl group, a $C_1$-$C_{10}$ alkoxy group, a phenyl group, a naphthyl group, a pyridinyl group, a pyrimidinyl group, and a triazinyl group.

In some embodiments, in Formulae 1 and 2, $R_1$ to $R_8$ and $R_{11}$ to $R_{13}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group;

a $C_1$-$C_{10}$ alkyl group and a $C_1$-$C_{10}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, a fluorenyl group, a pyridinyl group, a pyrazinyl group, a pyrimidinyl group, a pyridazinyl group, a triazinyl group, a dibenzofuranyl group, and a dibenzothiophenyl group;

a phenyl group, a naphthyl group, a fluorenyl group, a pyridinyl group, a pyrazinyl group, a pyrimidinyl group, a pyridazinyl group, a triazinyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a triazinyl group, a biphenyl group, a terphenyl group, and —Si($Q_{23}$)($Q_{24}$)($Q_{25}$); and —Si($Q_3$)($Q_4$)($Q_5$);

wherein $R_9$ may be selected from a phenyl group, a naphthyl group, a fluorenyl group, a pyridinyl group, a pyrazinyl group, a pyrimidinyl group, a pyridazinyl group, a triazinyl group, a dibenzofuranyl group, and a dibenzothiophenyl group; and a phenyl group, a naphthyl group, a fluorenyl group, a pyridinyl group, a pyrazinyl group, a pyrimidinyl group, a pyridazinyl group, a triazinyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a triazinyl group, a biphenyl group, a terphenyl group, and —Si($Q_{23}$)($Q_{24}$)($Q_{25}$);

wherein $Q_3$ to $Q_5$ and $Q_{23}$ to $Q_{25}$ may be each independently selected from a hydrogen, a $C_1$-$C_{10}$ alkyl group, a $C_1$-$C_{10}$ alkoxy group, a phenyl group, a naphthyl group, a pyridinyl group, a pyrimidinyl group, and a triazinyl group, but they are not limited thereto.

$R_{14}$ to $R_{16}$ in Formula 1 may be each independently a group represented by Formula 2.

In some embodiments, $R_{14}$ to $R_{16}$ in Formula 1 may be each independently selected from a group represented by one of Formulae 2-1 to 2-108:

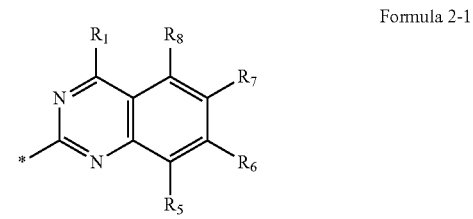

Formula 2-1

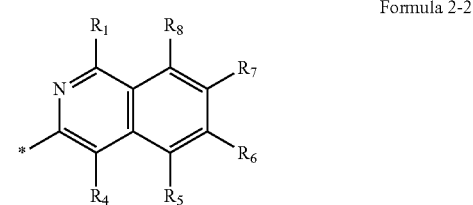

Formula 2-2

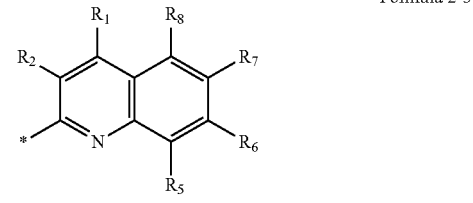

Formula 2-3

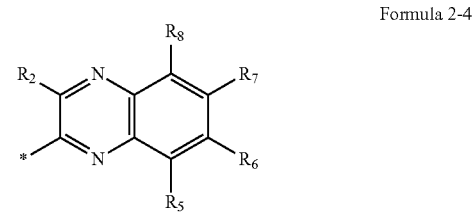

Formula 2-4

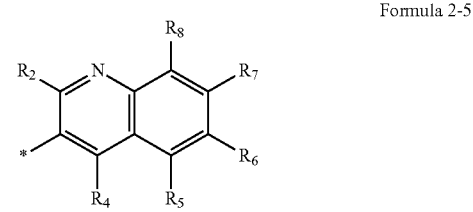

Formula 2-5

Formula 2-6
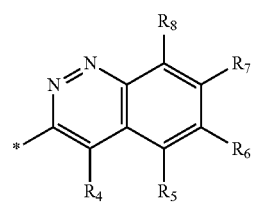
Formula 2-7
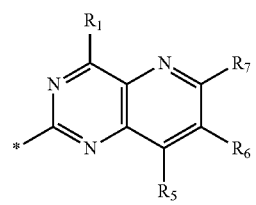
Formula 2-8
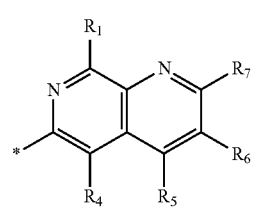
Formula 2-9
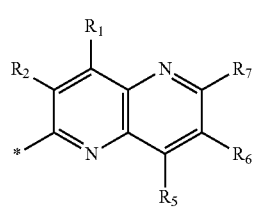
Formula 2-10
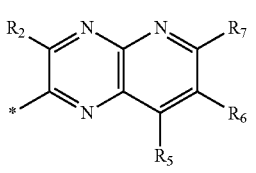
Formula 2-11
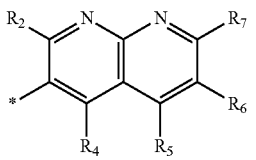
Formula 2-12
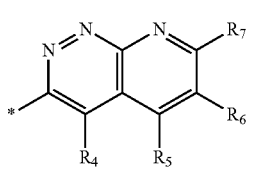
Formula 2-13
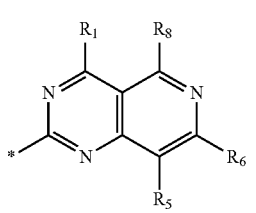
Formula 2-14
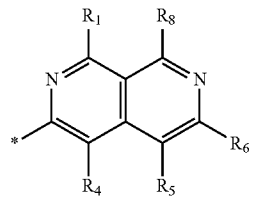
Formula 2-15
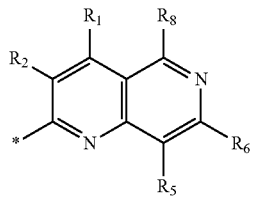
Formula 2-16
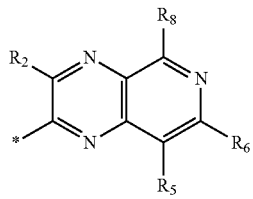
Formula 2-17
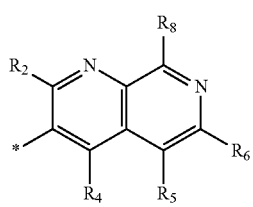
Formula 2-18
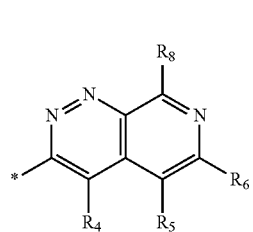
Formula 2-19
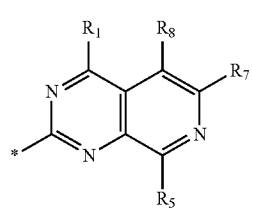
Formula 2-20
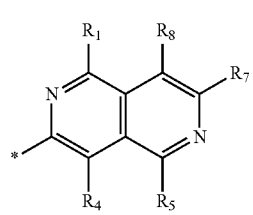

Formula 2-21
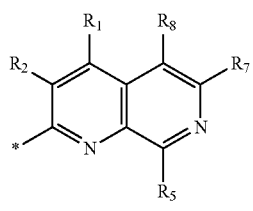
Formula 2-22
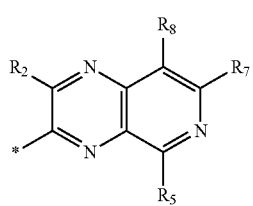
Formula 2-23
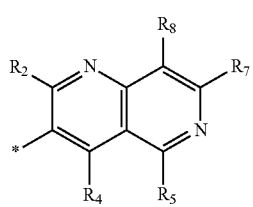
Formula 2-24
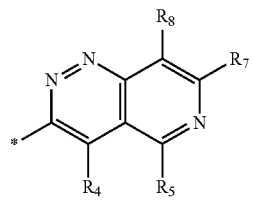
Formula 2-25
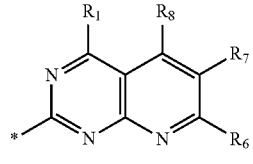
Formula 2-26
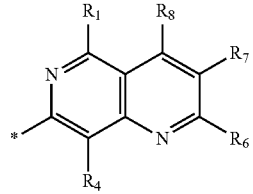
Formula 2-27
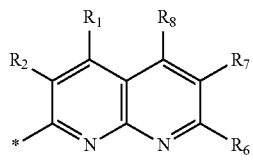
Formula 2-28
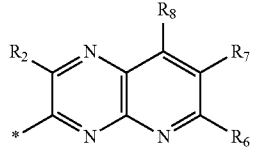
Formula 2-29
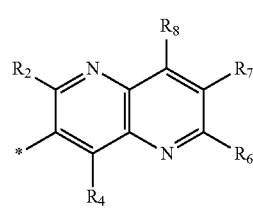
Formula 2-30
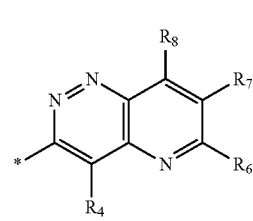
Formula 2-31
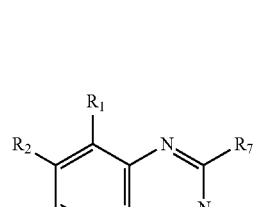
Formula 2-32
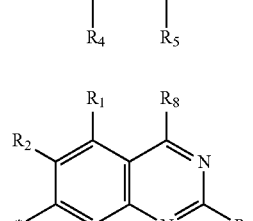
Formula 2-33
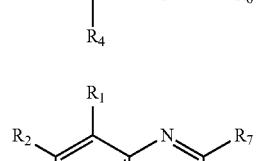
Formula 2-34
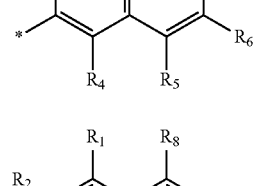
Formula 2-35
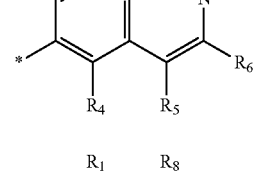
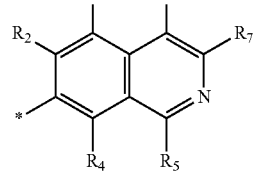

-continued
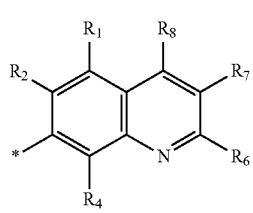
Formula 2-36
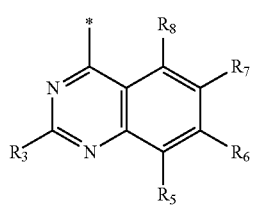
Formula 2-37
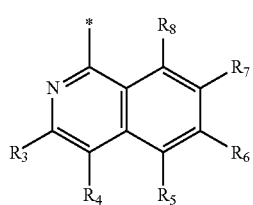
Formula 2-38
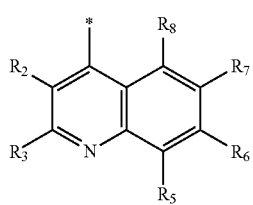
Formula 2-39
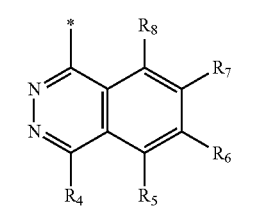
Formula 2-40
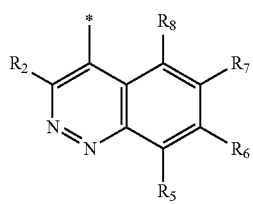
Formula 2-41
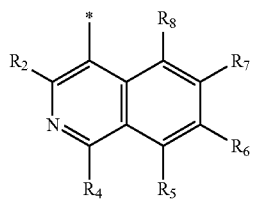
Formula 2-42
-continued
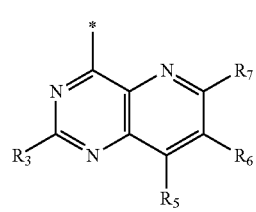
Formula 2-43
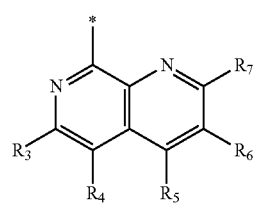
Formula 2-44
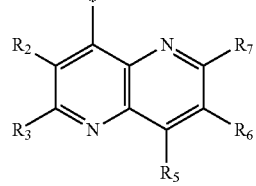
Formula 2-45
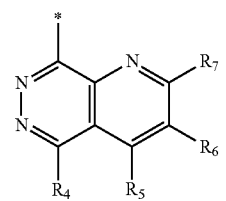
Formula 2-46
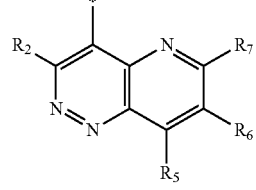
Formula 2-47
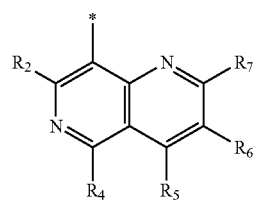
Formula 2-48
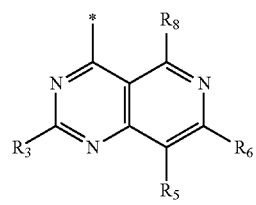
Formula 2-49

-continued
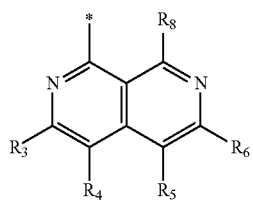
Formula 2-50
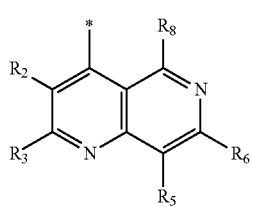
Formula 2-51
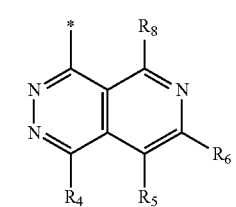
Formula 2-52
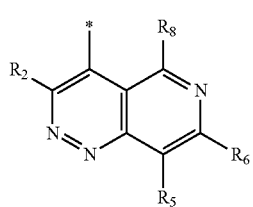
Formula 2-53
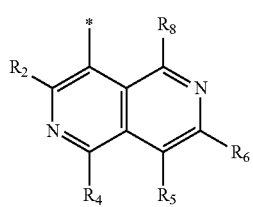
Formula 2-54
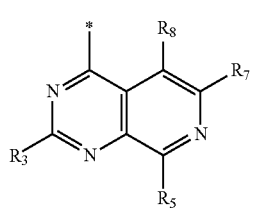
Formula 2-55
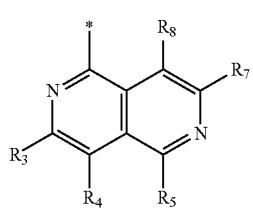
Formula 2-56
-continued
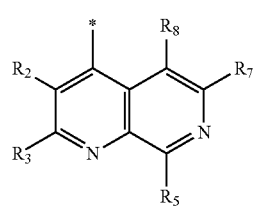
Formula 2-57
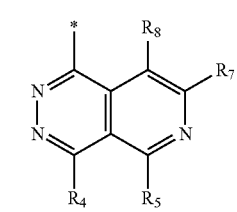
Formula 2-58
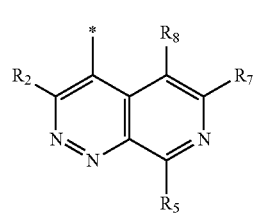
Formula 2-59
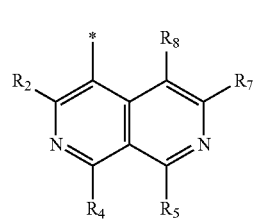
Formula 2-60
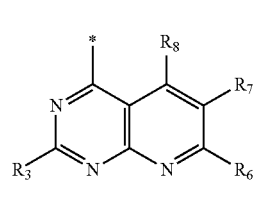
Formula 2-61
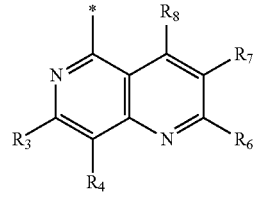
Formula 2-62
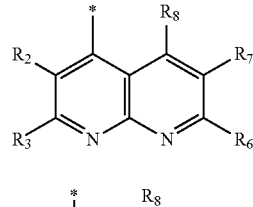
Formula 2-63
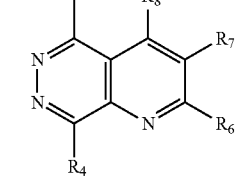
Formula 2-64

Formula 2-65
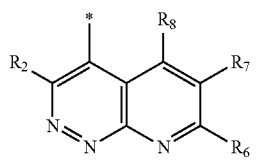
Formula 2-66
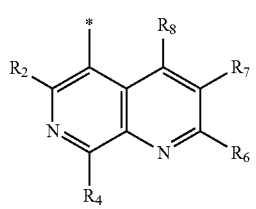
Formula 2-67
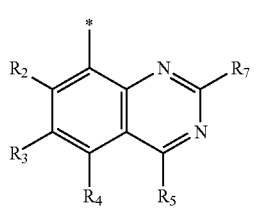
Formula 2-68
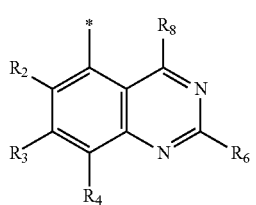
Formula 2-69
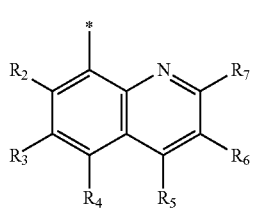
Formula 2-70
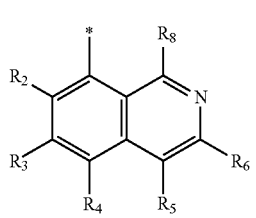
Formula 2-71
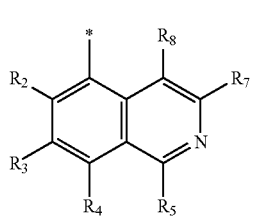
Formula 2-72
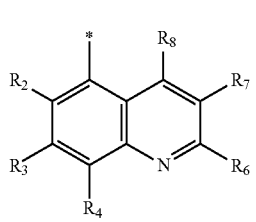
Formula 2-73
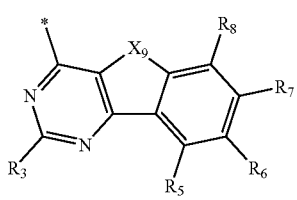
Formula 2-74
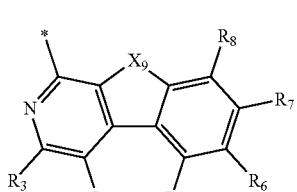
Formula 2-75
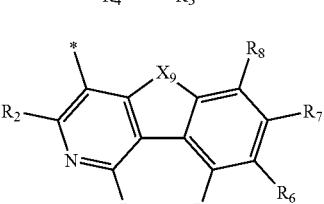
Formula 2-76
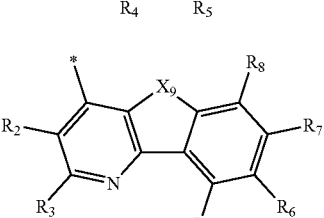
Formula 2-77
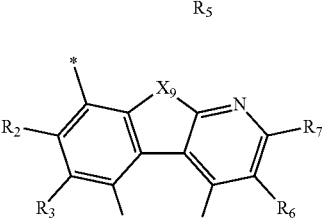
Formula 2-78
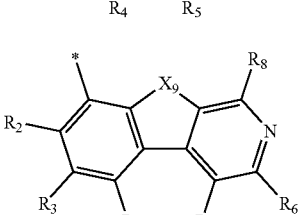
Formula 2-79
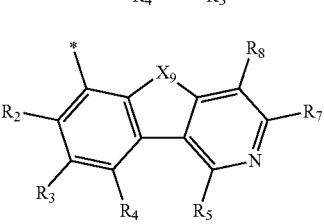
Formula 2-80
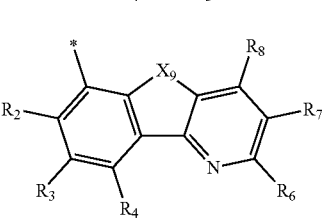

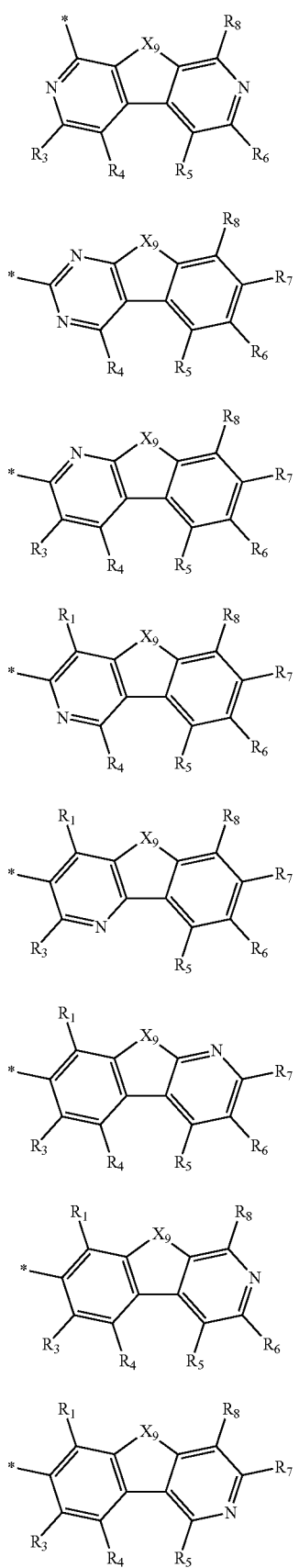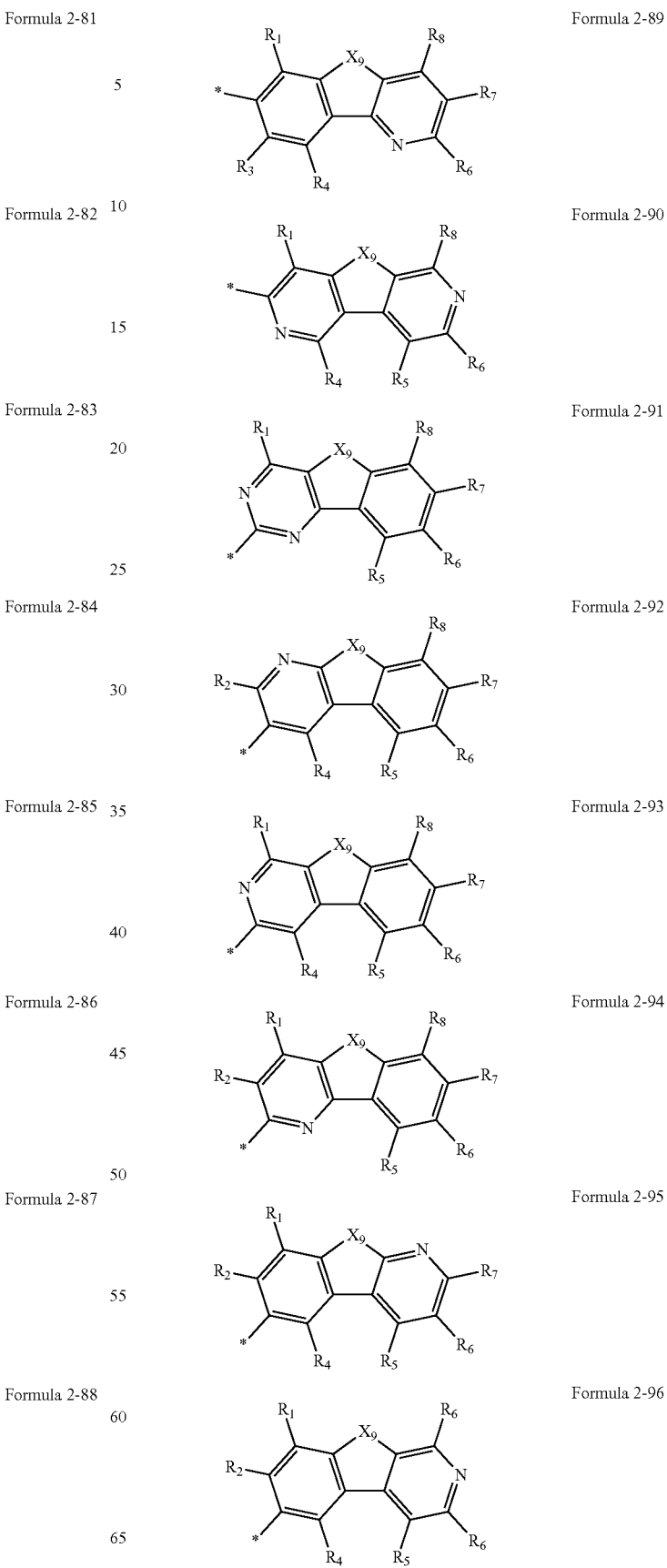

-continued

Formula 2-97
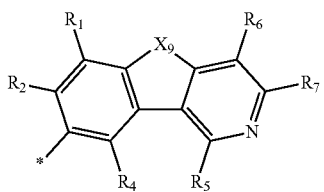

Formula 2-98
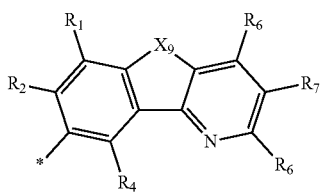

Formula 2-99
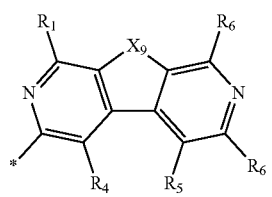

Formula 2-100
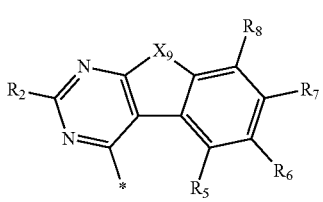

Formula 2-101
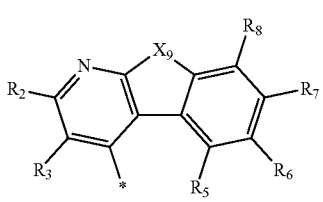

Formula 2-102
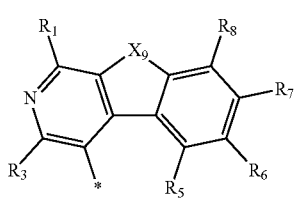

Formula 2-103
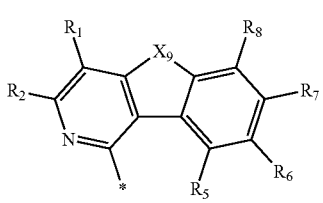

Formula 2-104
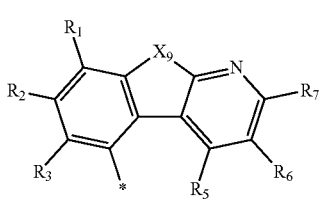

-continued

Formula 2-105
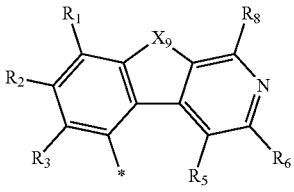

Formula 2-106
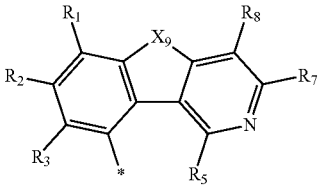

Formula 2-107
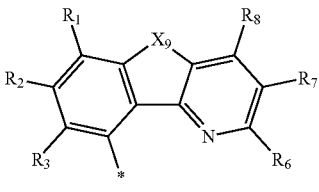

Formula 2-108
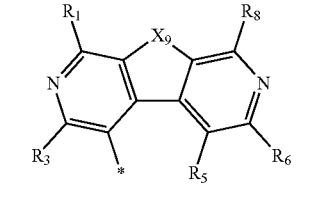

wherein in Formulae 2-1 to 2-108, $X_9$ may be O, S, or $N(R_9)$, and the descriptions for $R_1$ to $R_9$ may be the same as described in the specification.

In some embodiments, in Formulae 2-1 to 2-108, $R_1$ to $R_8$ may be each independently a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a cyclopentyl group, a cyclohexyl group, a cyclopentenyl group, a cyclohexenyl group, a cycloheptenyl group, a phenyl group, a naphthyl group, a fluorenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a quinoxalinyl group, a quinazolinyl group, a carbazolyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyrimidinyl group, and an imidazopyridinyl group;

a cyclopentyl group, a cyclohexyl group, a cyclopentenyl group, a cyclohexenyl group, a cycloheptenyl group, a phenyl group, a naphthyl group, a fluorenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a quinoxalinyl group, a quinazolinyl group, a carbazolyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyrimidinyl group, and an imidazopyridinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cyclopentenyl group, a cyclohexenyl group, a cycloheptenyl group, a phenyl group, a naphthyl group, a fluorenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a quinoxalinyl group, a quinazolinyl group, a carbazolyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyrimidinyl group, an imidazopyridinyl group, a biphenyl group, a terphenyl group, and —Si($Q_{23}$)($Q_{24}$)($Q_{25}$); and —Si($Q_3$)($Q_4$)($Q_5$);

wherein $R_9$ may be selected from a cyclopentyl group, a cyclohexyl group, a cyclopentenyl group, a cyclohexenyl group, a cycloheptenyl group, a phenyl group, a naphthyl group, a fluorenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a quinoxalinyl group, a quinazolinyl group, a carbazolyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyrimidinyl group, and an imidazopyridinyl group; and a cyclopentyl group, a cyclohexyl group, a cyclopentenyl group, a cyclohexenyl group, a cycloheptenyl group, a phenyl group, a naphthyl group, a fluorenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a quinoxalinyl group, a quinazolinyl group, a carbazolyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyrimidinyl group, and an imidazopyridinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cyclopentenyl group, a cyclohexenyl group, a cycloheptenyl group, a phenyl group, a naphthyl group, a fluorenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a quinoxalinyl group, a quinazolinyl group, a carbazolyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyrimidinyl group, an imidazopyridinyl group, a biphenyl group, and a terphenyl group;

wherein $Q_3$ to $Q_5$ and $Q_{23}$ to $Q_{25}$ may be each independently selected from a hydrogen, a $C_1$-$C_{20}$ alkyl group, a $C_1$-$C_{20}$ alkoxy group, a phenyl group, a naphthyl group, a pyridinyl group, a pyrimidinyl group, and a triazinyl group.

In some embodiments, $R_{14}$ to $R_{16}$ in Formula 1 may be each independently a group represented by one of Formulae 2-1, 2-6, 2-7, 2-19, 2-31, 2-36, 2-43, 2-45, 2-47, 2-48, 2-60, 2-63, 2-67, 2-72, 2-80, 2-89, 2-91, 2-93, 2-96, and 2-98, but they are not limited thereto.

In some embodiments, in Formulae 2-1 to 2-108, $R_1$ to $R_8$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group;

a $C_1$-$C_{10}$ alkyl group and a $C_1$-$C_{10}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, a pyridinyl group, a pyrazinyl group, a pyrimidinyl group, a pyridazinyl group, a triazinyl group, a dibenzofuranyl group, and a dibenzothiophenyl group;

a phenyl group, a naphthyl group, a pyridinyl group, a pyrazinyl group, a pyrimidinyl group, a pyridazinyl group, a triazinyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a triazinyl group, a biphenyl group, a terphenyl group, and —Si($Q_{23}$)($Q_{24}$)($Q_{25}$); and —Si($Q_3$)($Q_4$)($Q_5$);

wherein $R_9$ may be selected from a phenyl group, a naphthyl group, a pyridinyl group, a pyrazinyl group, a pyrimidinyl group, a pyridazinyl group, a triazinyl group, a dibenzofuranyl group, and a dibenzothiophenyl group; and a phenyl group, a naphthyl group, a pyridinyl group, a pyrazinyl group, a pyrimidinyl group, a pyridazinyl group, a triazinyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a triazinyl group, a biphenyl group, a terphenyl group, and —Si($Q_{23}$)($Q_{24}$)($Q_{25}$);

wherein $Q_3$ to $Q_5$ and $Q_{23}$ to $Q_{25}$ may be each independently selected from a hydrogen, a $C_1$-$C_{20}$ alkyl group, a $C_1$-$C_{20}$ alkoxy group, a phenyl group, a naphthyl group, a pyridinyl group, a pyrimidinyl group, and a triazinyl group, but they are not limited thereto.

In some embodiments, $R_{14}$ to $R_{16}$ in Formula 1 may be each independently a group represented by one of Formulae 3-1 to 3-41, but they are not limited thereto.

Formula 3-1

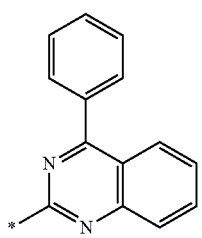

Formula 3-2

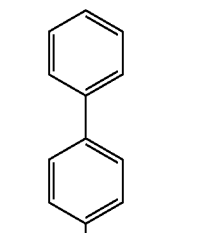

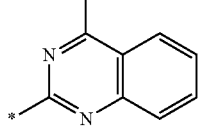

Formula 3-3

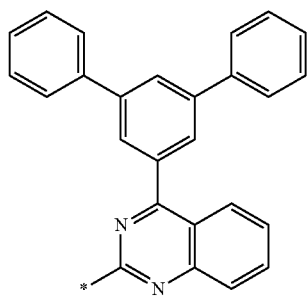

Formula 3-4

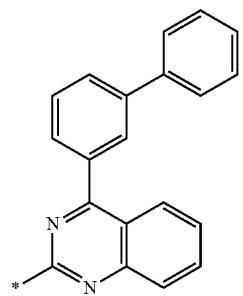

Formula 3-5

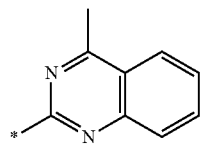

Formula 3-6

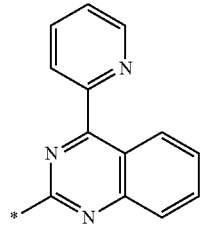

Formula 3-7

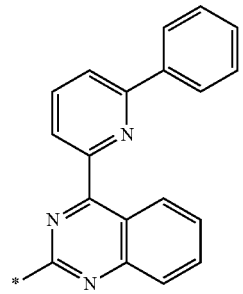

Formula 3-8

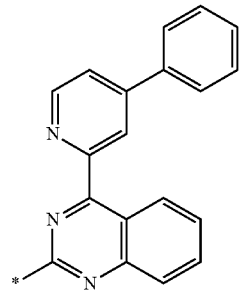

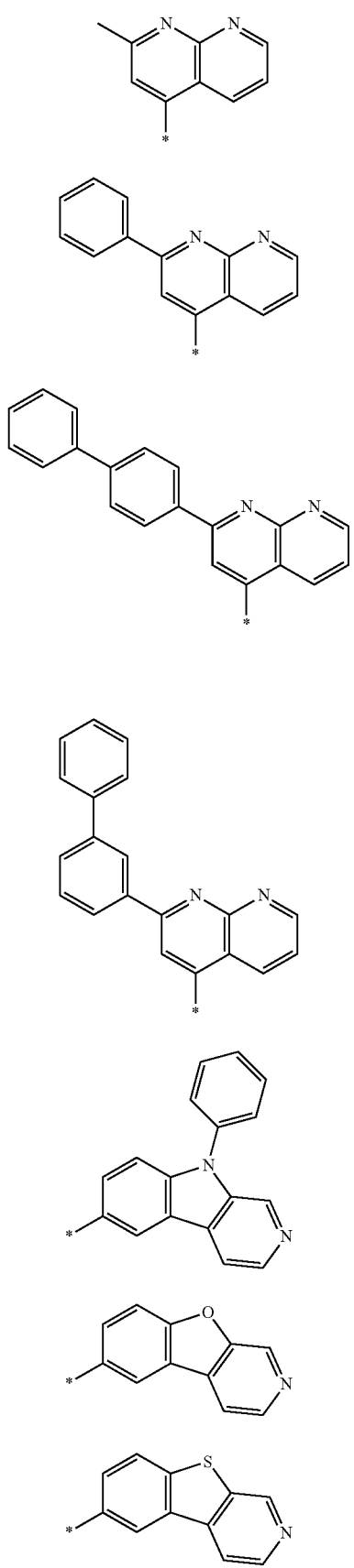
Formula 3-9
Formula 3-10
Formula 3-11
Formula 3-12
Formula 3-13
Formula 3-14
Formula 3-15
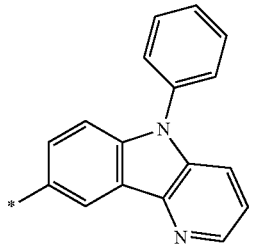
Formula 3-16
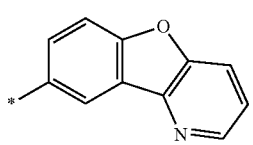
Formula 3-17
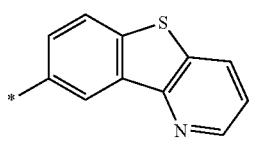
Formula 3-18
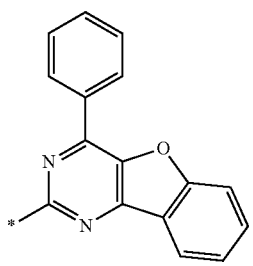
Formula 3-19
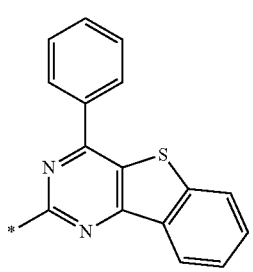
Formula 3-20
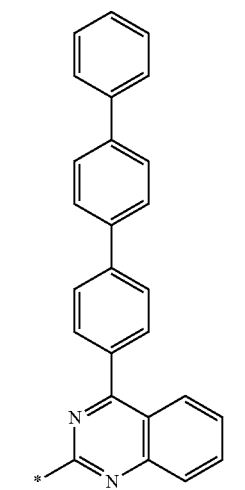
Formula 3-21

| | |
|---|---|
| 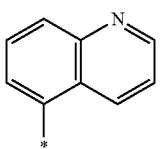 Formula 3-22 | 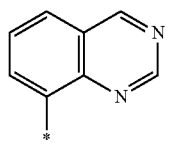 Formula 3-30 |
| 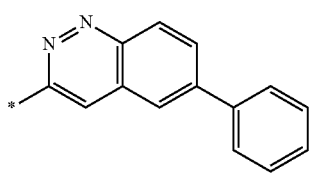 Formula 3-23 |  Formula 3-31 |
| 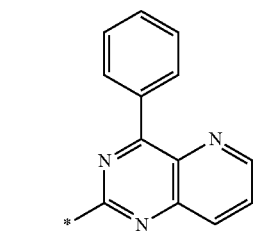 Formula 3-24 | 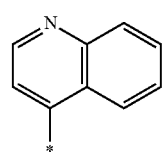 Formula 3-32 |
| | 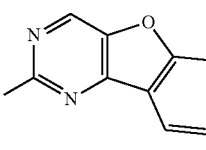 Formula 3-33 |
| 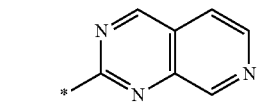 Formula 3-25 | |
| 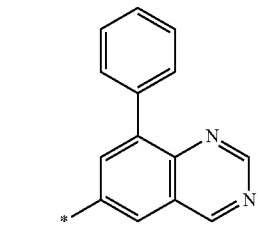 Formula 3-26 | 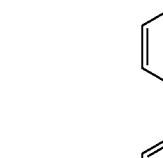 Formula 3-34 |
| | Formula 3-35 |
| 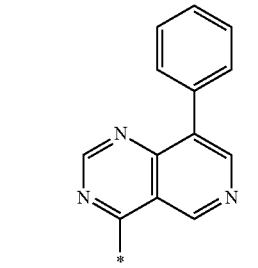 Formula 3-27 | Formula 3-36 |
| | 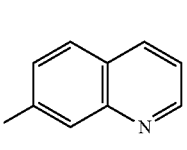 |
| 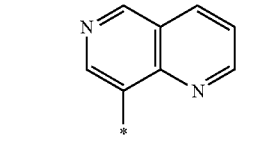 Formula 3-28 | Formula 3-37 |
| 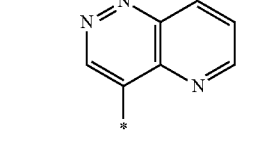 Formula 3-29 | 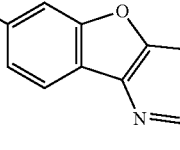 Formula 3-38 |

-continued

Formula 3-39

Formula 3-40

Formula 3-41

In Formula 1, b1, b3, c1, and c3 may be each independently an integer selected from 1 to 4, and b2 and c2 may be each independently an integer selected from 0 to 3.

b1 indicates the number of $R_{11}$, and when b1 is 2 or more, groups $R_{11}$ may be identical or different from each other. The descriptions for b2 and b3 may be understood by referring to the descriptions for b1 and a structure of Formula 1.

In some embodiments, b1 to b3 in Formula 1 may be each independently 1 or 2. In some embodiments, b1 to b3 in Formula 1 may be 1, but they are not limited thereto.

In Formula 1, c1+c2+c3≥1. In other words, at least one selected from $R_{14}$ to $R_{16}$ in Formula 1 is essentially present.

In some embodiments, c1 to c3 in Formula 1 may be each independently 0 or 1, and c1+c2+c3≥1.

In some embodiments, in Formula 1, c1 may be 0, c2 may be 1, and c3 may be 0;

c1 may be 0, c2 may be 0, and c3 may be 1;

c1 may be 1, c2 may be 1, and c3 may be 0; or c1 may be 1, c2 may be 0, and c3 may be 1, but they are not limited thereto.

In some embodiments, the condensed cyclic compound represented by Formula 1 may be represented by one of Formulae 1A to 1H:

Formula 1A

Formula 1B

Formula 1C

Formula 1D

Formula 1E

Formula 1F

Formula 1G

-continued

Formula 1H

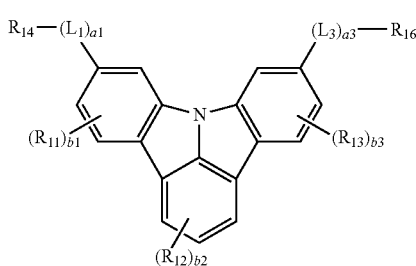

In Formulae 1A to 1H, the descriptions for $L_1$ to $L_3$, a1 to a3, $R_{11}$ to $R_{16}$, and b1 to b3 may be the same as defined herein.

In some embodiments, in Formulae 1A and 1H, $L_1$ to $L_3$ may be each independently selected from a phenylene group, a naphthylene group, a fluorenylene group, a pyridinylene group, a pyrazinylene group, a pyrimidinylene group, a pyridazinylene group, a triazinylene group, a dibenzofuranylene group, and a dibenzothiophenylene group; and a phenylene group, a naphthylene group, a fluorenylene group, a pyridinylene group, a pyrazinylene group, a pyrimidinylene group, a pyridazinylene group, a triazinylene group, a dibenzofuranylene group, and a dibenzothiophenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a triazinyl group, a biphenyl group, and a terphenyl group;

a1 to a3 may be each independently 0 or 1, $R_{11}$ to $R_{13}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group;

a $C_1$-$C_{10}$ alkyl group and a $C_1$-$C_{10}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, a fluorenyl group, a pyridinyl group, a pyrazinyl group, a pyrimidinyl group, a pyridazinyl group, a triazinyl group, a dibenzofuranyl group, and a dibenzothiophenyl group;

a phenyl group, a naphthyl group, a fluorenyl group, a pyridinyl group, a pyrazinyl group, a pyrimidinyl group, a pyridazinyl group, a triazinyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a triazinyl group, a biphenyl group, a terphenyl group, and —Si($Q_{23}$)($Q_{24}$)($Q_{25}$); and —Si($Q_3$)($Q_4$)($Q_5$);

wherein $Q_3$ to $Q_5$ and $Q_{23}$ to $Q_{25}$ may be each independently selected from a hydrogen, a $C_1$-$C_{10}$ alkyl group, a $C_1$-$C_{10}$ alkoxy group, a phenyl group, a naphthyl group, a pyridinyl group, a pyrimidinyl group, and a triazinyl group, b1 to b3 may be each independently 0 or 1, $R_{14}$ to $R_{16}$ may be each independently a group represented by one of Formulae 2-1 to 2-108 (for example, by one of Formulae 3-1 to 3-41).

In some embodiments, the condensed cyclic compound represented by Formula 1 may be represented by one of Formulae 1-1 to 1-10, but it is not limited thereto:

Formula 1-1

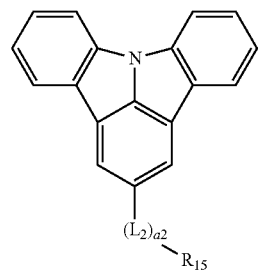

Formula 1-2

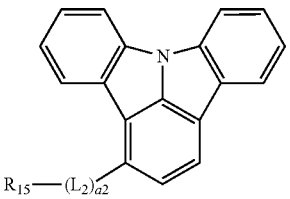

Formula 1-3

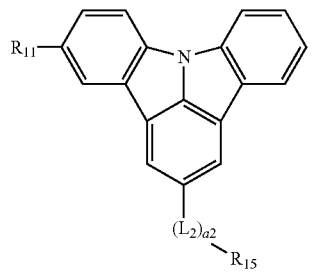

Formula 1-4

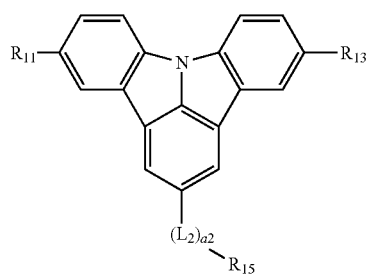

Formula 1-5

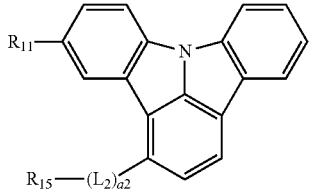

-continued

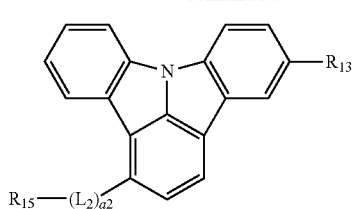
Formula 1-6

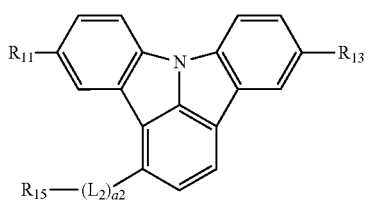
Formula 1-7

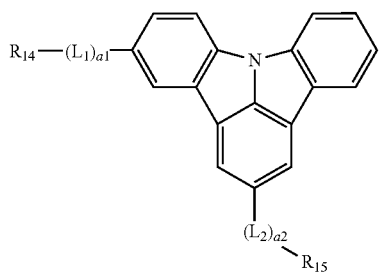
Formula 1-8

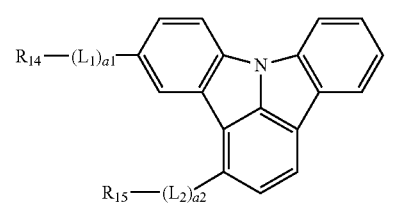
Formula 1-9

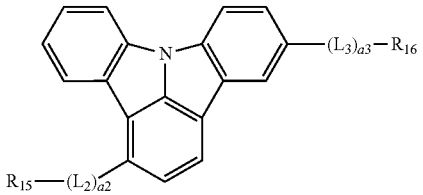
Formula 1-10 wherein in Formulae 1-1 to 1-10, the descriptions for $L_1$ to $L_3$, a1 to a3, and $R_{14}$ to $R_{16}$ may be the same as defined herein, $R_{11}$ to $R_{13}$ may be each independently selected from a phenyl group, a naphthyl group, a fluorenyl group, a pyridinyl group, a pyrazinyl group, a pyrimidinyl group, a pyridazinyl group, a quinolinyl group, an isoquinolinyl group, a quinoxalinyl group, a quinazolinyl group, a furanylene group, a benzofuranyl group, a thiophenyl group, a benzothiophenyl group, a thiazolyl group, an isothiazolyl group, an isoxazolyl group, an oxazolyl group, an oxadiazolyl group, a triazinyl group, a dibenzofuranyl group, and a dibenzothiophenyl group; and a phenyl group, a naphthyl group, a fluorenyl group, a pyridinyl group, a pyrazinyl group, a pyrimidinyl group, a pyridazinyl group, a quinolinyl group, an isoquinolinyl group, a quinoxalinyl group, a quinazolinyl group, a furanylene group, a benzofuranyl group, a thiophenyl group, a benzothiophenyl group, a thiazolyl group, an isothiazolyl group, an isoxazolyl group, an oxazolyl group, an oxadiazolyl group, a triazinyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a triazinyl group, a biphenyl group, a terphenyl group, and —Si($Q_{23}$)($Q_{24}$)($Q_{25}$);

wherein $Q_{23}$ to $Q_{25}$ may be each independently selected from a hydrogen, a $C_1$-$C_{10}$ alkyl group, a $C_1$-$C_{10}$ alkoxy group, a phenyl group, a naphthyl group, a pyridinyl group, a pyrimidinyl group, and a triazinyl group.

In some embodiments, in Formulae 1-1 to 1-10, $L_1$ to $L_3$ may be each independently a group represented by one of Formulae 5-1 to 5-9, a1 to a3 may be each independently 0 or 1, $R_{14}$ to $R_{16}$ may be each independently a group represented by one of Formulae 2-1 to 2-108 (for example, by one of Formulae 3-1 to 3-41), $R_{11}$ to $R_{13}$ may be each independently selected from a phenyl group, a naphthyl group, a fluorenyl group, a pyridinyl group, a pyrazinyl group, a pyrimidinyl group, a pyridazinyl group, a quinolinyl group, an isoquinolinyl group, a quinoxalinyl group, a quinazolinyl group, a furanylene group, a benzofuranyl group, a thiophenyl group, a benzothiophenyl group, a thiazolyl group, an isothiazolyl group, an isoxazolyl group, an oxazolyl group, an oxadiazolyl group, a triazinyl group, a dibenzofuranyl group, and a dibenzothiophenyl group; and a phenyl group, a naphthyl group, a fluorenyl group, a pyridinyl group, a pyrazinyl group, a pyrimidinyl group, a pyridazinyl group, a quinolinyl group, an isoquinolinyl group, a quinoxalinyl group, a quinazolinyl group, a furanylene group, a benzofuranyl group, a thiophenyl group, a benzothiophenyl group, a thiazolyl group, an isothiazolyl group, an isoxazolyl group, an oxazolyl group, an oxadiazolyl group, a triazinyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a triazinyl group, a biphenyl group, a terphenyl group, and —Si($Q_{23}$)($Q_{24}$)($Q_{25}$);

wherein $Q_{23}$ to $Q_{25}$ may be each independently selected from a hydrogen, a $C_1$-$C_{10}$ alkyl group, a $C_1$-$C_{10}$ alkoxy group, a phenyl group, a naphthyl group, a pyridinyl group, a pyrimidinyl group, and a triazinyl group, but they are not limited thereto.

A molecular weight of the condensed cyclic compound represented by Formula 1 may be, for example, in a range of about 300 Da to about 2,000 Da. In some embodiments, a molecular weight of the condensed cyclic compound represented by Formula 1 may be, for example, in a range of about 348 Da to about 1,500 Da. In some embodiments, a molecular weight of the condensed cyclic compound represented by Formula 1 may be, for example, in a range of about 348 Da to about 1,000 Da. When a molecular weight of the condensed cyclic compound represented by Formula 1 is within the above described range, the condensed cyclic compound may be easily purified by using a sublimation refining method.

In Formula 1, at least one of substituents of the substituted 5-membered carbocyclic group, substituted 6-membered carbocyclic group, substituted 5-membered heterocyclic group, substituted 6-membered heterocyclic group, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{14}$ arylene group, substituted $C_1$-$C_{13}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{14}$ aryl group, substituted $C_6$-$C_{14}$ aryloxy group, substituted $C_6$-$C_{14}$ arylthio group, substituted $C_1$-$C_{13}$ heteroaryl group, substituted monovalent non-aromatic condensed polycyclic group, and substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_6$-$C_{14}$ aryloxy group, a $C_6$-$C_{14}$ arylthio group, a $C_1$-$C_{13}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{14}$ alkyl group, a $C_2$-$C_{14}$ alkenyl group, a $C_2$-$C_{14}$ alkynyl group, a $C_1$-$C_{13}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_6$-$C_{14}$ aryloxy group, a $C_6$-$C_{14}$ arylthio group, a $C_1$-$C_{13}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$); and —N($Q_{21}$)($Q_{22}$), —Si($Q_{23}$)($Q_{24}$)($Q_{25}$), and —B($Q_{26}$)($Q_{27}$);

wherein $Q_1$ to $Q_7$, $Q_{11}$ to $Q_{17}$, and $Q_{21}$ to $Q_{27}$ may be each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{13}$ heteroaryl group, a monovalent non-aromatic condensed polycyclic group, and a monovalent non-aromatic condensed heteropolycyclic group.

In Formula 1, the number of rings that are condensed with each other in the divalent non-aromatic condensed polycyclic group, divalent non-aromatic condensed heteropolycyclic group, monovalent non-aromatic condensed polycyclic group, and monovalent non-aromatic condensed heteropolycyclic group may be 2 or 3.

In some embodiments, the condensed cyclic compound may be selected from Compounds 1 to 68 below.

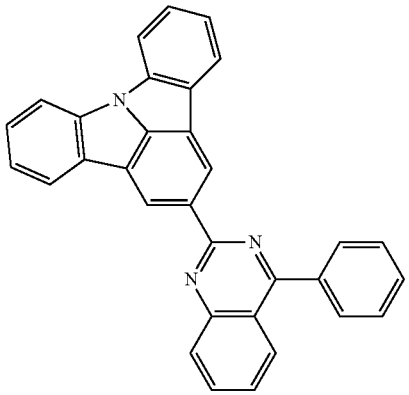

1

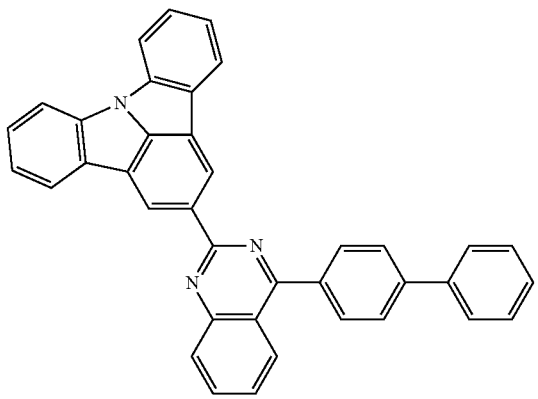

2

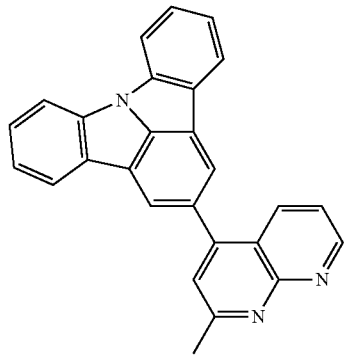

3

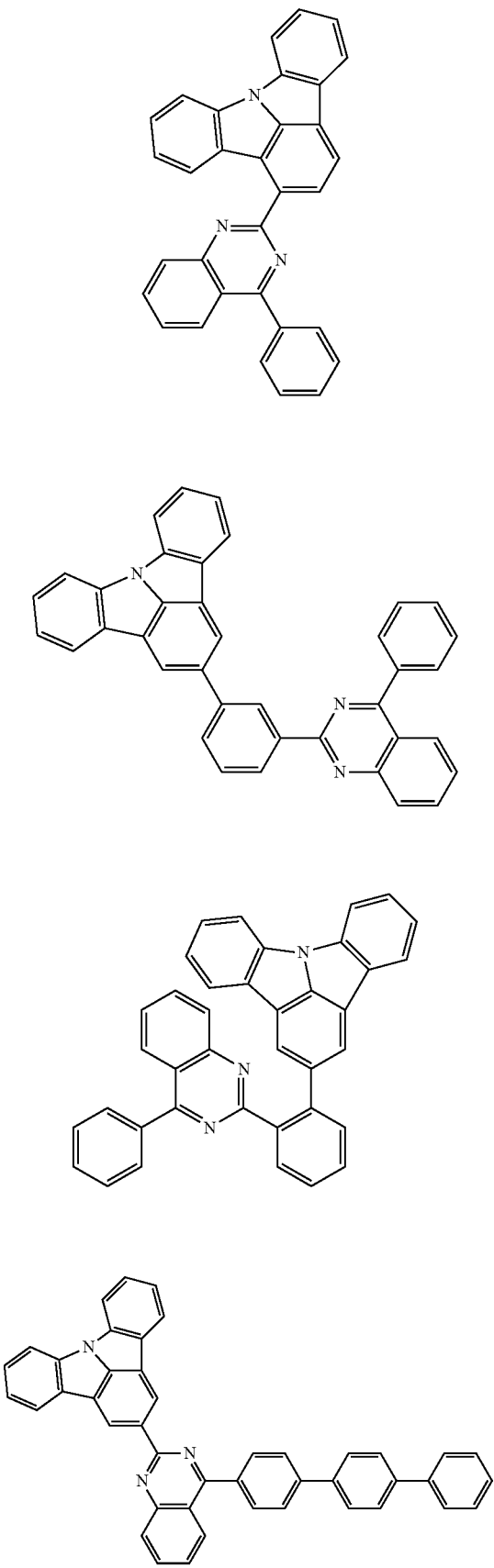
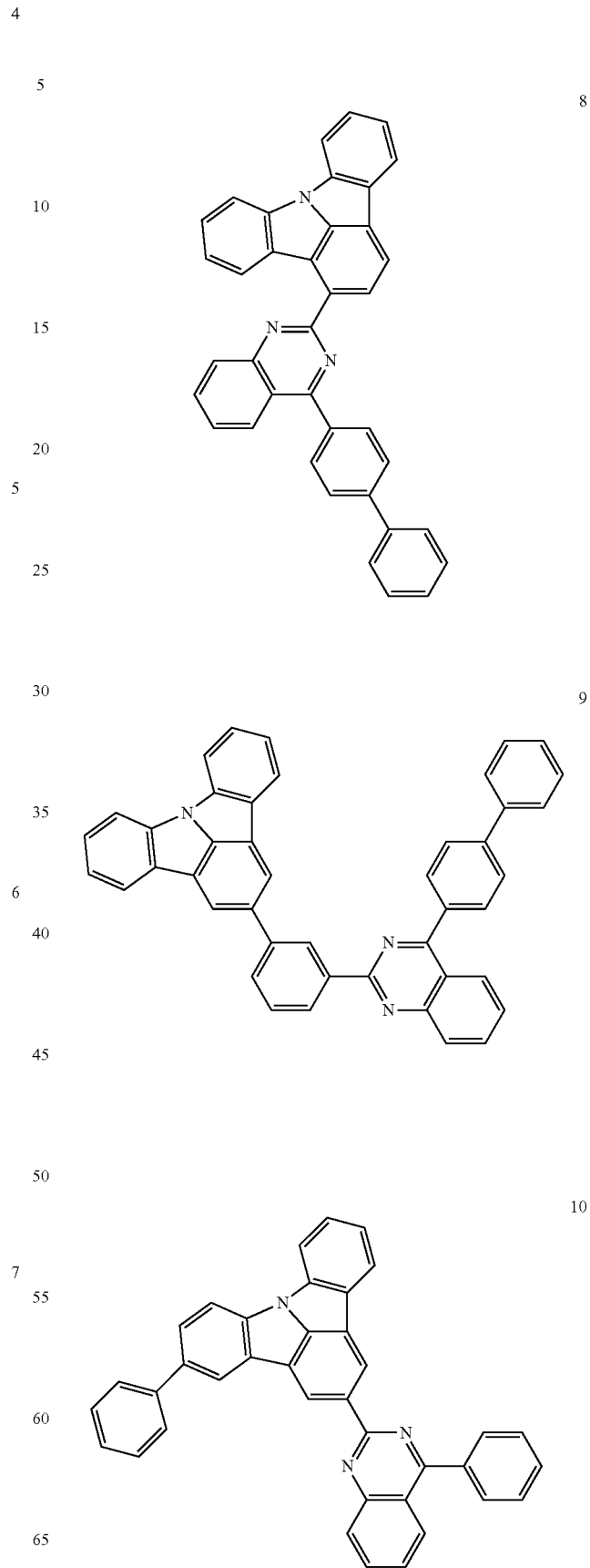

11
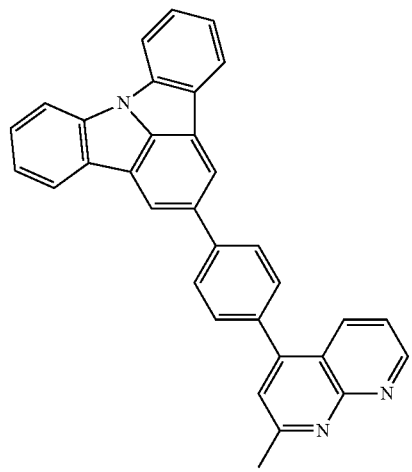
12
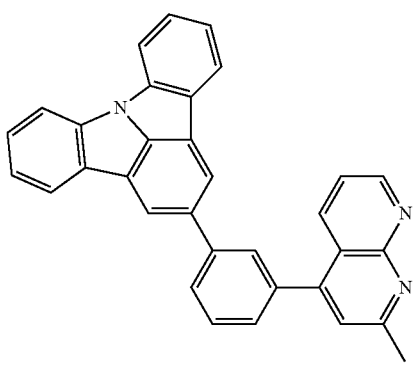
13
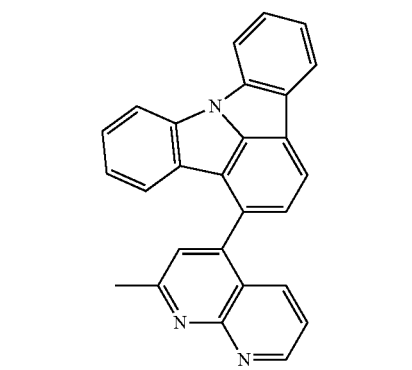
14
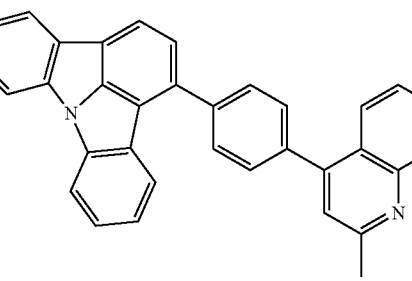
15
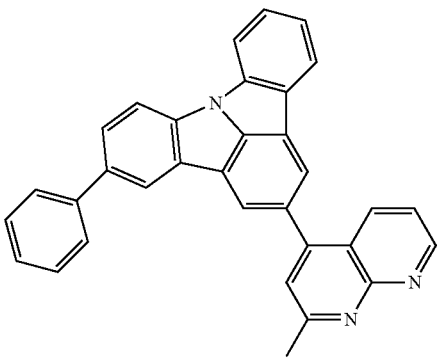
16
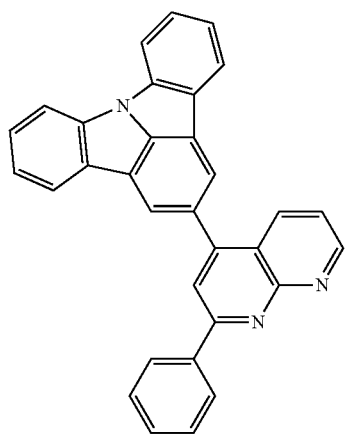
17
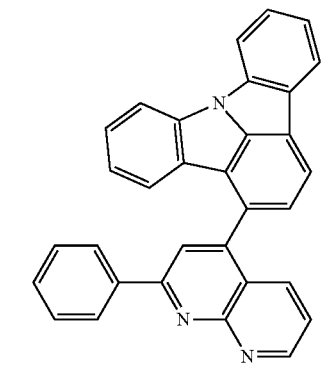
18
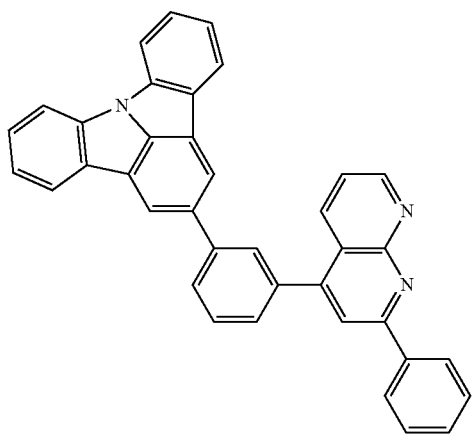

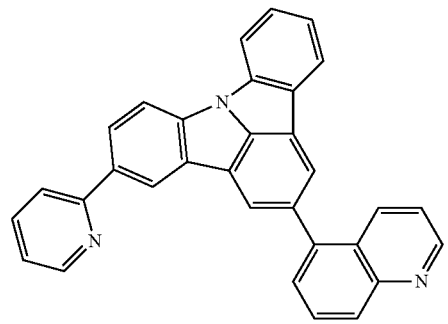
19
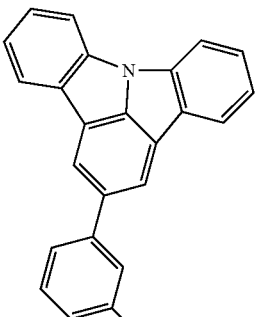
23
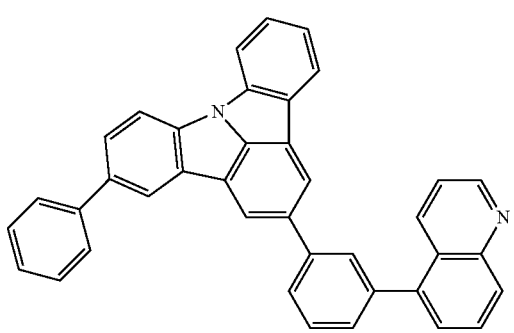
20
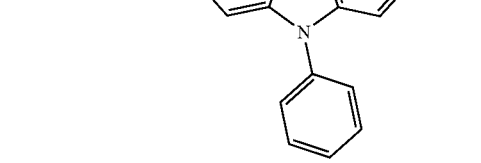
20
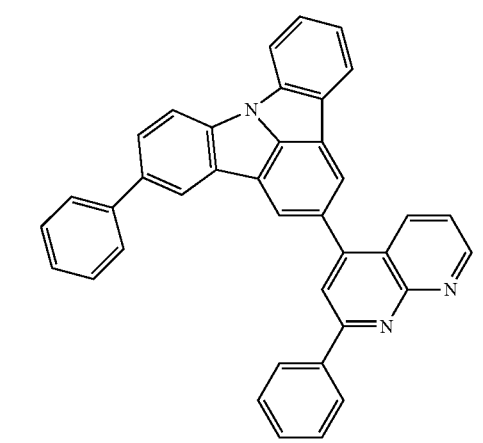
21
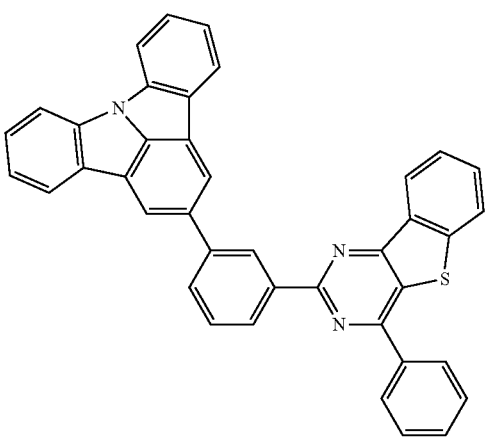
24
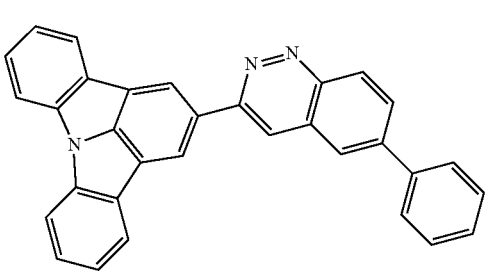
25
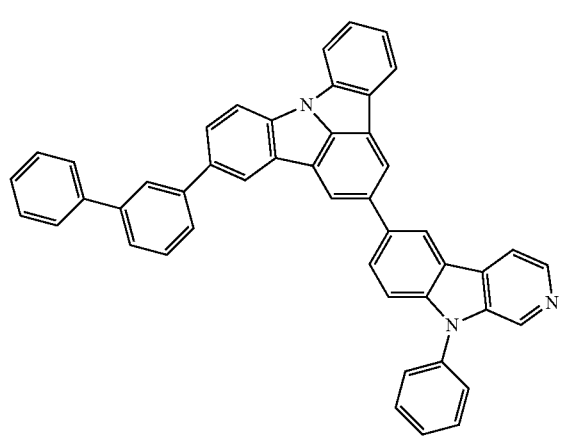
22
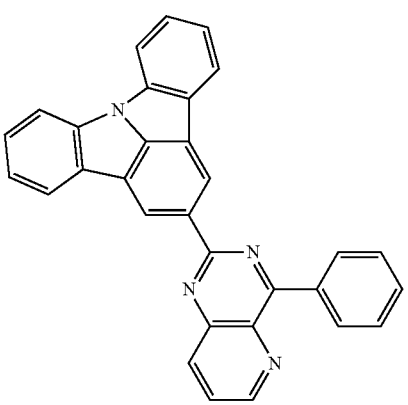
26

27
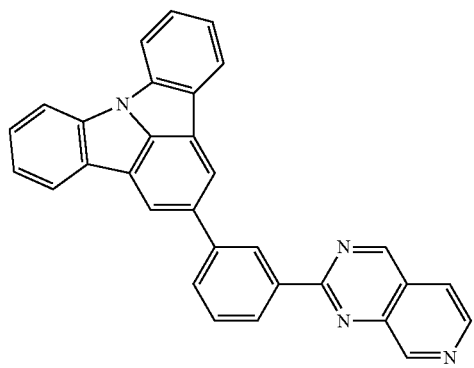
28
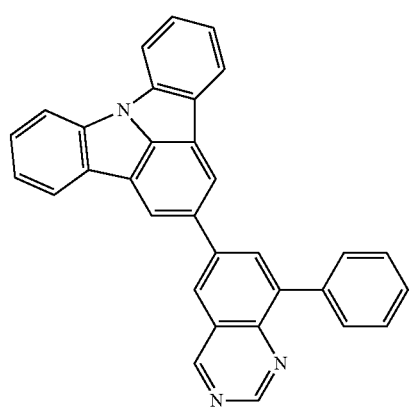
29
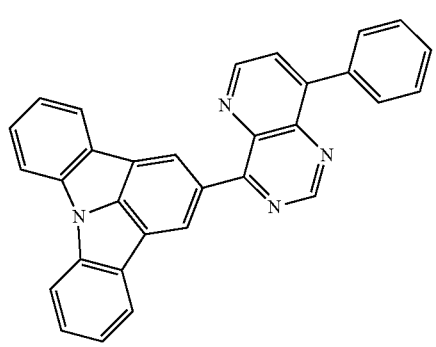
30
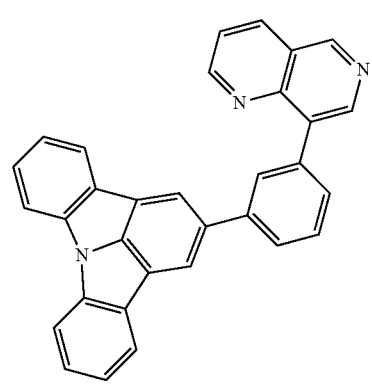
31
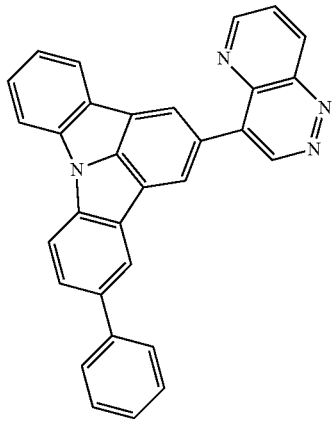
32
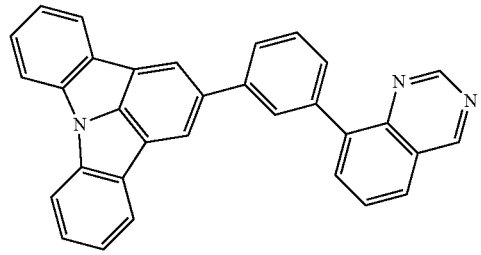
33
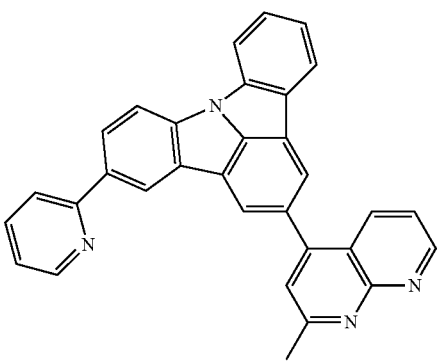
34
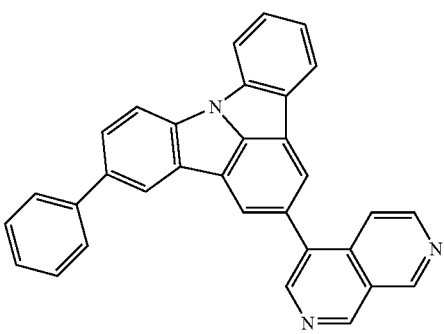

35
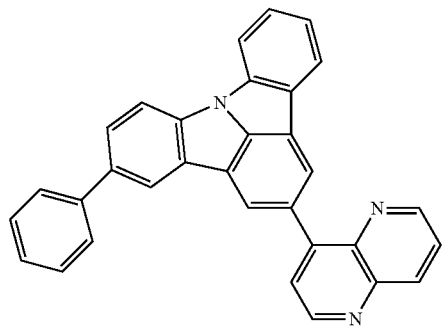
36
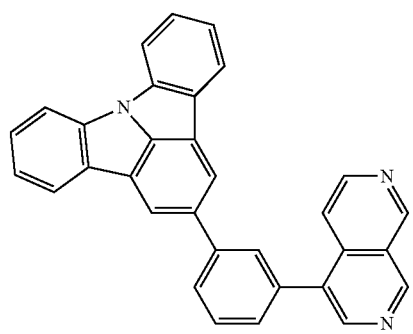
37
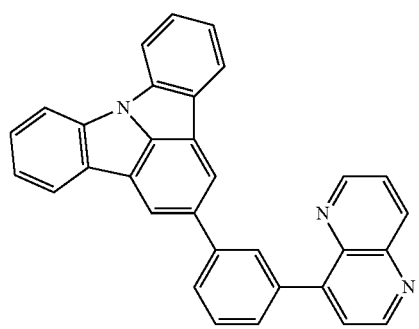
38
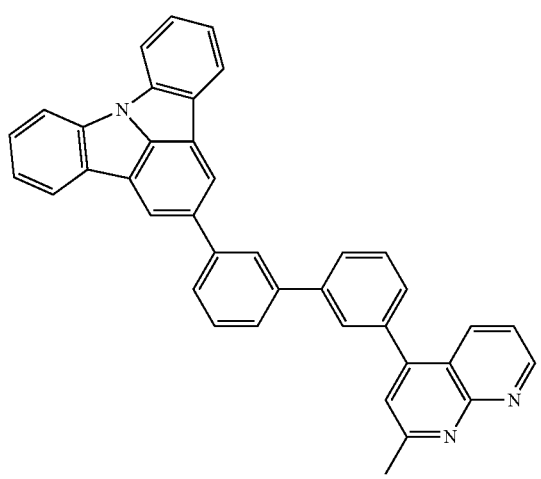
39
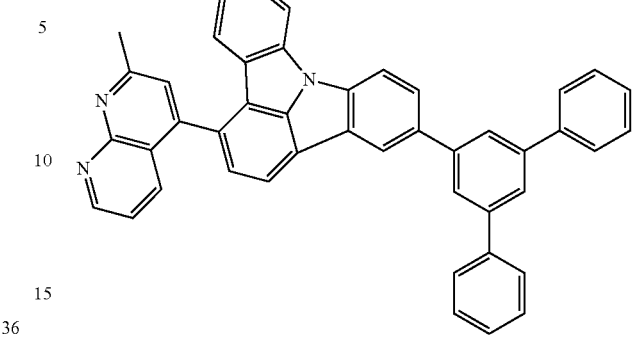
40
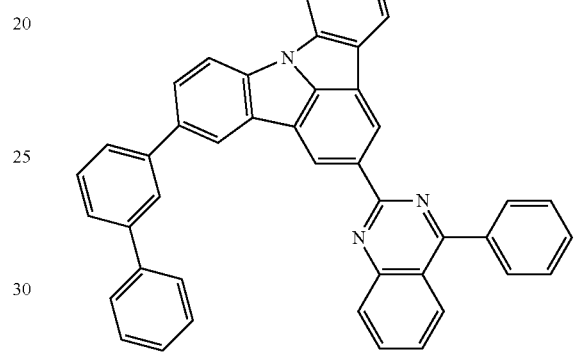
41
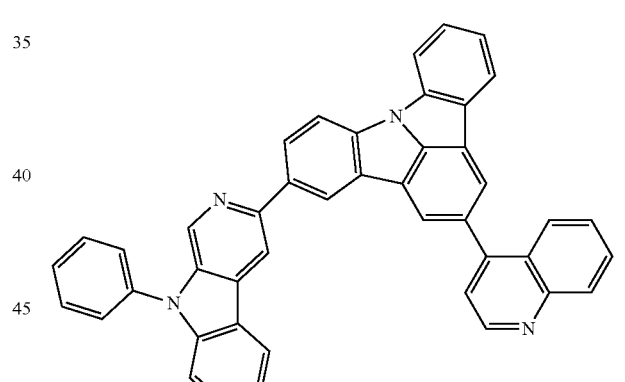
42
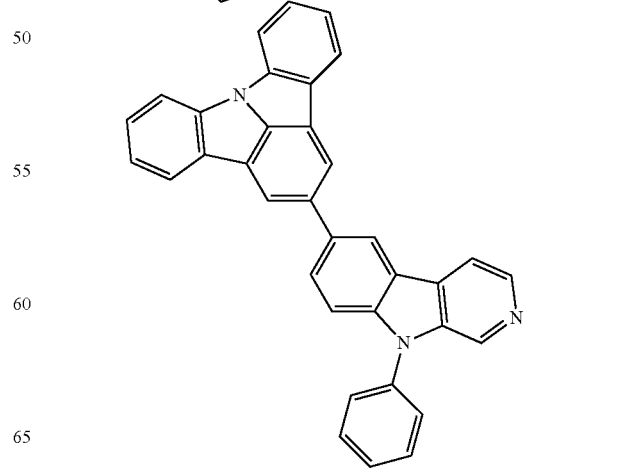

43
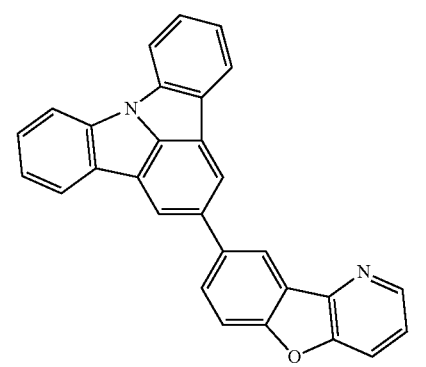
44
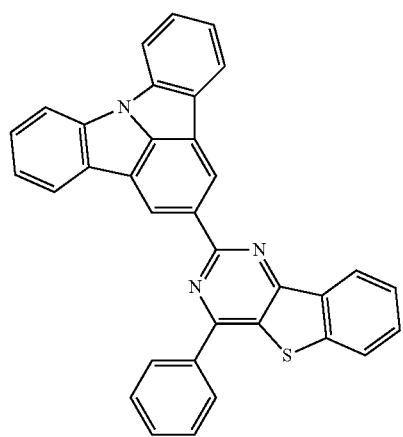
45
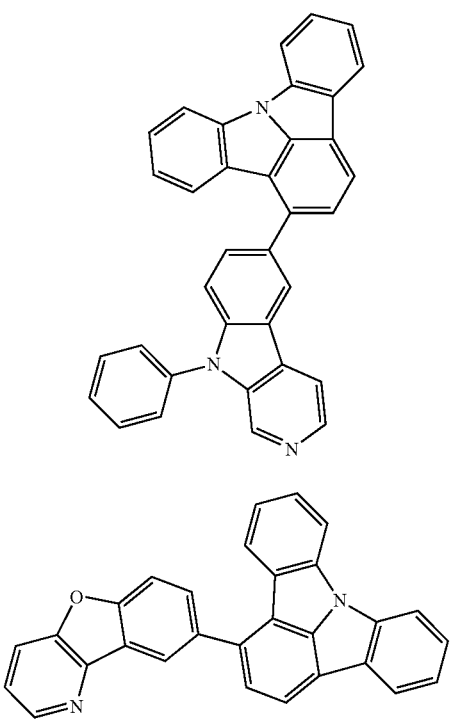
46
47
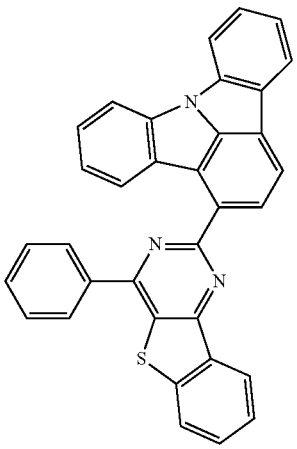
48
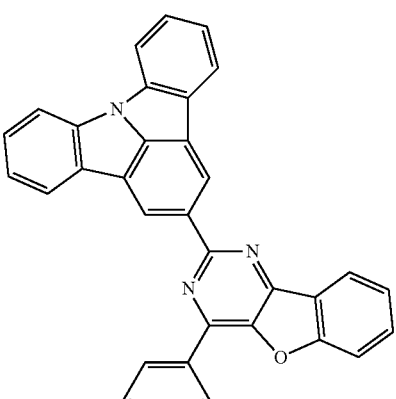
49
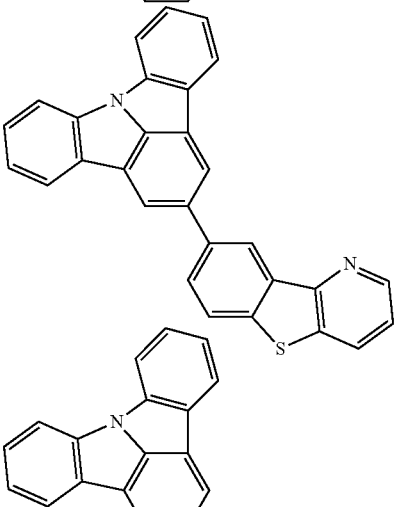
50
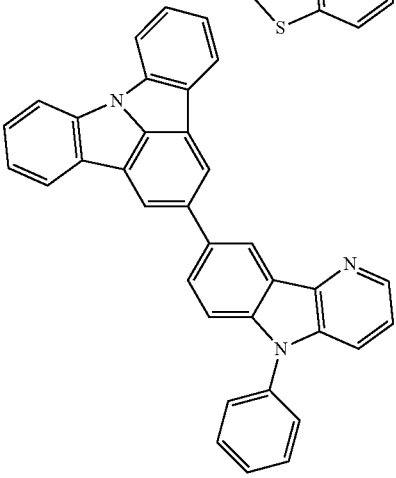

57
-continued
51
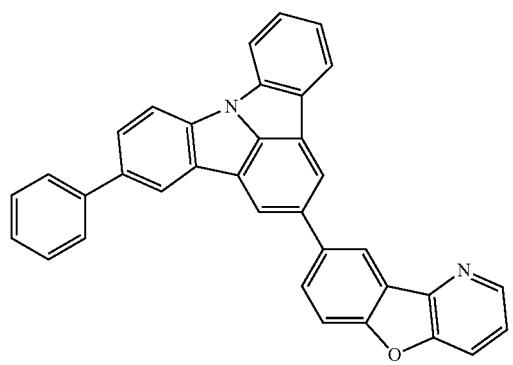
52
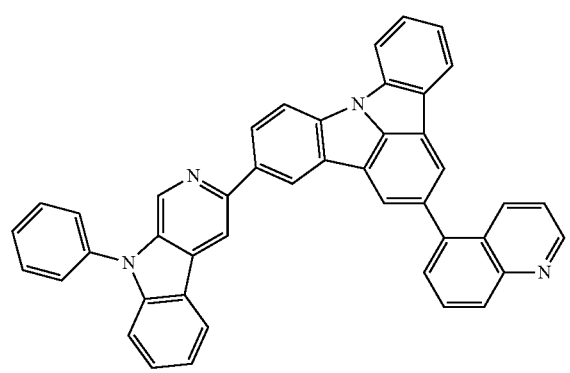
53
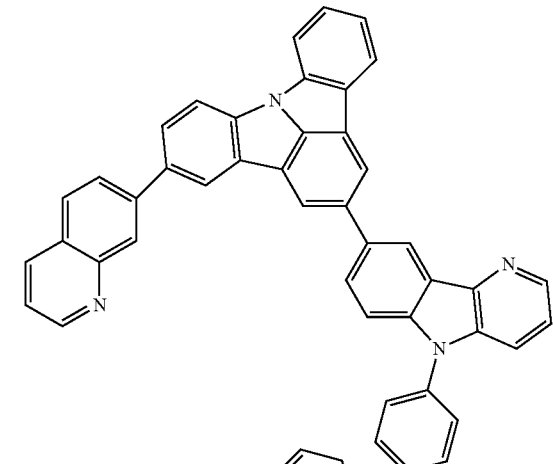
54
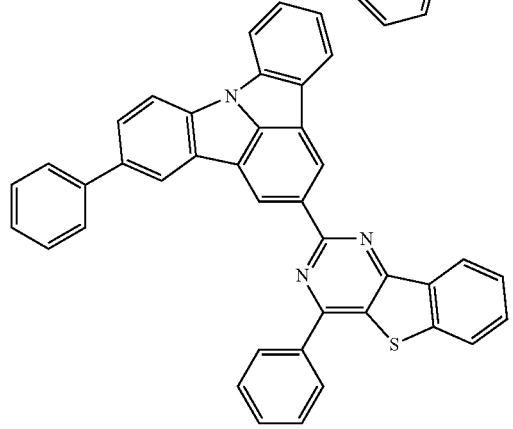
58
-continued
55
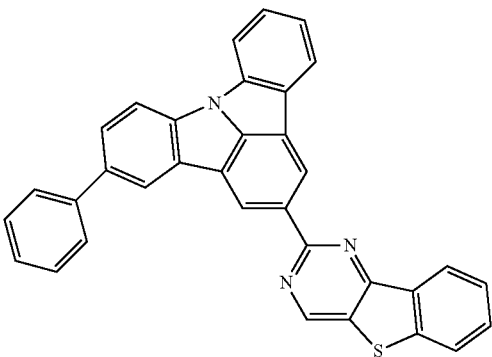
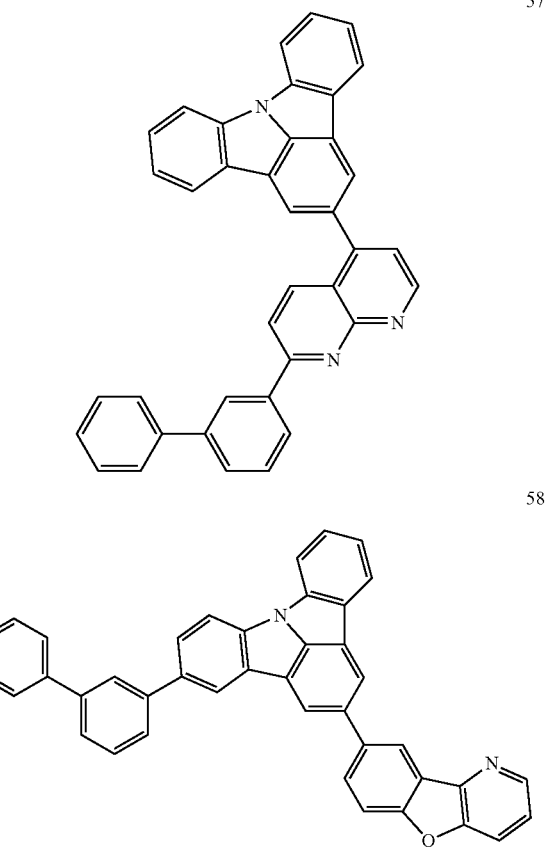

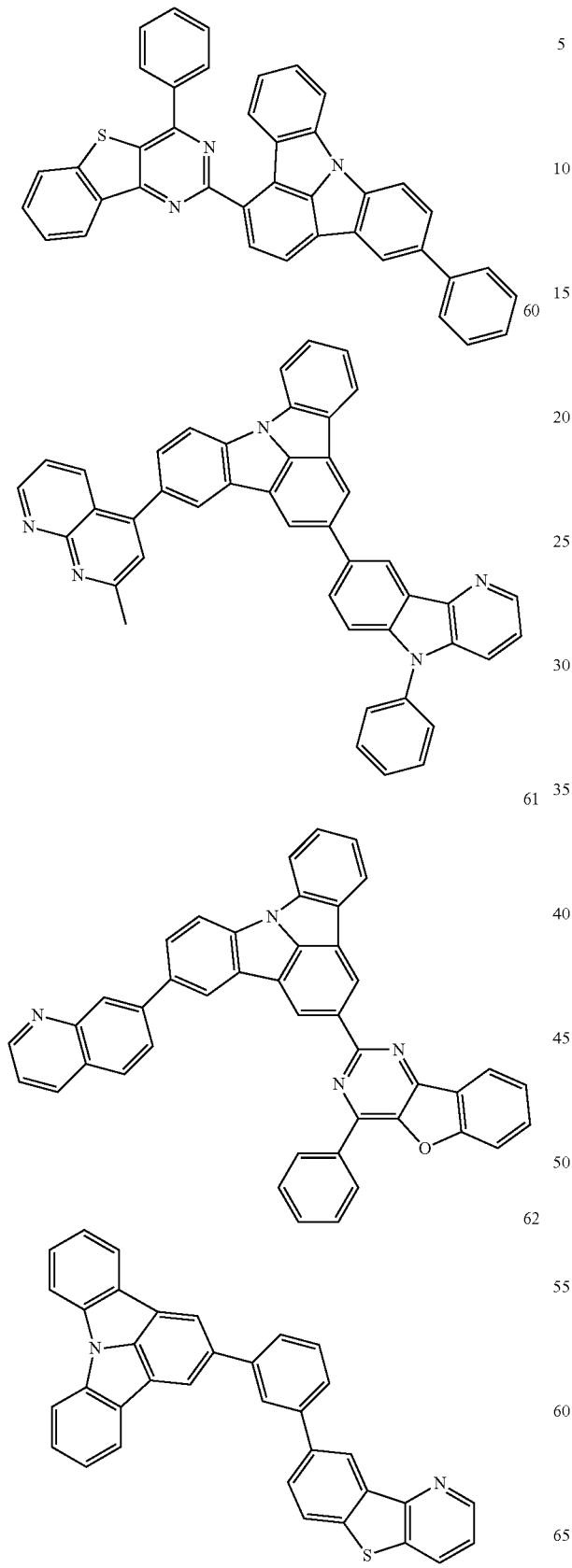
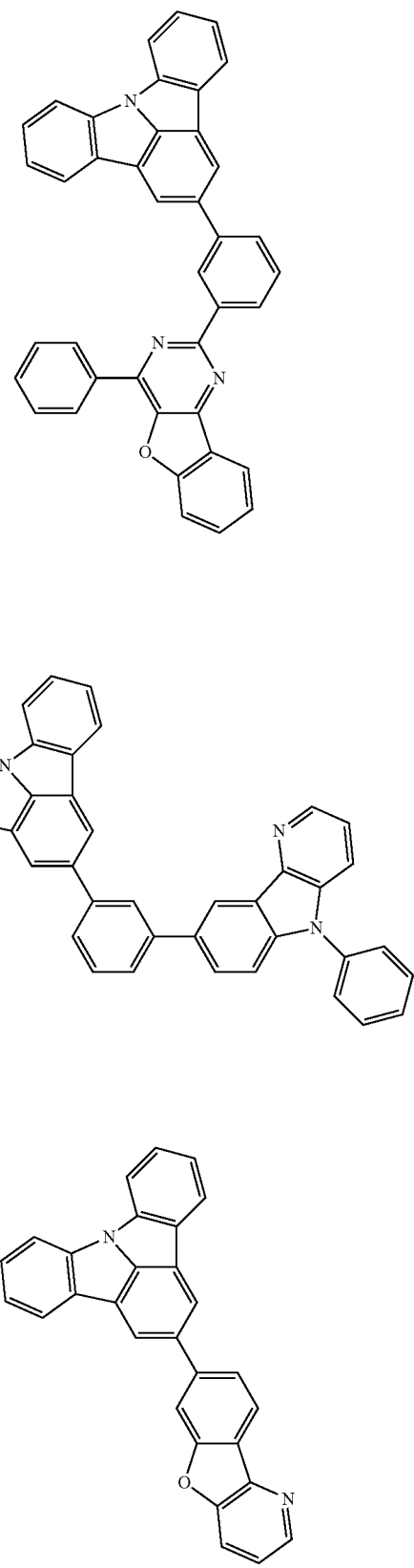

-continued

66
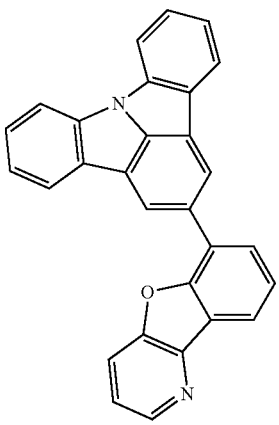

67
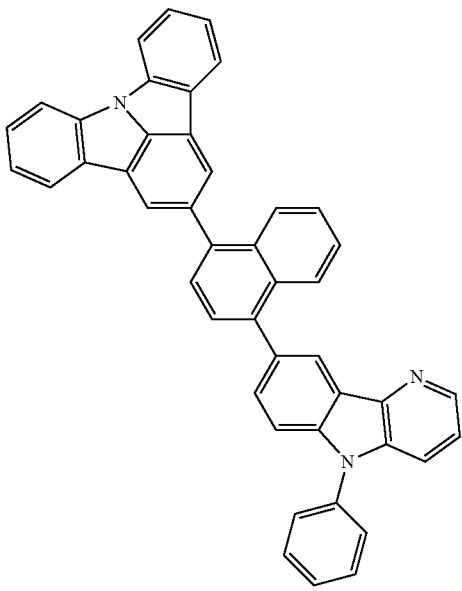

68
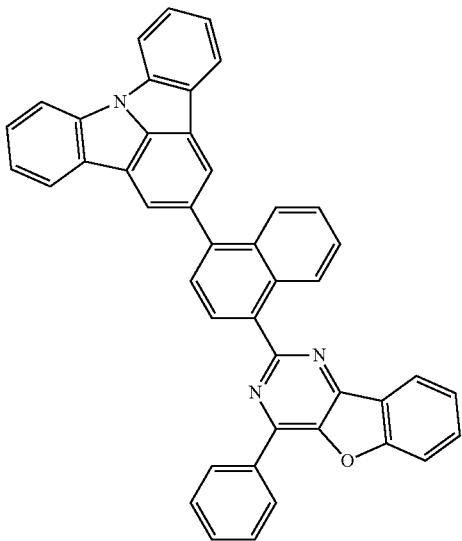

$R_{14}$ to $R_{16}$ in the condensed cyclic compound represented by Formula 1 are each independently a group represented by Formula 2, and since $c1+c2+c3≥1$, the condensed cyclic compound represented by Formula 1 essentially includes at least one selected from $R_{14}$ to $R_{16}$. Formula 2 is a condensed ring in which a plurality of rings are condensed with each other. Additionally, at least one selected from $X_1$ to $X_8$ in Formula 2 is N, that is, Formula 2 essentially includes N as a ring-forming atom. Moreover, when ring $A_1$ in Formula 2 includes a hetero atom, the hetero atom is selected from the group consisting of O, S, and $N(R_9)$. Accordingly, the condensed cyclic compound represented by Formula 1 can have electric characteristics suitable for an organic light-emitting device.

Also, the number of rings condensed with each other among the divalent non-aromatic condensed polycyclic group, the divalent non-aromatic condensed heteropolycyclic group, the monovalent non-aromatic condensed polycyclic group, and the monovalent non-aromatic condensed heteropolycyclic group included in the condensed cyclic compound represented by Formula 1 is 2 or 3. Thus, the condensed cyclic compound can have excellent thermal stability. For example, the condensed cyclic compound may have a decomposition temperature that is higher than a sublimation temperature under a vacuum degree in a range of about $10^{-8}$ torr to about $10^{-3}$ torr. Therefore, the condensed cyclic compound may provide excellent manufacturing process efficiency, and an organic light-emitting device including the same may have improved device stability when the device is being used, thereby providing a device with a long lifespan.

In addition, the condensed cyclic compound represented by Formula 1 may have a relatively low level of the highest occupied molecular orbital (HOMO) energy level as a material for an organic light-emitting device, and a variety of properties may be achieved by substituting a substituent, thereby having improved charge transporting ability. In conclusion, an organic light-emitting device employing the condensed cyclic compound represented by Formula 1 may have a high efficiency, low driving voltage, high luminance, and long lifespan.

For example, the HOMO energy level, lowest unoccupied molecular orbital (LUMO) energy level, $T_1$ energy level, and $S_1$ energy level of the Compounds 1, 2, 4, 5, 6, 9, 17, 35, 48, 54, 63, 65, 67, and 68 were simulated by using Gaussian. The simulation evaluation results are shown in Table 1:

TABLE 1

| | HOMO (eV) | LUMO (eV) | $T_1$ (eV) | $S_1$ (eV) |
|---|---|---|---|---|
| Compound 1 | −5.435 | −1.836 | 2.514 | 3.182 |
| Compound 2 | −5.433 | −1.888 | 2.488 | 3.138 |
| Compound 4 | −5.424 | −2.011 | 2.414 | 2.938 |
| Compound 5 | −5.401 | −1.893 | 2.557 | 3.076 |
| Compound 6 | −5.350 | −1.824 | 2.576 | 3.031 |
| Compound 9 | −5.398 | −1.941 | 2.538 | 3.108 |
| Compound 17 | −5.638 | −1.844 | 2.740 | 3.438 |
| Compound 35 | −5.488 | −1.777 | 2.697 | 3.285 |
| Compound 48 | −5.440 | −1.862 | 2.724 | 3.138 |
| Compound 54 | −5.387 | −1.782 | 2.761 | 3.167 |
| Compound 63 | −5.415 | −1.889 | 2.835 | 3.178 |
| Compound 65 | −5.510 | −1.399 | 2.868 | 3.563 |
| Compound 67 | −5.186 | −1.284 | 2.544 | 3.440 |
| Compound 68 | −5.310 | −1.888 | 2.423 | 2.970 |

Referring to Table 1, it was confirmed that the condensed cyclic compound represented by Formula 1 is suitable for a material to be used in an organic layer of an organic light-emitting device, for example, in an auxiliary layer or emission layer.

A method of synthesizing the condensed cyclic compound represented by Formula 1 may be understood to one of ordinary skill in the art by referring to Synthesis Examples described below.

Therefore, the condensed cyclic compound represented by Formula 1 may be appropriate to be used in an organic layer of an organic light-emitting device, for example as a host in an emission layer of the organic layer.

Thus, according to another aspect, provided is an organic light-emitting device that may include:

a first electrode;

a second electrode; and an organic layer disposed between the first electrode and the second electrode, wherein the organic layer includes an emission layer and at least one condensed cyclic compound represented by Formula 1.

Since the organic light-emitting device has an organic layer including the condensed cyclic compound represented by Formula 1, the organic light-emitting device may have a low driving voltage, high efficiency, high luminance, and long lifespan.

The condensed cyclic compound represented by Formula 1 may be included in between a pair of electrodes of the organic light-emitting device. In some embodiments, the condensed cyclic compound may be included in at least one selected from the emission layer, a hole transport region (for example, including at least one selected from a hole injection layer, a hole transport layer, and an electron blocking layer) disposed between the first electrode and the emission layer, and an electron transport region (for example, including at least one selected from a hole blocking layer, an electron transport layer, and an electron injection layer) disposed between the emission layer and the second electrode. In some embodiments, the condensed cyclic compound represented by Formula 1 may be included in the emission layer. Here, the emission layer may further include a dopant, and the condensed cyclic compound included in the emission layer may serve as a host. The emission layer may be a green emission layer that emits green light or a blue emission layer that emits blue light, and the dopant may be a phosphorescent dopant.

As used herein, the expression the "(organic layer) includes at least one condensed cyclic compound" may be construed as meaning the "(organic layer) may include one condensed cyclic compound in a range of Formula 1 or two different condensed cyclic compounds in a range of Formula 1".

For example, the organic layer may include only Compound 2 as the condensed cyclic compound. In this regard, Compound 2 may be included in the emission layer of the organic light-emitting device. Alternatively, the organic layer may include Compound 2 and Compound 5 as the condensed cyclic compounds. In this regard, Compound 2 and Compound 5 may be included in the same layer (for example, both Compound 2 and Compound 5 may be included in the emission layer) or respectively included in different layers.

The first electrode may be an anode, which is a hole injection electrode, and the second electrode may be a cathode, which is an electron injection electrode. Alternatively, the first electrode may be a cathode, which is an electron injection electrode, and the second electrode may be an anode, which is a hole injection electrode.

For example, the first electrode may be an anode, the second electrode may be a cathode, and the organic layer may include:

i) a hole-transport region disposed between the first electrode and the emission layer, wherein the hole-transport region may include at least one selected from a hole injection layer, a hole-transport layer, and an electron blocking layer; and ii) an electron-transport region disposed between the emission layer and the second electrode, wherein the electron-transport region may include at least one selected from a hole blocking layer, an electron transport layer, and an electron injection layer.

As used herein, the term the "organic layer" refers to a single and/or a plurality of layers disposed between the first electrode and the second electrode in an organic light-emitting device. The "organic layer" may include not only organic compounds but also organometallic complexes including metals.

FIG. 1 is a schematic view of an organic light-emitting device 10 according to an embodiment. Hereinafter, a structure and a method of manufacturing the organic light-emitting device according to an embodiment will be described with reference to FIG. 1.

The organic light-emitting device 10 includes a first electrode 11, an organic layer 15, and a second electrode 19, which are sequentially layered in the stated order.

A substrate may be additionally disposed under the first electrode 11 or on the second electrode 19. The substrate may be a conventional substrate that is used in an organic light-emitting device, such as glass substrate or a transparent plastic substrate, each having excellent mechanical strength, thermal stability, transparency, surface smoothness, ease of handling, and water repellency.

The first electrode 11 may be formed by vacuum-depositing or sputtering a material for forming the first electrode on the substrate. The first electrode 11 may be an anode. The material for the first electrode 11 may be selected from materials with a high work function for an easy hole injection. The first electrode 11 may be a reflective electrode, a semi-transmissive electrode, or a transmissive electrode. The material for the first electrode 11 may be selected from indium tin oxide (ITO), indium zinc oxide (IZO), tin oxide ($SnO_2$), and zinc oxide (ZnO). Alternatively, a metal such as magnesium (Mg), aluminum (Al), aluminum-lithium (Al—Li), calcium (Ca), magnesium-indium (Mg—In), and magnesium-silver (Mg—Ag).

The first electrode 11 may have a single layer structure or a multi-layer structure including a plurality of layers. For example, the first electrode 11 may have a triple-layer structure of ITO/Ag/ITO, but it is not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, hole transport layer, electron blocking layer, and buffer layer.

The hole transport region may only include a hole injection layer or a hole transport layer. Alternatively, the hole transport region may include a structure in which a hole injection layer/a hole transport layer or a hole injection layer/a hole transport layer/an electron blocking layer are sequentially layered on the first electrode 11.

When the hole transport region includes a hole injection layer, the hole injection layer (HIL) may be formed on the first electrode 11 by using various methods such as vacuum-deposition, spin coating, casting, and Langmuir-Blodgett (LB) method.

A hole injection layer is formed by vacuum-deposition, for example, the vacuum-deposition may be performed at a deposition temperature in a range of about 100° C. to about 500° C., at a vacuum degree in a range of about $10^{-8}$ to about $10^{-3}$ torr, and at a deposition rate in a range of about 0.01 Angstroms per second (Å/sec) to about 100 Å/sec, though the conditions may vary depending on a compound that is used as a hole injection material and a structure and thermal properties of a desired hole injection layer, but it is not limited thereto.

When a hole injection layer is formed by spin coating, the spin coating may be performed at a coating rate in a range of about 2,000 revolutions per minute (rpm) to about 5,000 rpm, and at a temperature in a range of about 80° C. to 200° C. for removing a solvent after the spin coating, though the conditions may vary depending on a compound that is used as a hole injection material and a structure and thermal properties of a desired HIL, but is not limited thereto.

The conditions for forming a hole transport layer and an electron blocking layer may be inferred based on the conditions for forming the hole injection layer.

The hole transport region may include at least one selected from m-MTDATA, TDATA, 2-TNATA, NPB, β-NPB, TPD, a spiro-TPD, a spiro-NPB, methylated-NPB, TAPC, HMTPD, 4,4',4''-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), (polyaniline)/poly(4-styrenesulfonate) (PANI/PSS), a compound represented by Formula 201 below, and a compound represented by Formula 202 below:

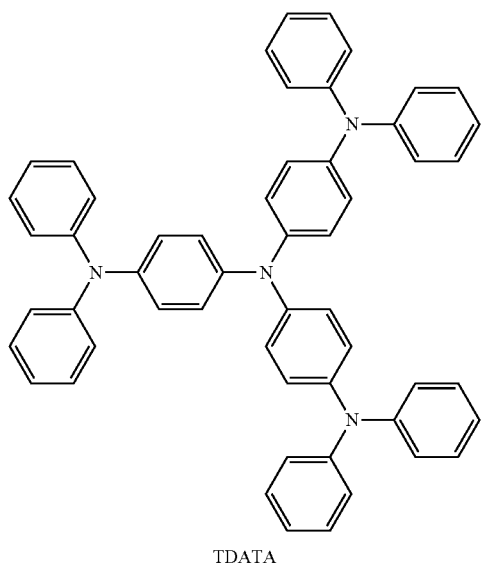

TDATA

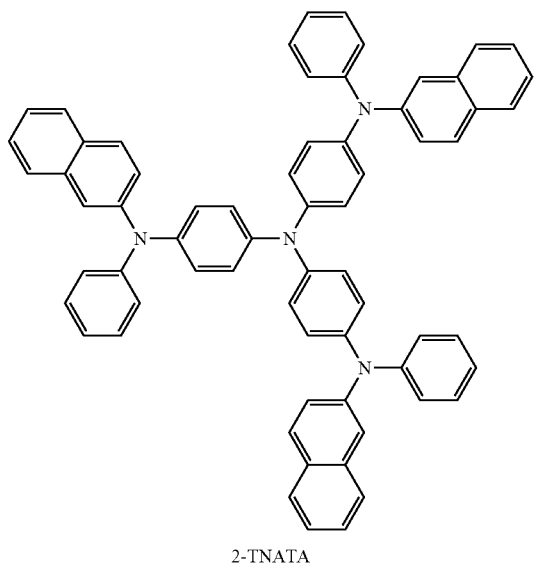

2-TNATA

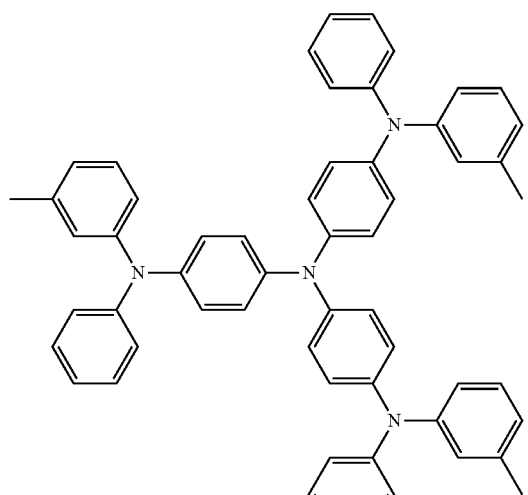

m-MTDATA

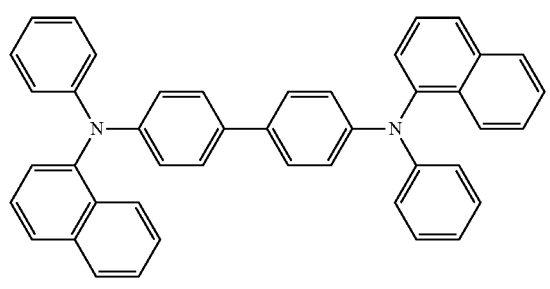

NPB

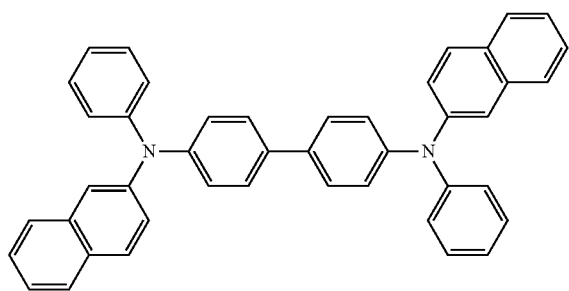

β-NPB

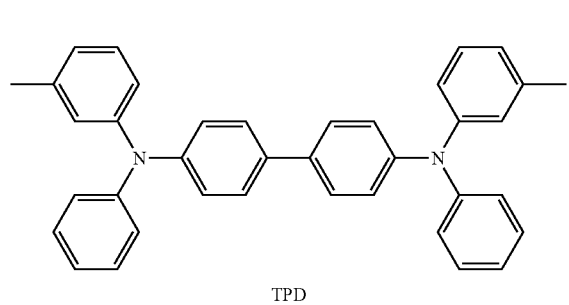

TPD

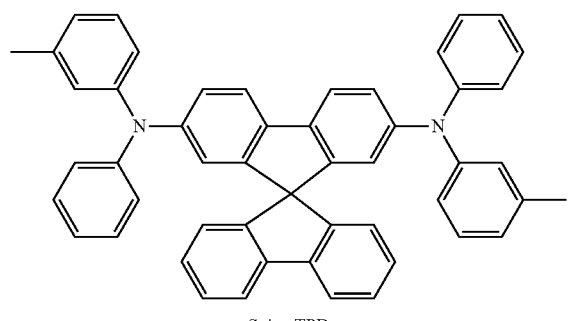

Spiro-TPD

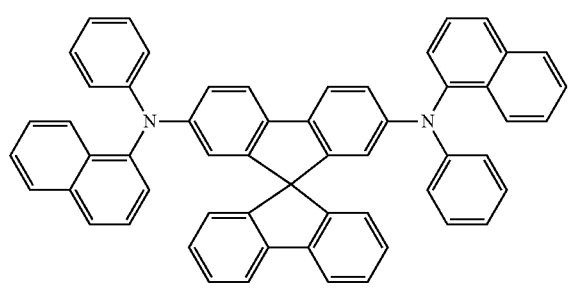

Spiro-NPB

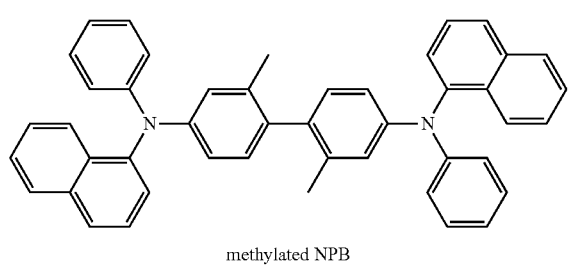

methylated NPB

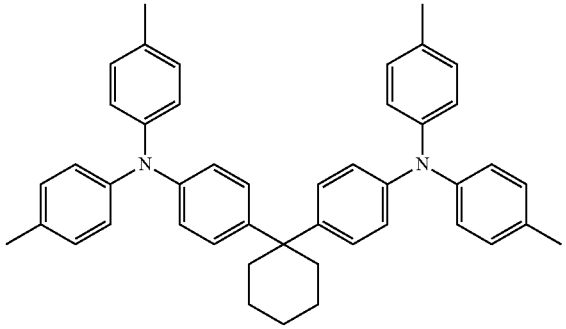

TAPC

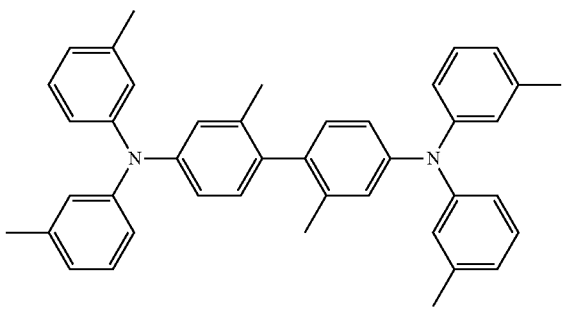

HMTPD

Formula 201

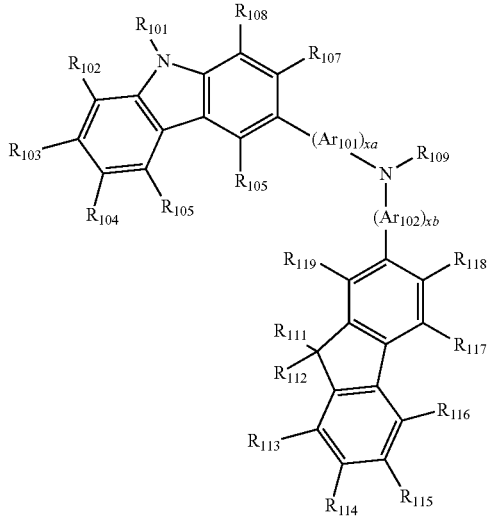

Formula 202

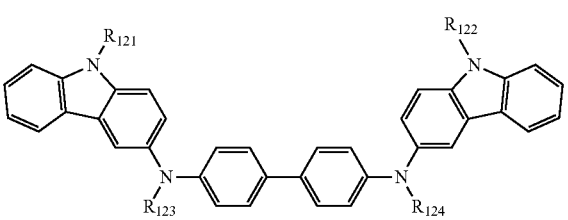

$Ar_{101}$ and $Ar_{102}$ in Formula 201 may be each independently selected from
a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

In Formula 201, xa may be each independently an integer selected from 0 to 5, and xb may be an integer selected from 0, 1, and 2. In some embodiments, xa may be 1 and xb may be 0, but they are not limited thereto.

In Formulae 201 and 202, $R_{101}$ to $R_{108}$, $R_{111}$ to $R_{119}$, and $R_{121}$ to $R_{124}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, or a hexyl group), and a $C_1$-$C_{10}$ alkoxy group (for example, a methoxy group, an ethoxy group, a propoxy group, a butoxy group, or a pentoxy group);

a $C_1$-$C_{10}$ alkyl group and a $C_1$-$C_{10}$ alkoxy group, each substituted with at least one selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but they are not limited thereto.

In Formula 201, $R_{109}$ may be selected from a phenyl group, a naphthyl group, an anthracenyl group, and a pyridinyl group; and a phenyl group, a naphthyl group, an anthracenyl group, and a pyridinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group.

According to an embodiment, the compound represented by Formula 201 may be represented by Formula 201A, but it is not limited thereto:

Formula 201A

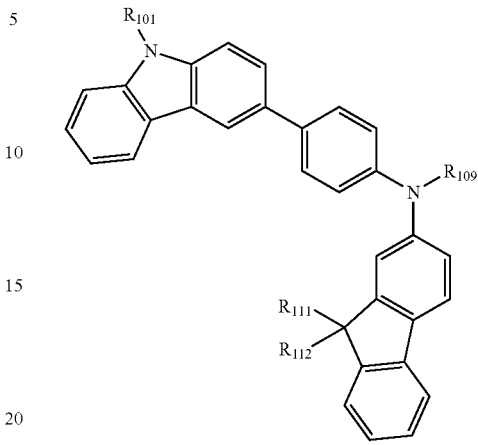

Descriptions for $R_{101}$, $R_{111}$, $R_{112}$, and $R_{109}$ in Formula 201A are the same as described above.

For example, the compound represented by Formula 201 and the compound represented by Formula 202 may include Compounds HT1 to HT20, but they are not limited thereto:

HT1

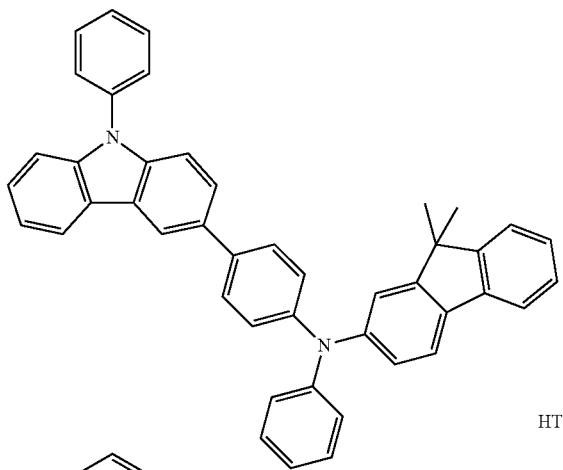

HT2

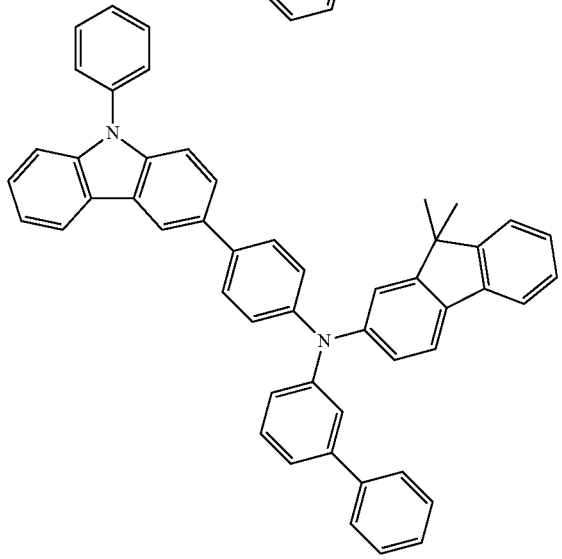

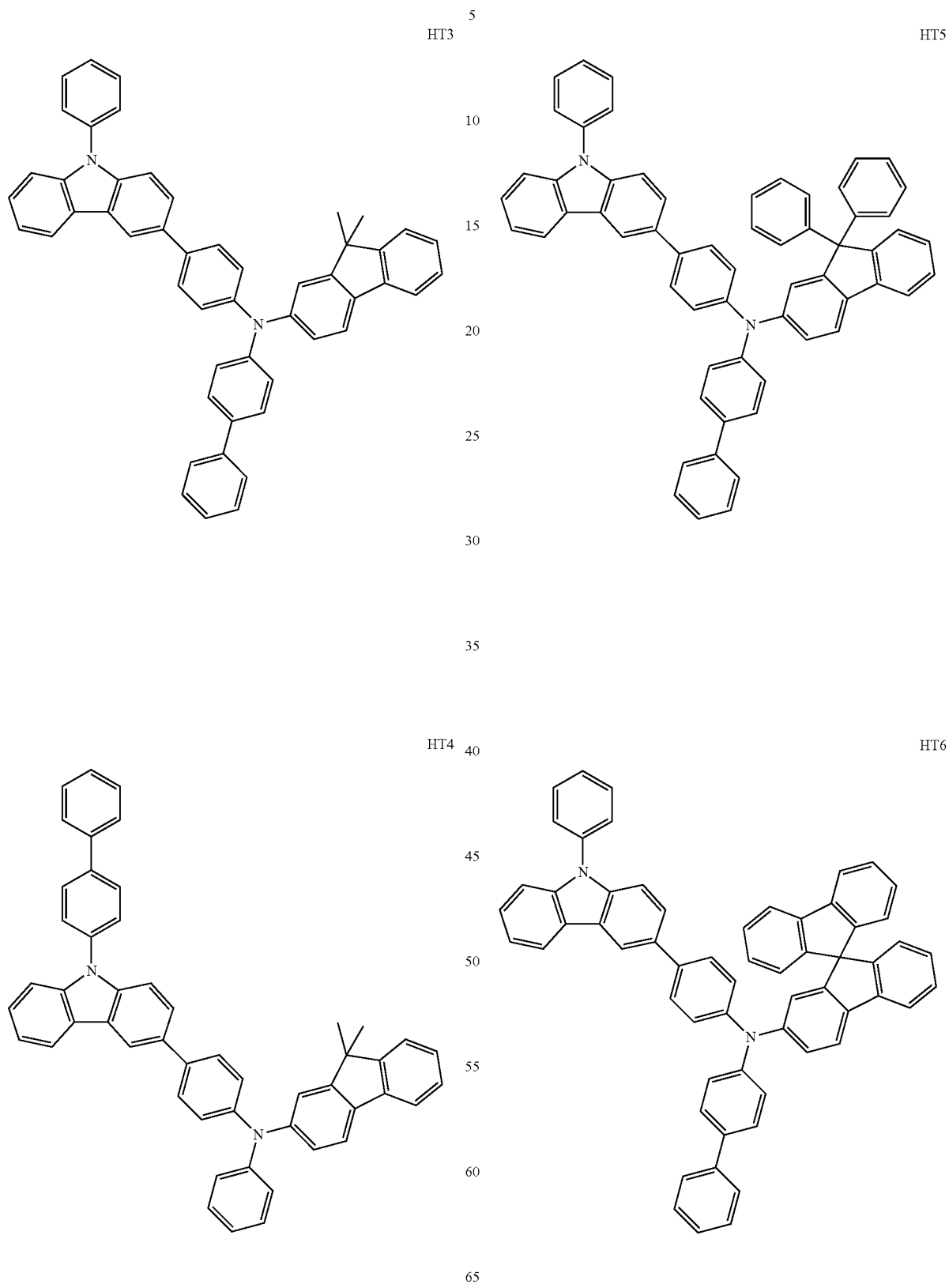

HT7
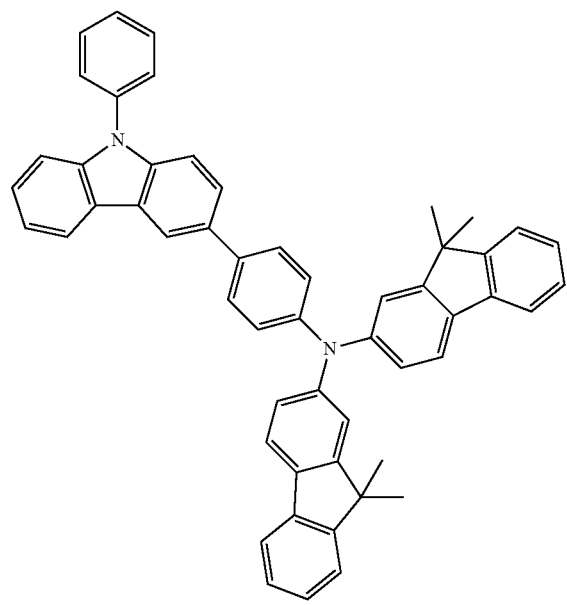
HT8
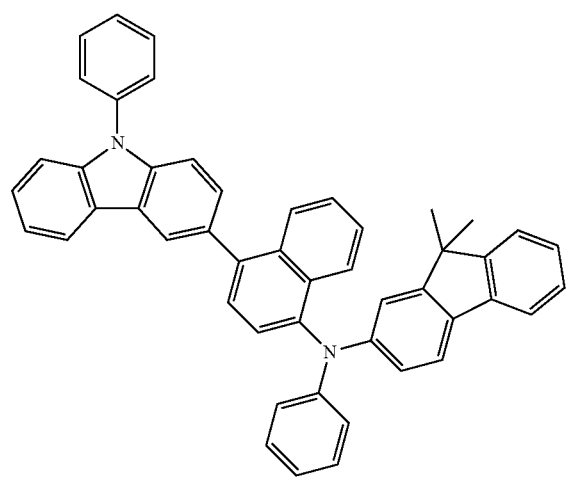
HT9
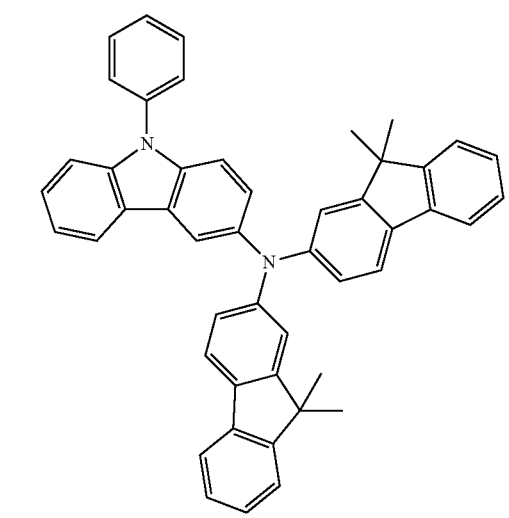
HT10
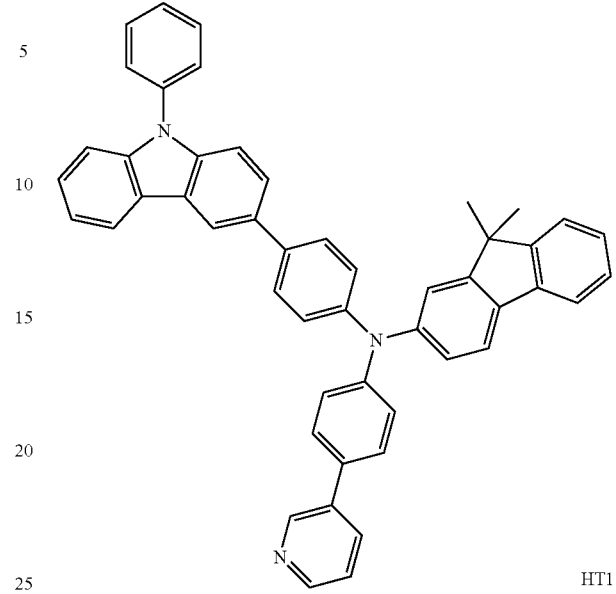
HT11
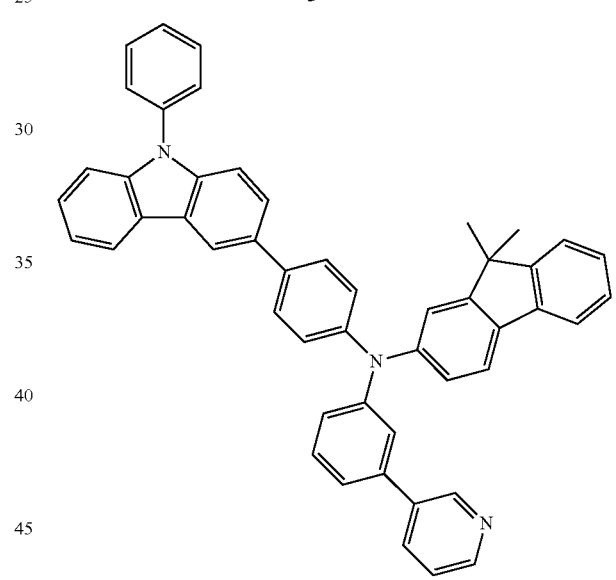
HT12
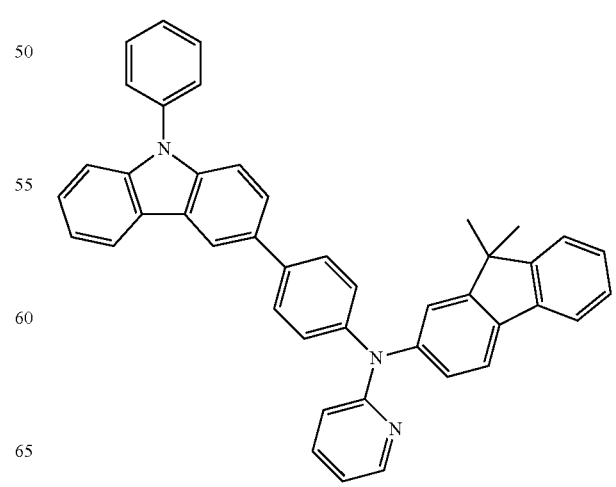

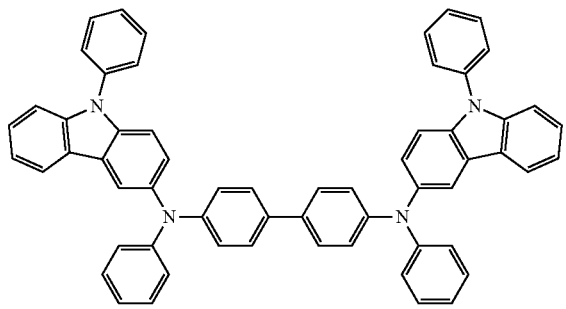
HT13

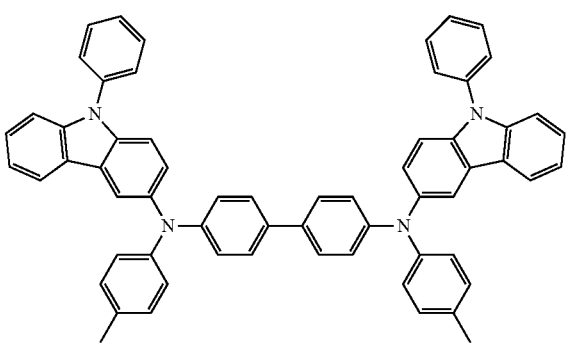
HT14

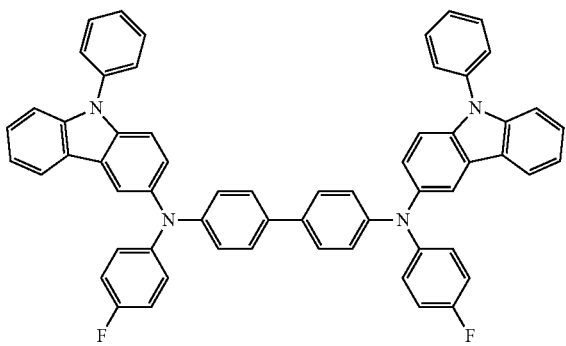
HT15

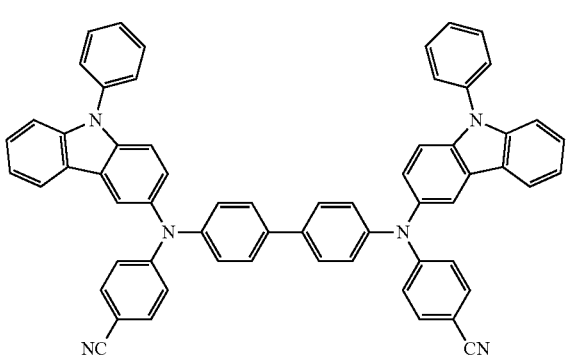
HT16

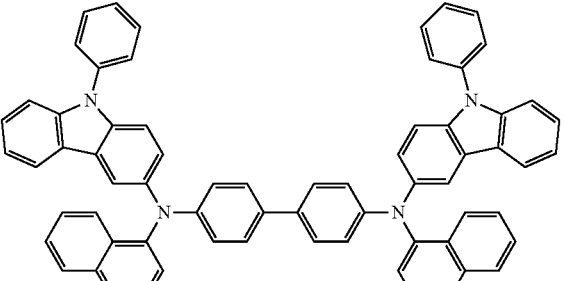
HT17

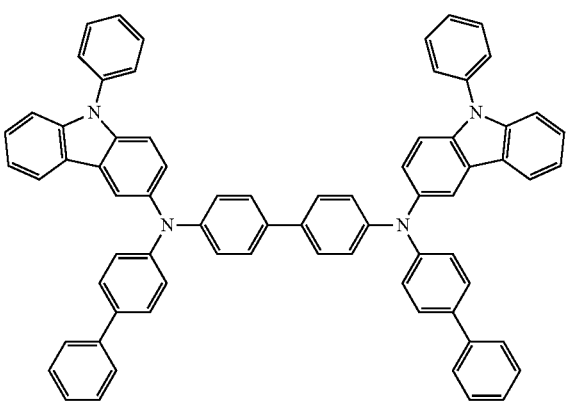
HT18

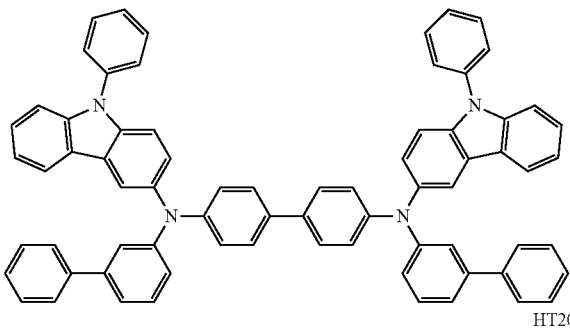
HT19

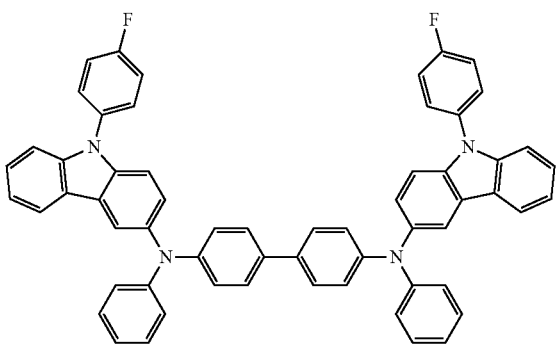
HT20

A thickness of the hole transport region may be in a range of about 100 Å to about 10,000 Å, for example, about 100 Å to about 1,000 Å. When the hole transport region includes the a hole injection layer and a hole transport layer, a thickness of the hole injection layer may be in a range of about 100 Å to about 10,000 Å, for example, about 100 Å to about 1000 Å, a thickness of the hole transport layer may be in a range of about 50 Å to about 2,000 Å, for example, about 100 Å to about 1,500 Å. When the thicknesses of the hole transport region, the hole injection layer, and the hole transport layer are within these ranges, excellent hole transport characteristics may be obtained without a substantial increase in driving voltage.

The hole transport region may further include, in addition to the mentioned materials above, a charge-generating material to improve conductive properties. The charge-generating material may be homogeneously or non-homogeneously dispersed throughout the hole transport region.

The charge-generating material may be, for example, a p-dopant. The p-dopant may be one selected from a quinone derivative, a metal oxide, and a cyano group-containing compound, but is not limited thereto. For example, non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide; and a compound containing a cyano group, such as Compound HT-D1 illustrated below, but they are not limited thereto.

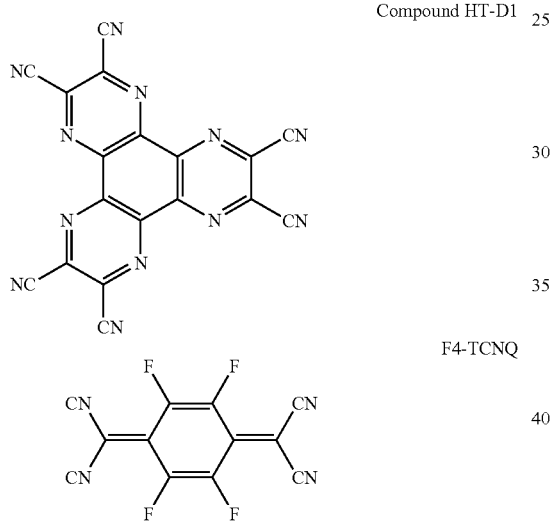

Compound HT-D1

F4-TCNQ

The hole transport region may further include a buffer layer.

The buffer layer may compensate for an optical resonance distance according to a wavelength of light emitted from the emission layer to improve the efficiency of an organic light-emitting device.

An emission layer (EML) may be formed on the hole transport region by using various methods, such as vacuum-deposition, spin coating, casting, or an LB method. When the emission layer is formed by vacuum-deposition or spin coating, vacuum-deposition and coating conditions for the emission layer may be generally similar to the conditions for forming a hole injection layer, though the conditions may vary depending on the compound used.

When the organic light-emitting device is a full color organic light-emitting device, the emission layer may be patterned into a red emission layer, a green emission layer, and a blue emission layer. Alternatively, the emission layer may have a structure in which the red emission layer, the green emission layer, and/or the blue emission layer are layered to emit white light or other various embodiments are possible.

The emission layer may include the condensed cyclic compound represented by Formula 1. The emission layer may further include a dopant. The dopant may include at least one selected from a fluorescent dopant and a phosphorescent dopant.

For example, a host in the emission layer may include the condensed cyclic compound represented by Formula 1.

The dopant in the emission layer may include a fluorescent dopant which emits light according to a fluorescent emission mechanism or a phosphorescent dopant which emits light according to a phosphorescent emission mechanism.

According to an embodiment, the dopant in the emission layer may be a phosphorescent dopant, and the phosphorescent dopant may include an organometallic compound represented by Formula 81:

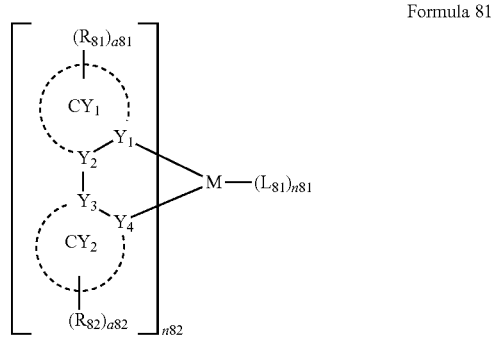

Formula 81 wherein in Formula 81,

M may be iridium (Ir), platinum (Pt), osmium (Os), titanium (Ti), zirconium (Zr), hafnium (Hf), europium (Eu), terbium (Tb), or thulium (Tm);

$Y_1$ to $Y_4$ may be each independently carbon (C) or nitrogen (N);

$Y_1$ and $Y_2$ may be linked to each other via a single bond or a double bond, and $Y_3$ and $Y_4$ are linked to each other via a single bond or a double bond;

$CY_1$ and $CY_2$ may be each independently selected from a benzene, a naphthalene, a fluorene, a spiro-fluorene, an indene, a pyrrole, a thiophene, a furan, an imidazole, a pyrazole, a thiazole, an isothiazole, an oxazole, an isoxazole, a pyridine, a pyrazine, a pyrimidine, a pyridazine, a quinoline, an isoquinoline, a benzoquinoline, a quinoxaline, a quinazoline, a carbazole, a benzoimidazole, a benzofuran, a benzothiophene, an isobenzothiophene, a benzoxazole, an isobenzoxazole, a triazole, a tetrazole, an oxadiazole, a triazine, a dibenzofuran, and a dibenzothiophene, and $CY_1$ and $CY_2$ may be optionally additionally linked to each other via an organic linking group;

$R_{81}$ and $R_{82}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —$SF_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$);

a81 and a82 may be each independently an integer selected from 1 to 5;

n81 may be an integer selected from 0 to 4;

n82 may be an integer selected from 1, 2, and 3;

$L_{81}$ may be a monovalent organic ligand, a divalent organic ligand, or a trivalent organic ligand.

The phosphorescent dopant may include at least one selected from Compounds PD1 to PD78 below, but it is not limited thereto:

PD1
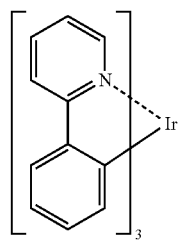

PD2
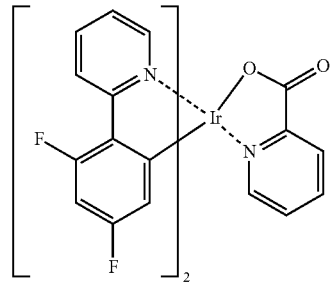

PD3
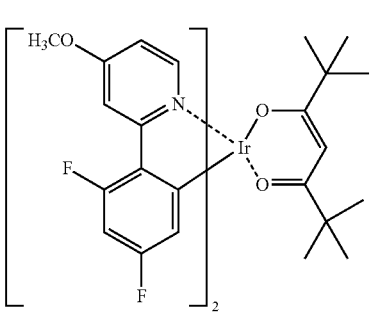

PD4
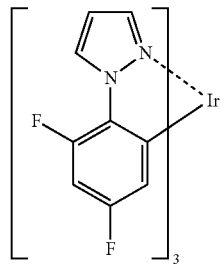

PD5
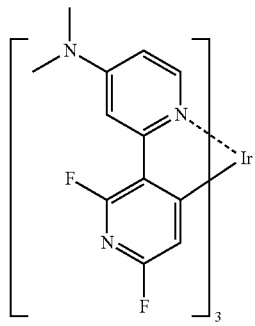

PD6
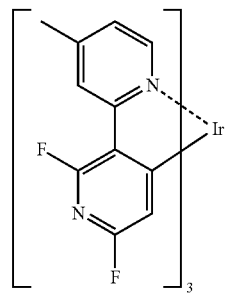

PD7
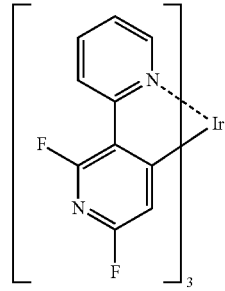

PD8
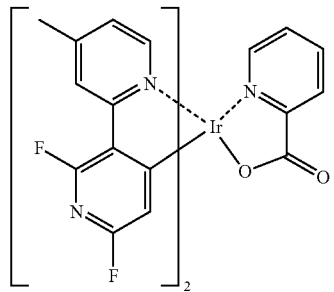

PD9
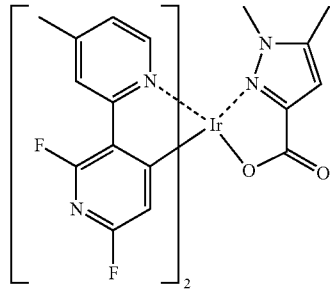

PD10 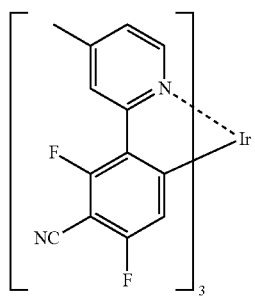
PD11 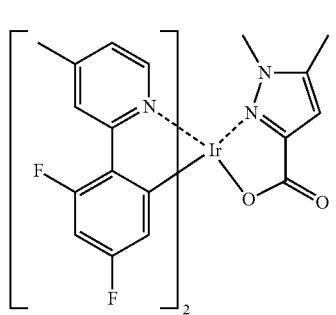
PD12 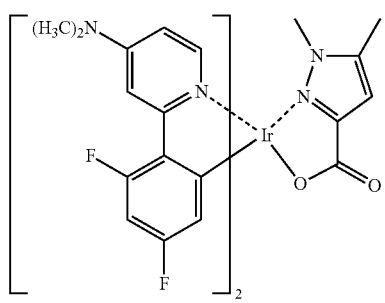
PD13 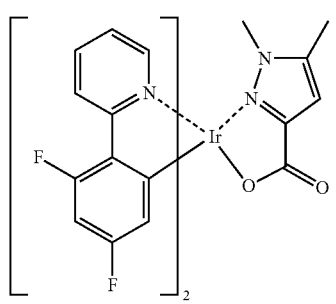
PD14 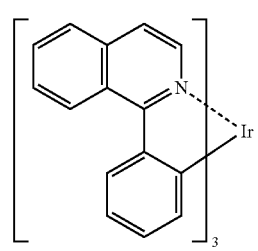
PD15 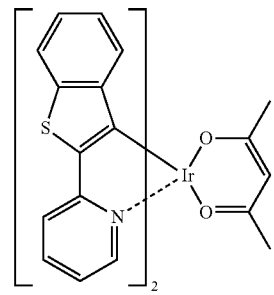
PD16 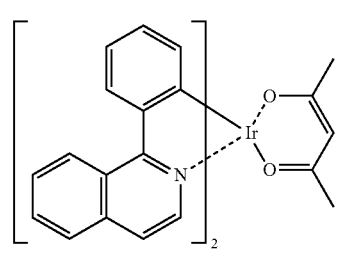
PD17 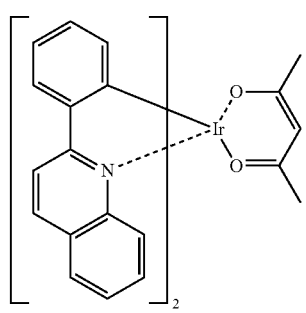
PD18 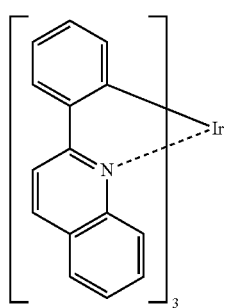
PD19 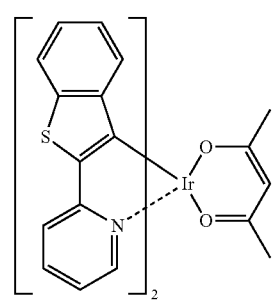

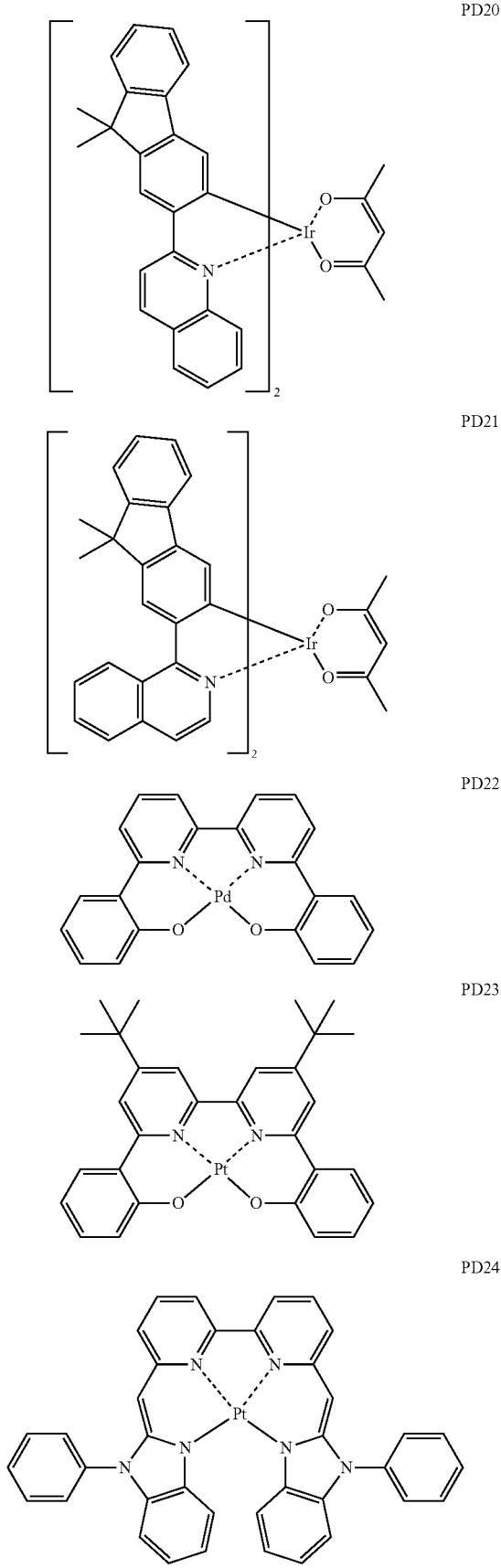

PD31
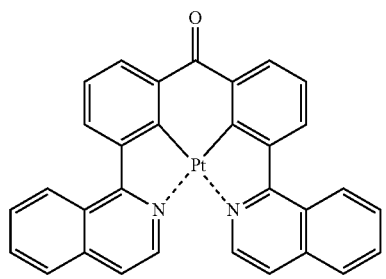
PD36
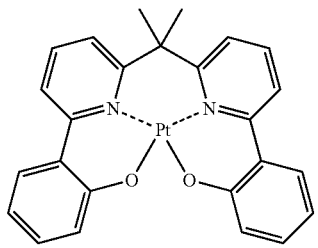
PD32
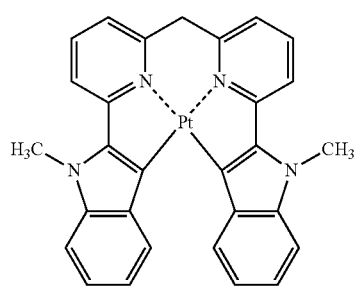
PD37
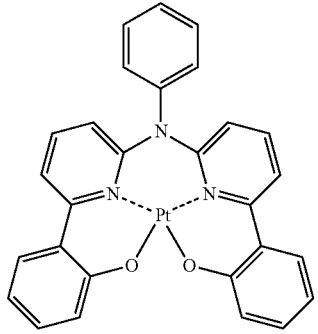
PD33
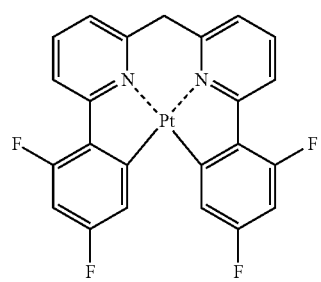
PD38
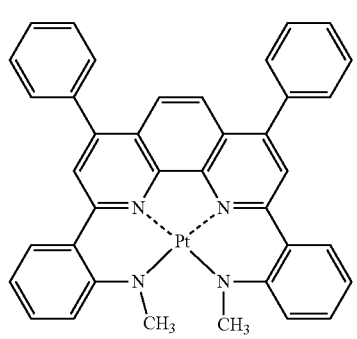
PD34
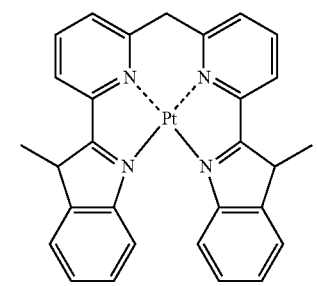
PD39
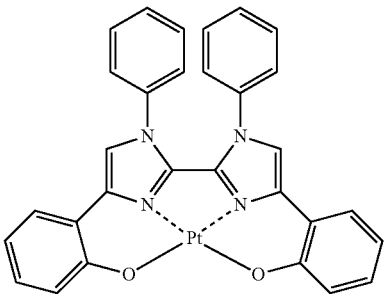
PD35
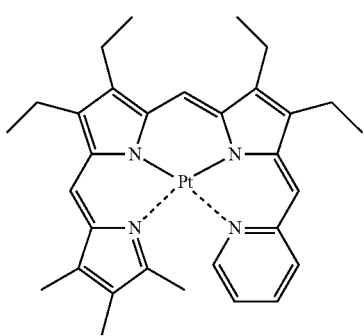
PD40
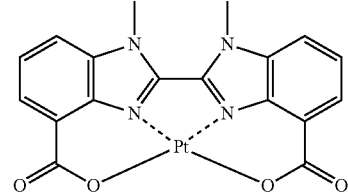
PD41
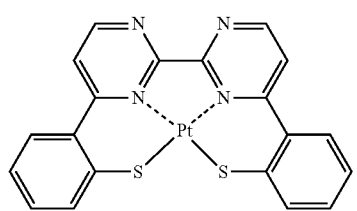

PD42 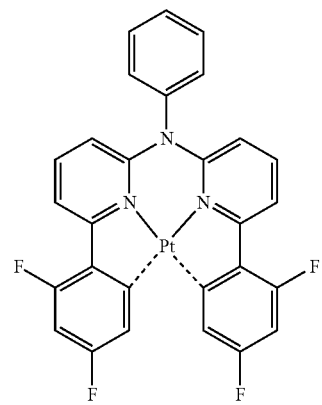
PD43 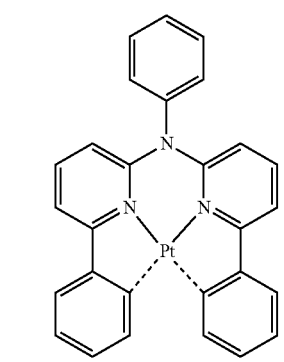
PD44 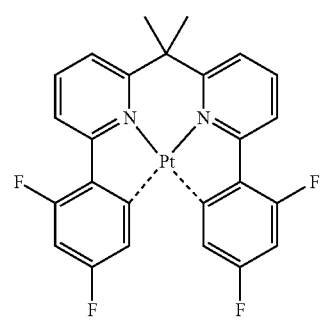
PD45 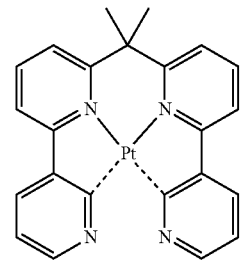
PD46 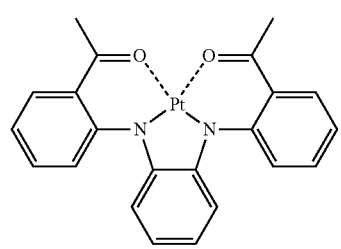
PD47 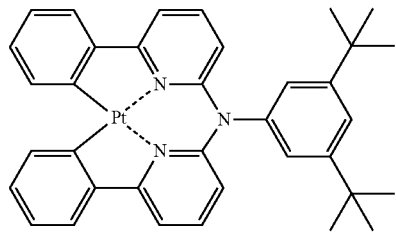
PD48 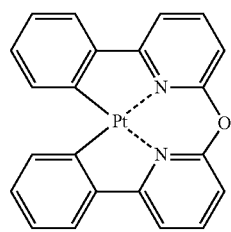
PD49 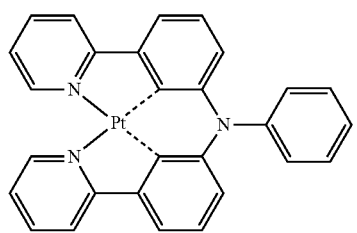
PD50 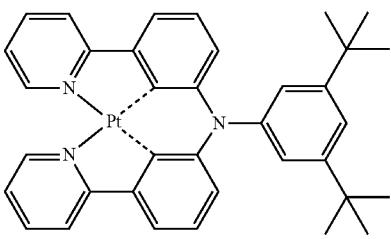
PD51 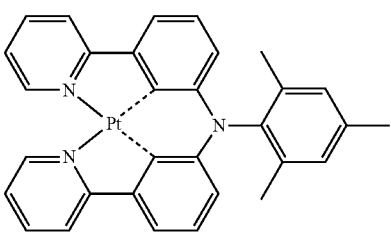
PD52 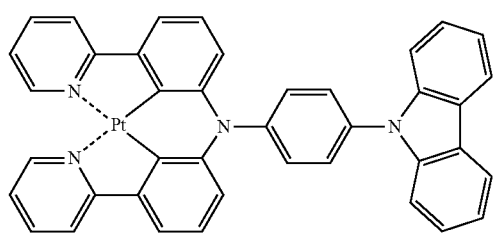

PD53
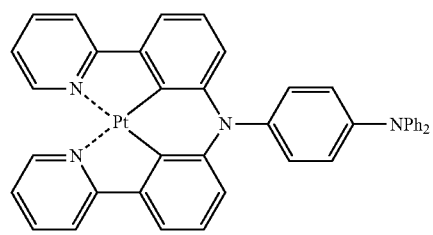
PD54
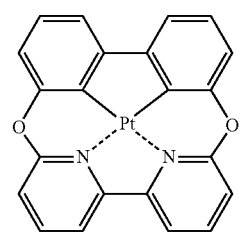
PD55
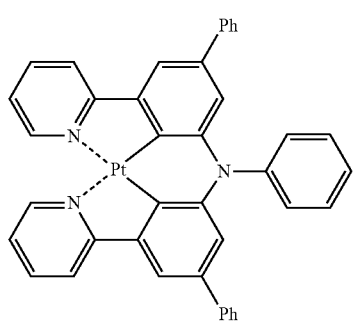
PD56
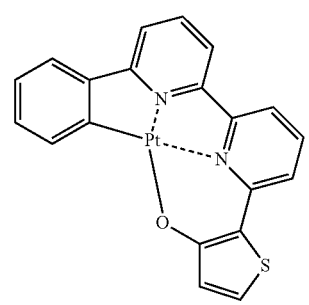
PD57
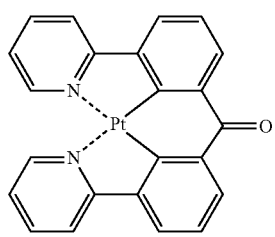
PD58
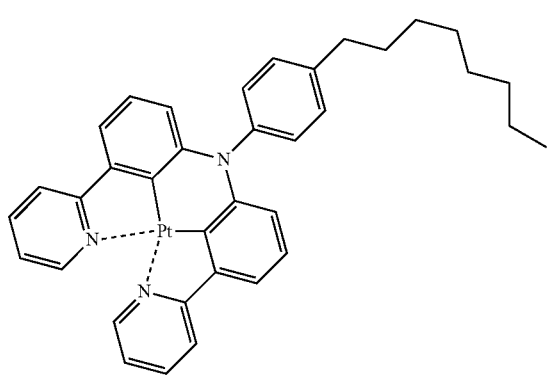
PD59
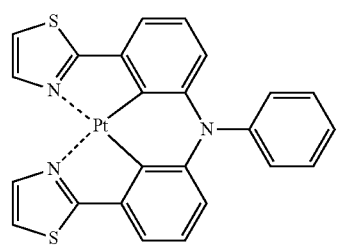
PD60
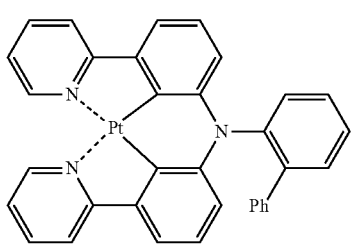
PD61
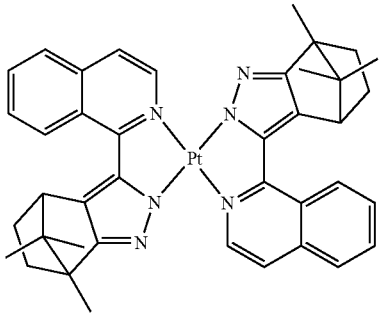
PD62
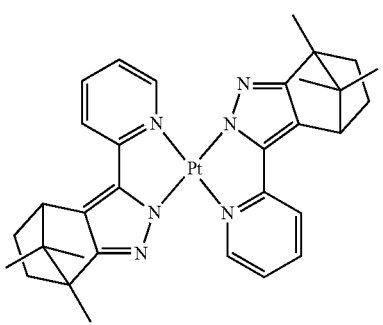

PD63 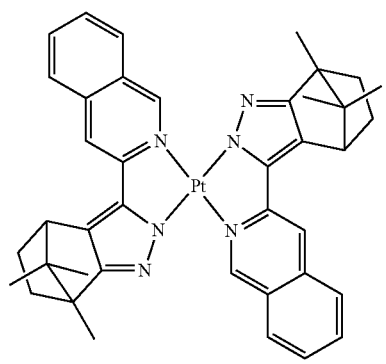
PD64 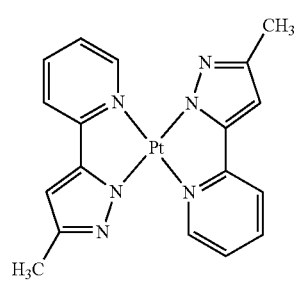
PD65 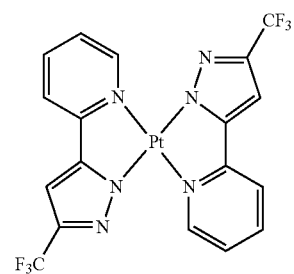
PD66 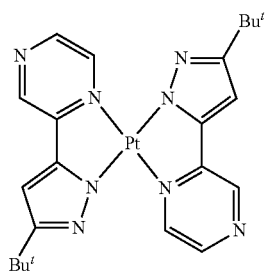
PD67 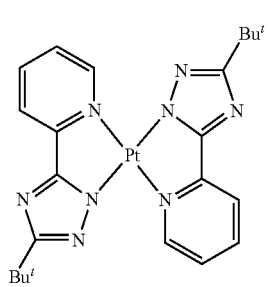
PD68 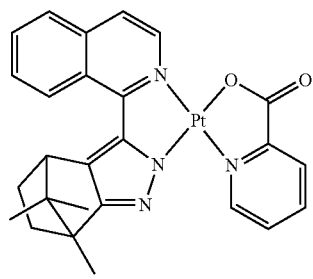
PD69 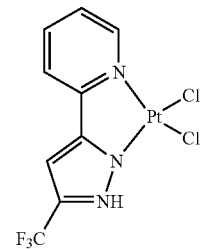
PD70 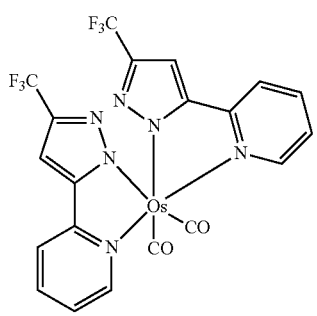
PD71 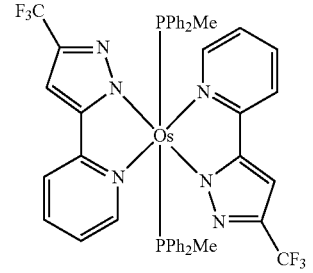
PD72 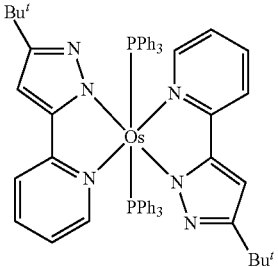

PD73
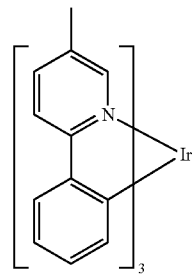
PD74
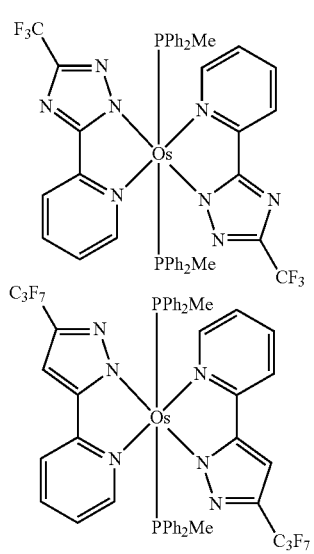
PD75
PD76
PD77
PD78
Alternatively, the phosphorescent dopant may include PtOEP or FIr6 below:
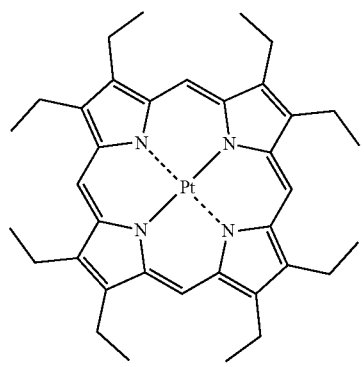
PtOEP
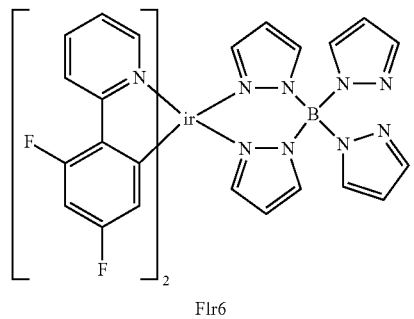
FIr6
The fluorescent dopant may include at least one selected from DPAVBi, BDAVBi, TBPe, DCM, DCJTB, Coumarin 6, and C545T.
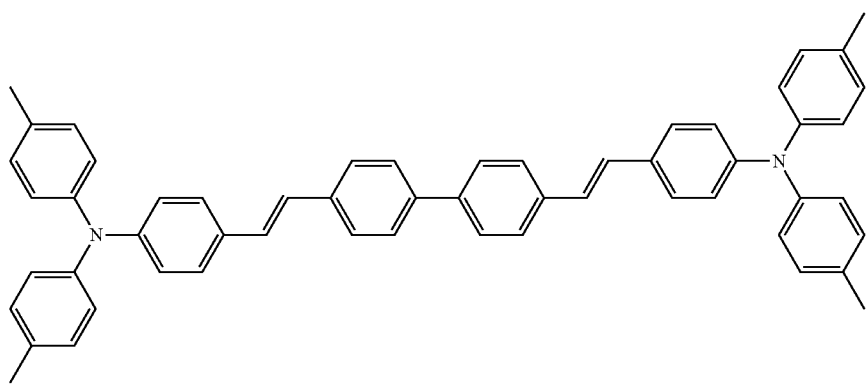
DPAVBi

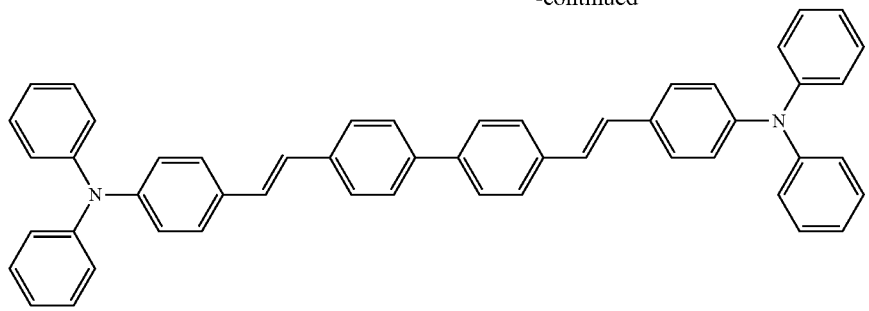

BDAVBi

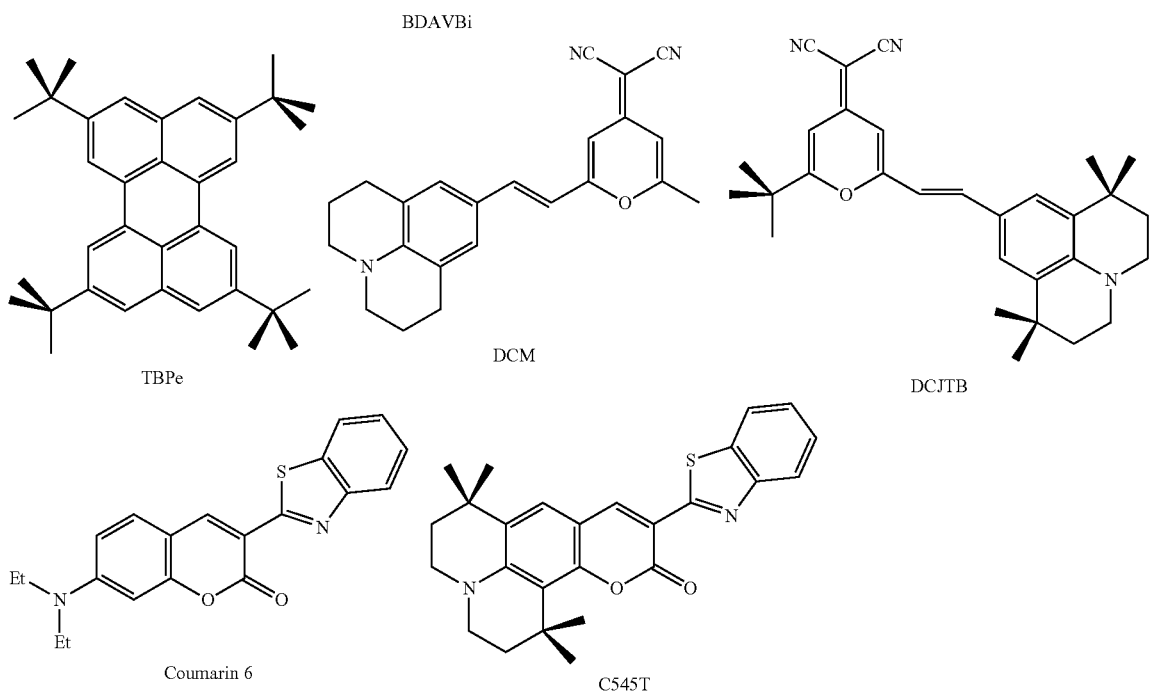

TBPe

DCM

DCJTB

Coumarin 6

C545T

When the emission layer includes the host and the dopant, an amount of the dopant may be selected from in a range of about 0.01 to about 20 parts by weight based on about 100 parts by weight of the host, but the amount is not limited thereto.

A thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer, and an electron injection layer, but is not limited thereto.

For example, the electron transport region may have a structure of a hole blocking layer/an electron transport layer/an electron injection layer or an electron transport layer/an electron injection layer, but it is not limited thereto. The electron transport layer may have a single layer structure or a multi-layer structure including two or more different materials.

The conditions for forming a hole blocking layer, an electron transport layer, and an electron injection layer may be inferred based on the conditions for forming the hole injection layer.

When the electron transport region includes a hole blocking layer, the hole blocking layer may, for example, include at least one selected from BCP, Bphen, and TmPyPB, but it is not limited thereto.

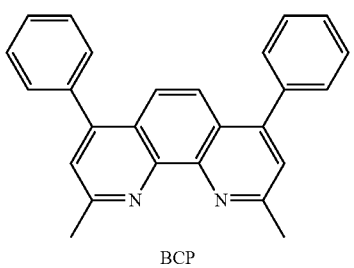

BCP

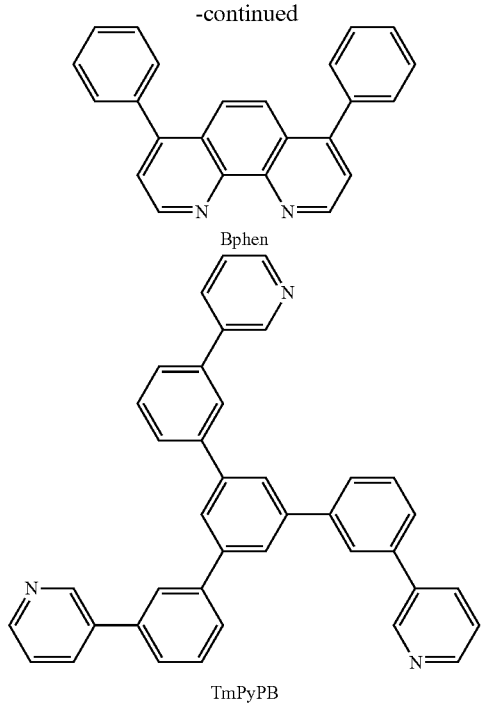

Bphen

TmPyPB

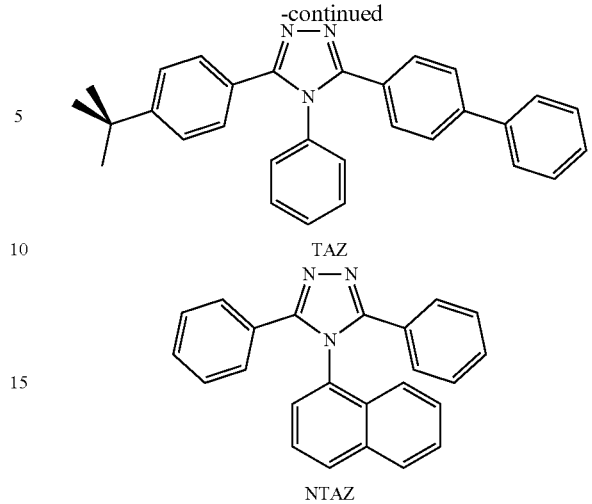

TAZ

NTAZ

Alternatively, the electron transport layer may include at least one selected from Compounds ET1 and ET2, but it is not limited thereto.

A thickness of the hole blocking layer may be in a range of about 20 Å to about 1,000 Å, for example, about 30 Å to about 300 Å. When the thickness of the hole blocking layer is within this range, excellent hole blocking characteristics may be obtained without a substantial increase in driving voltage.

The electron transport layer may further include at least one selected from BCP, Bphen, Alq$_3$, BAlq, TAZ, and NTAZ.

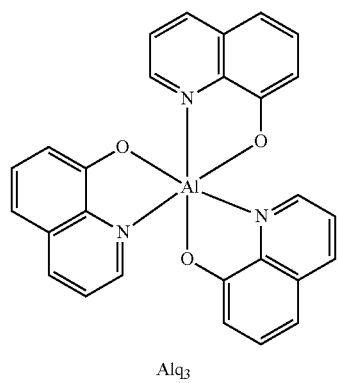

Alq$_3$

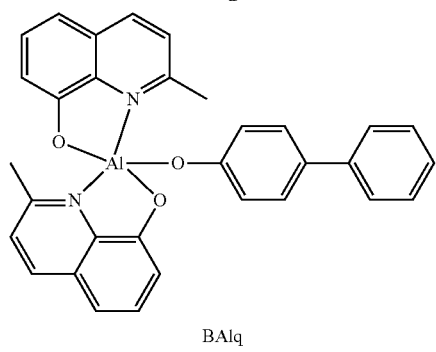

BAlq

ET1

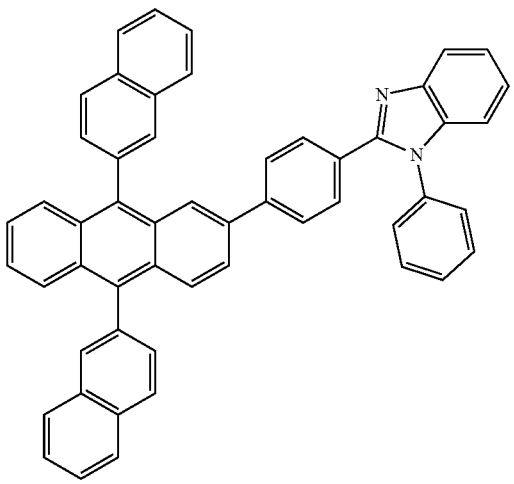

ET2

A thickness of the electron transport layer may be in a range of about 100 Å to about 1,000 Å, for example, about 150 Å to about 500 Å. When the thickness of the electron transport layer is within this range, excellent electron transport characteristics may be obtained without a substantial increase in driving voltage.

The electron transport layer may further include a metal-containing material in addition to the materials described above.

The metal-containing material may include a Li complex. The Li complex may include, for example, Compound ET-D1 (lithium quinolate, LiQ) or ET-D2.

ET-D1

ET-D2

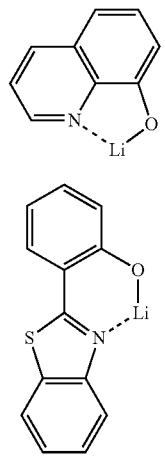

The electron transport region may include an electron injection layer (EIL) that facilitates electron injection from the second electrode 19.

The electron injection layer may include at least one selected from, LiF, NaCl, CsF, Li$_2$O, and BaO.

A thickness of the electron injection layer may be in a range of about 1 Å to about 100 Å, for example, about 3 Å to about 90 Å. When the thickness of the electron injection layer is within this range, excellent electron injection characteristics may be obtained without a substantial increase in driving voltage.

The second electrode 19 is disposed on the organic layer 15. The second electrode 19 may be a cathode. A material for the second electrode 19 may be a material having a relatively low work function, such as a metal, an alloy, an electrically conductive compound, and a mixture thereof. Detailed examples of the material for forming the second electrode 19 are lithium (Li), magnesium (Mg), aluminum (Al), aluminum-lithium (Al—Li), calcium (Ca), magnesium-indium (Mg—In), and magnesium-silver (Mg—Ag). Alternatively, ITO or IZO may be used to form a transmissive second electrode 19 to manufacture a top emission light-emitting device, and such a variation may be possible.

Hereinbefore, the organic light-emitting device has been described with reference to FIG. 1, but it is not limited thereto.

A $C_1$-$C_{60}$ alkyl group as used herein refers to a linear or branched aliphatic hydrocarbon monovalent group having 1 to 60 carbon atoms. Detailed examples thereof are a methyl group, an ethyl group, a propyl group, an isobutyl group, a sec-butyl group, a tert-butyl group, a pentyl group, an iso-amyl group, and a hexyl group. A $C_1$-$C_{60}$ alkylene group as used herein refers to a divalent group having the same structure as the $C_1$-$C_{60}$ alkyl group.

A $C_1$-$C_{60}$ alkoxy group as used herein refers to a monovalent group represented by —OA$_{101}$ (wherein A$_{101}$ is the $C_1$-$C_{60}$ alkyl group). Detailed examples thereof are a methoxy group, an ethoxy group, and an isopropyloxy group.

A $C_2$-$C_{60}$ alkenyl group as used herein refers to a group formed by substituting at least one carbon double bond in the middle or at the terminal of the $C_2$-$C_{60}$ alkyl group. Detailed examples thereof are an ethenyl group, a propenyl group, and a butenyl group. A $C_2$-$C_{60}$ alkenylene group as used herein refers to a divalent group having the same structure as a $C_2$-$C_{60}$ alkenyl group.

A $C_2$-$C_{60}$ alkynyl group as used herein refers to a group formed by substituting at least one carbon triple bond in the middle or at the terminal of the $C_2$-$C_{60}$ alkyl group. Detailed examples thereof are an ethenyl group and a propenyl group. A $C_2$-$C_{60}$ alkynylene group as used herein refers to a divalent group having the same structure as a $C_2$-$C_{60}$ alkynyl group.

A $C_3$-$C_{10}$ cycloalkyl group as used herein refers to a monovalent monocyclic saturated hydrocarbon group including 3 to 10 carbon atoms. Detailed examples thereof are a cyclopropyl group, a cyclobutyl group, a cyclopentyl group, a cyclohexyl group, and a cycloheptyl group. A $C_3$-$C_{10}$ cycloalkylene group as used herein refers to a divalent group having the same structure as a $C_3$-$C_{10}$ cycloalkyl group.

A $C_1$-$C_{10}$ heterocycloalkyl group as used herein refers to a monovalent monocyclic group including at least one hetero atom selected from N, O, P, and S as a ring-forming atom and 1 to 10 carbon atoms. Detailed examples thereof are a tetrahydrofuranyl group and a tetrahydrothiophenyl group. A $C_1$-$C_{10}$ heterocycloalkylene group as used herein refers to a divalent group having the same structure as a $C_1$-$C_{10}$ heterocycloalkyl group.

A $C_3$-$C_{10}$ cycloalkenyl group as used herein refers to a monovalent monocyclic group including 3 to 10 carbon atoms and at least one double bond in the ring thereof, which is not aromatic. Detailed examples thereof are such as a cyclopentenyl group, a cyclohexenyl group, or a cycloheptenyl group. A $C_3$-$C_{10}$ cycloalkenylene group as used herein refers to a divalent group having the same structure as a $C_3$-$C_{10}$ cycloalkenyl group.

A $C_1$-$C_{10}$ heterocycloalkenyl group as used herein refers to a monovalent monocyclic group including at least one hetero atom selected from N, O, P, and S as a ring-forming atom, 1 to 10 carbon atoms, and at least one double bond in its ring. Detailed examples of the $C_2$-$C_{10}$ heterocycloalkenyl group are a 2,3-dihydrofuranyl group and a 2,3-dihydrothiophenyl group. A $C_1$-$C_{10}$ heterocycloalkenylene group as used herein refers to a divalent group having the same structure as a $C_1$-$C_{10}$ heterocycloalkenyl group.

A $C_6$-$C_{60}$ aryl group as used herein refers to a monovalent group having a carbocyclic aromatic system having 6 to 60 carbon atoms, and a $C_6$-$C_{60}$ arylene group as used herein refers to a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

A $C_1$-$C_{60}$ heteroaryl group as used herein refers to a monovalent group having a carbocyclic aromatic system having at least one hetero atom selected from N, O, P, and S as a ring-forming atom and 1 to 60 carbon atoms. A $C_1$-$C_{60}$ heteroarylene group as used herein refers to a divalent group having a carbocyclic aromatic system having at least one hetero atom selected from N, O, P, and S as a ring-forming atom and 1 to 60 carbon atoms. Detailed examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include a plurality of rings, the plurality of rings may be fused to each other.

A $C_6$-$C_{60}$ aryloxy group as used herein indicates —$OA_{102}$ (wherein $A_{102}$ is the $C_6$-$C_{60}$ aryl group), and a $C_6$-$C_{60}$ arylthio group as used herein indicates —$SA_{103}$ (wherein $A_{103}$ is the $C_6$-$C_{60}$ aryl group).

A monovalent non-aromatic condensed polycyclic group as used herein refers to a monovalent group that has two or more rings condensed to each other, only carbon atoms (for example, the number of carbon atoms may be in a range of 8 to 60) as ring forming atoms, wherein the molecular structure as a whole is non-aromatic. Detailed examples of the non-aromatic condensed polycyclic group include a fluorenyl group (three rings of the fluorenyl group are condensed with each other). A divalent non-aromatic condensed polycyclic group as used herein refers to a divalent group having the same structure as the monovalent non-aromatic condensed polycyclic group.

A monovalent non-aromatic condensed hetero-polycyclic group used herein refers to a monovalent group that has a plurality of rings condensed with each other, has a hetero atom selected from N, O, P, and S, other than carbon atoms (for example, the number of carbon atoms may be in a range of 1 to 60), as ring-forming atoms, wherein the molecular structure as a whole is non-aromatic. Detailed example of the monovalent non-aromatic condensed heteropolycyclic group includes a carbazolyl group (three rings of the carbazolyl group are condensed with each other). A divalent non-aromatic condensed hetero-polycyclic group as used herein refers to a divalent group having the same structure as the monovalent non-aromatic condensed hetero-polycyclic group.

A biphenyl group used herein refers to a phenyl group substituted with at least one phenyl group.

Hereinafter, a compound and an organic light-emitting device according to an embodiment will be described in detail with reference to Synthesis Examples and Examples, however, the inventive concept is not limited thereto. The wording "B was used instead of A" used in describing Synthesis Examples means that an amount of B used was identical to an amount of A used based on molar equivalence.

EXAMPLE

Synthesis Example 1: Synthesis of Compound 2

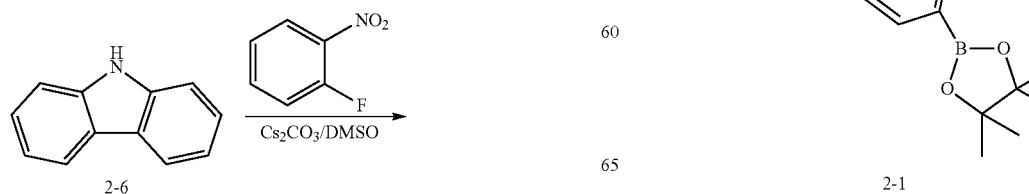

2-6

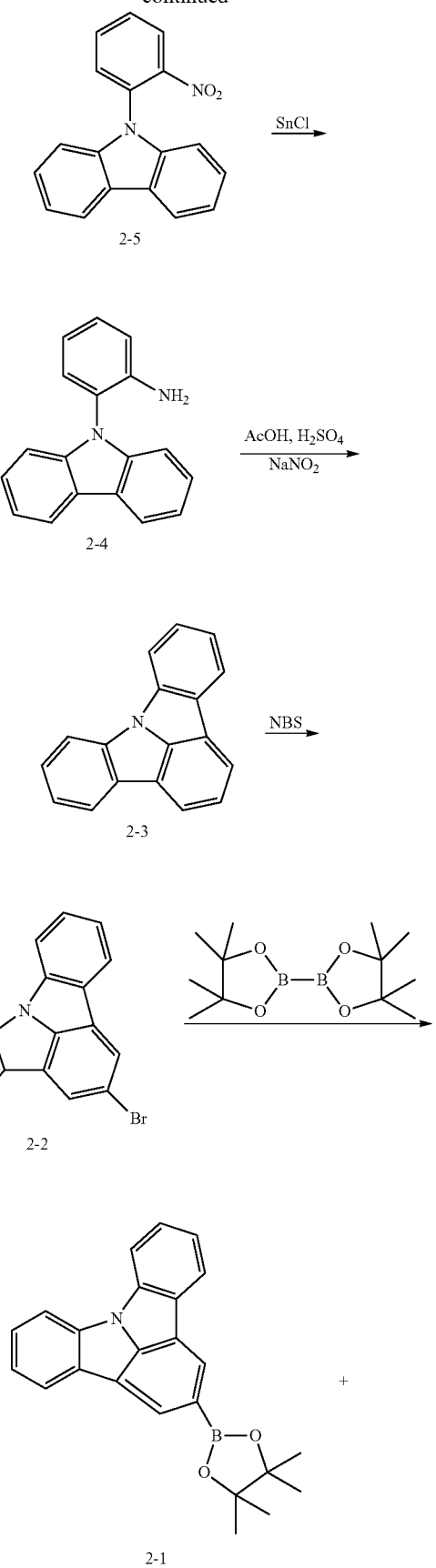

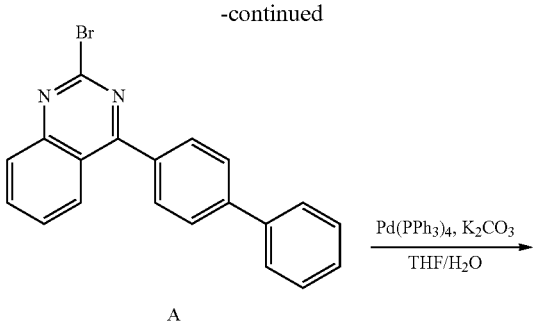

A

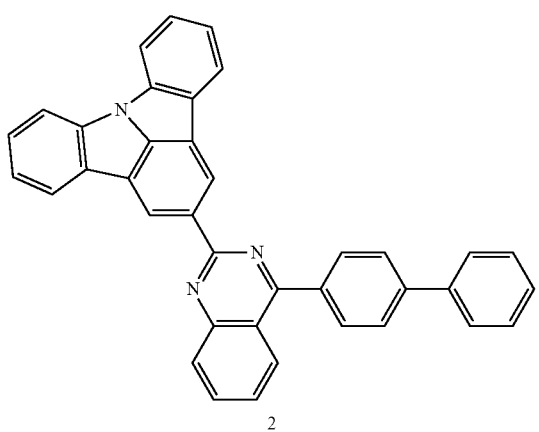

2

Synthesis of Intermediate 2-5

10 grams (g) (59.8 millimoles (mmol)) of Intermediate 2-6 and 8.44 g (59.8 mmol) of Intermediate 2-6(1) were dissolved in 200 mL of dimethylsulfoxide (DMSO). 23.4 g (71.8 mmol) of $Cs_2CO_3$ was added thereto, and the mixture was stirred for about 15 hours. 500 mL of water was added to the mixture. Thereafter, the mixture was filtered to isolate a solid. The isolated solid was mixed with 300 mL of methylene chloride, and 300 mL of water was added thereto in order to extract an organic layer. The organic layer organic layer was dried using magnesium sulfate ($MgSO_4$), and a solvent was removed by evaporation. The residue was separated and purified by a silica gel chromatography to obtain 12.93 g of Intermediate 2-5 (yield: 75%). The compound thus obtained was confirmed by using liquid chromatography-mass spectrometry (LC-MS).

$C_{18}H_{12}N_2O_2$: M+ 288.09.

Synthesis of Intermediate 2-4

10 g (34.7 mmol) of Intermediate 2-5 was added to 25.16 g (111 mmol) of $SnCl_2.2H_2O$ in ethanol (EtOH) and was stirred for 8 hours while heating to maintain 70° C. After the reaction had been completed, the result was allowed to cool to room temperature. The result, which was concentrated, was added to 300 mL of methylene chloride and 300 mL of $NaHCO_3$ (aq) to extract an organic layer. The organic layer was dried using $MgSO_4$, and a solvent was removed by evaporation. The residue was separated and purified by a silica gel chromatography to obtain 6.27 g of Intermediate 2-4 (yield: 70%). The compound thus obtained was confirmed by using LC-MS.

$C_{18}H_{14}N_2$: M+ 258.12

Synthesis of Intermediate 2-3

6 g (23.23 mmol) of Intermediate 2-4, 60 mL of acetic acid, and 5 mL of conc. $H_2SO_4$ were mixed together, placed in an ice bath, and heated to 10° C. A mixture of 150 mL of water and 1.6 g (1 eq) of $NaNO_2$ was added dropwise thereto for 20 minutes, and the resulting mixture was stirred for 10 minutes. The result, which was obtained, was heated to 130° C., and stirred for 20 minutes. After the reaction had been completed, the result was allowed to cool to room temperature. 300 mL of water was added thereto. Thereafter, a precipitated solid was obtained by filtration. The precipitated solid was separated and purified by a silica gel chromatography to obtain 4.03 g of Intermediate 2-3 (yield: 72%). The compound thus obtained was confirmed by using LC-MS.

$C_{18}H_{11}N$: M+ 241.09

Synthesis of Intermediate 2-2

3 g (12.43 mmol) of Intermediate 2-3 and 2.21 g (12.43 mmol) of N-bromosuccinimide (NBS) were dissolved in 100 mL of methylene chloride and stirred for 15 hours at room temperature. After the reaction had been completed, the result was allowed to come to room temperature. 200 mL of methylene chloride and 200 mL of water were added dropwise thereto in order to extract an organic layer. The extracted organic layer was dried using $MgSO_4$, and a solvent was removed by evaporation. The residue was separated and purified by a silica gel chromatography to obtain 2.03 g of Intermediate 2-2 (yield: 51%). The compound thus obtained was confirmed by using LC-MS.

$C_{18}H_{10}BrN$: M+ 319.00

Synthesis of Intermediate 2-1

2 g (6.25 mmol) of Intermediate 2-2, 2.4 g (9.37 mmol) of bis(pinacolato)diboron, 1.84 g (18.74 mmol) of potassium acetate, and 0.26 g (0.37 mmol) of $Pd(PPh_3)_2Cl_2$ were dissolved in 30 mL of tetrahydrofuran (THF), and stirred under reflux at 80° C. for 8 hours. The result was allowed to come to room temperature. The organic layer was extracted by using 200 mL of methylene chloride and 200 mL of water. The extracted organic layer was dried using $MgSO_4$. The solvent was removed by evaporation. The residue was separated and purified by a silica gel chromatography to obtain 1.8 g of Intermediate 2-1 (yield: 79%). The compound thus obtained was confirmed by using LC-MS.

$C_{24}H_{22}BNO_2$: M+ 367.17

Synthesis of Compound 2

1.8 g (4.9 mmol) of Intermediate 2-1, 1.8 g (4.9 mmol) of Intermediate A (4-([1,1'-biphenyl]-4-yl)-2-bromoquinazoline), 1.96 g (12.25 mmol) of $K_2CO_3$, and 0.4 g (0.34 mmol) of $Pd(PPh_3)_4$ were dissolved in 30 mL of THF and 15 mL of $H_2O$, and the mixture was stirred under reflux at 100° C. for about 16 hours. After the reaction had been completed, the result was washed with methylene chloride and toluene and filtered, thereby isolating a solid. The isolated solid was dissolved in dichlorobenzene (DCB) by reflux. The residue was allowed to be filtered by a silica gel chromatography at a high temperature to remove palladium (Pd), thereby obtaining 1.7 g of Compound 2 (yield: 68%). The compound thus obtained was confirmed by using LC-MS.

$C_{38}H_{23}N_3$: M+ 521.19

$^1$H NMR (CDCl$_3$, 300 MHz) δ(ppm) 8.30 (d, 2H), 8.19 (d, 2H), 8.13 (d, 1H), 7.85-7.75 (m, 6H), 7.58-7.40 (m, 10H), 7.20 (t, 2H)

Synthesis Example 2: Synthesis of Compound 5

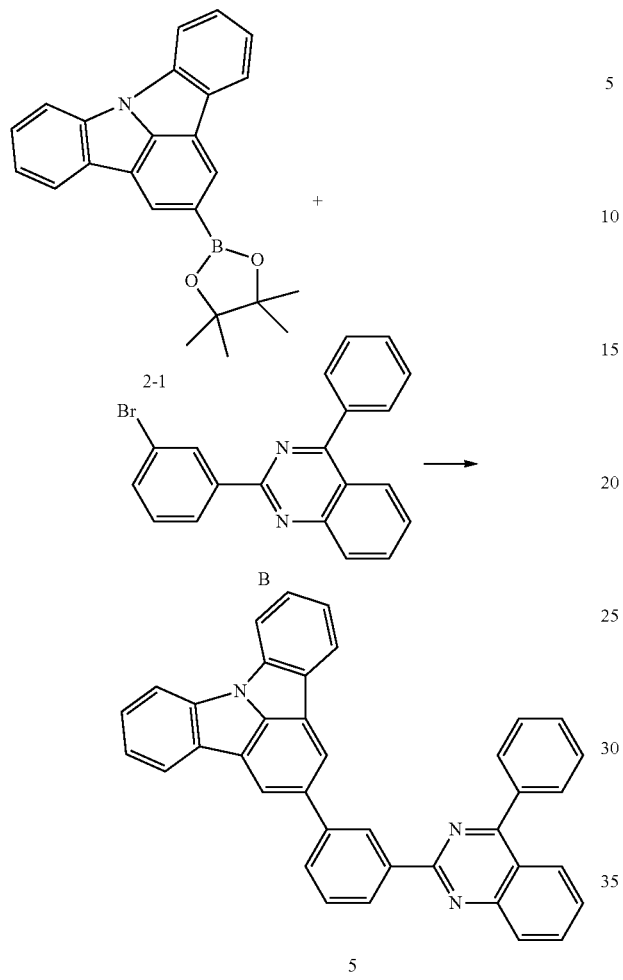

Compound 5 (yield: 62%) was obtained in the same manner as in Synthesis Example 1 except that Intermediate B was used instead of Intermediate A in synthesizing Compound 2. The compound thus obtained was confirmed by using LC-MS and nuclear magnetic resonance (NMR).

$C_{38}H_{23}N_3$: M+ 521.19

$^1$H NMR (CDCl$_3$, 300 MHz) δ(ppm) 8.38 (d, 1H), 8.19 (d, 2H), 8.13 (d, 1H), 7.94 (s, 1H), 7.84-7.50 (m, 16H), 7.20 (t, 2H)

Synthesis Example 3: Synthesis of Compound 9

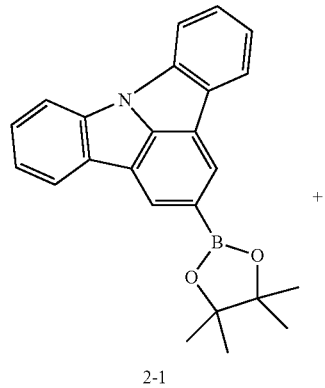

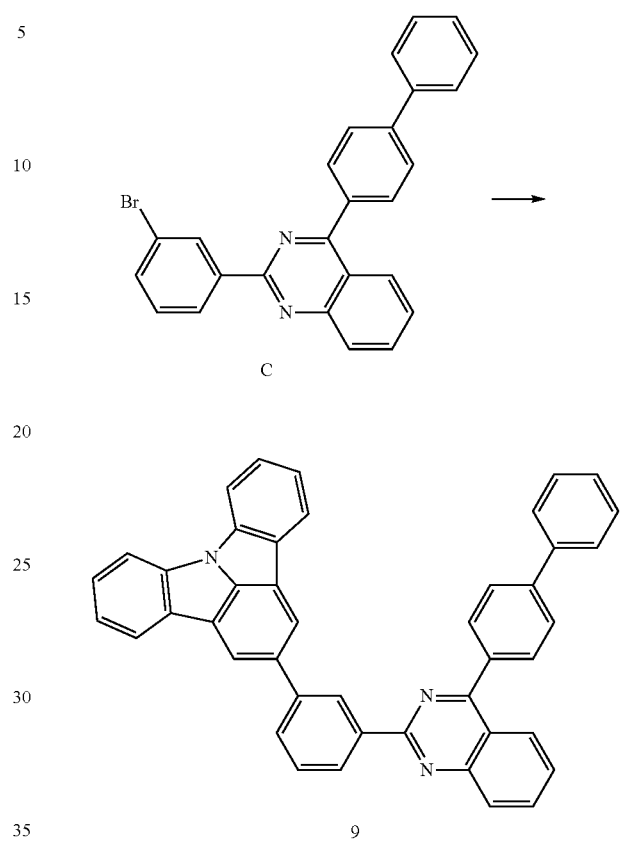

Compound 9 (yield: 70%) was obtained in the same manner as in Synthesis Example 1 except that Intermediate C was used instead of Intermediate A in synthesizing Compound 2. The compound thus obtained was confirmed by using LC-MS and NMR.

$C_{44}H_{27}N_3$: M+ 597.22

$^1$H NMR (CDCl$_3$, 300 MHz) δ(ppm) 8.38 (d, 1H), 8.30 (d, 2H), 8.19 (d, 2H), 8.13 (d, 1H), 7.94 (s, 1H), 7.84-7.41 (m, 18H), 7.20 (t, 2H)

Synthesis Example 4: Synthesis of Compound 35

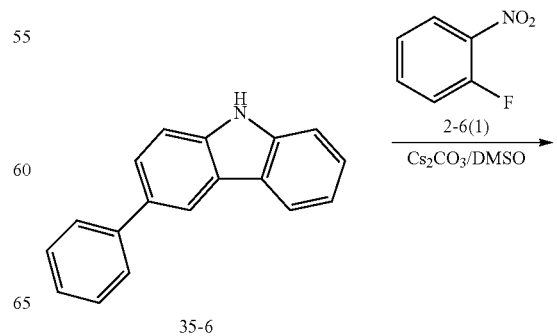

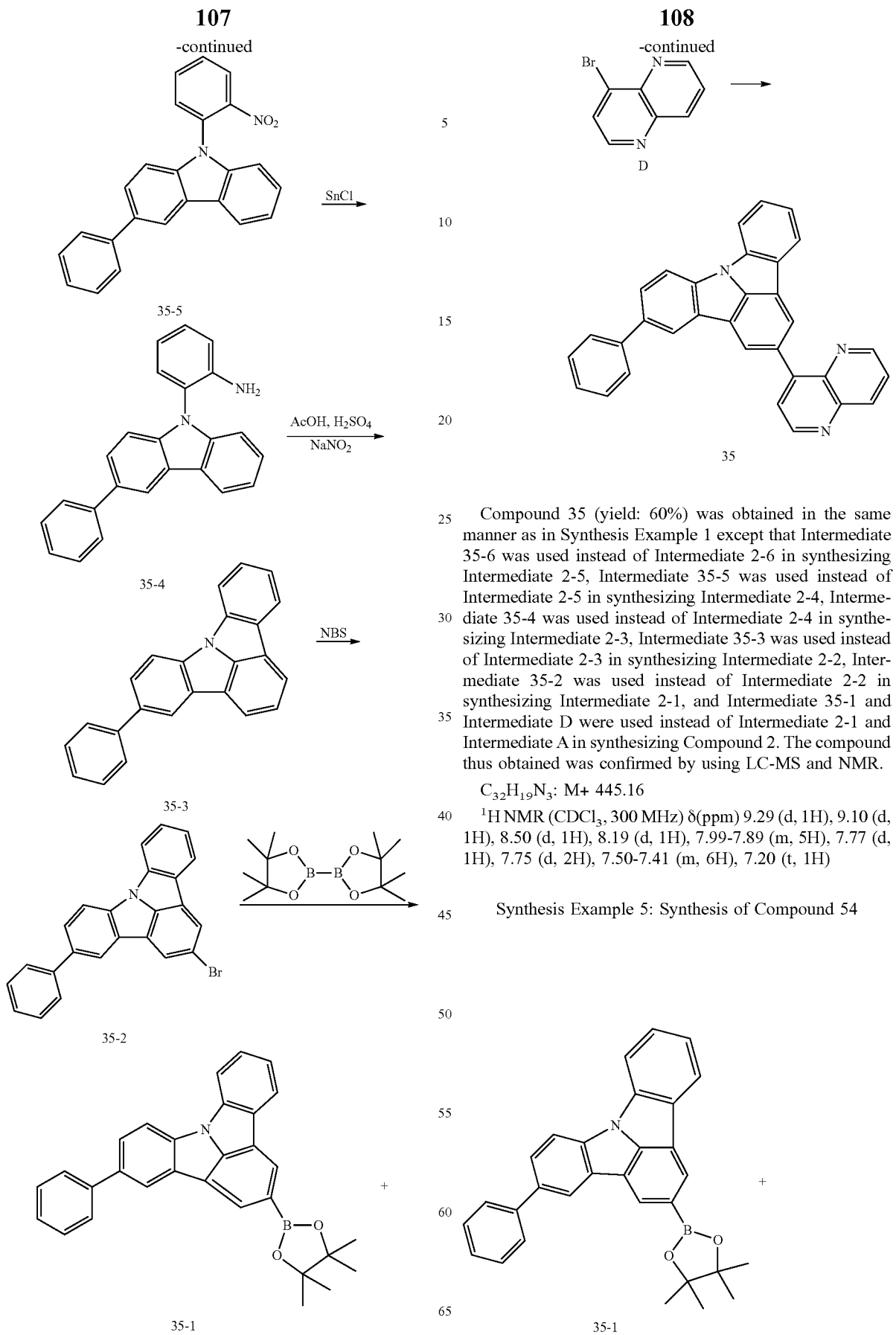

Compound 35 (yield: 60%) was obtained in the same manner as in Synthesis Example 1 except that Intermediate 35-6 was used instead of Intermediate 2-6 in synthesizing Intermediate 2-5, Intermediate 35-5 was used instead of Intermediate 2-5 in synthesizing Intermediate 2-4, Intermediate 35-4 was used instead of Intermediate 2-4 in synthesizing Intermediate 2-3, Intermediate 35-3 was used instead of Intermediate 2-3 in synthesizing Intermediate 2-2, Intermediate 35-2 was used instead of Intermediate 2-2 in synthesizing Intermediate 2-1, and Intermediate 35-1 and Intermediate D were used instead of Intermediate 2-1 and Intermediate A in synthesizing Compound 2. The compound thus obtained was confirmed by using LC-MS and NMR.

$C_{32}H_{19}N_3$: M+ 445.16

$^1$H NMR (CDCl$_3$, 300 MHz) δ(ppm) 9.29 (d, 1H), 9.10 (d, 1H), 8.50 (d, 1H), 8.19 (d, 1H), 7.99-7.89 (m, 5H), 7.77 (d, 1H), 7.75 (d, 2H), 7.50-7.41 (m, 6H), 7.20 (t, 1H)

Synthesis Example 5: Synthesis of Compound 54

-continued

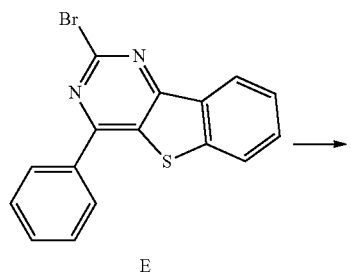

E

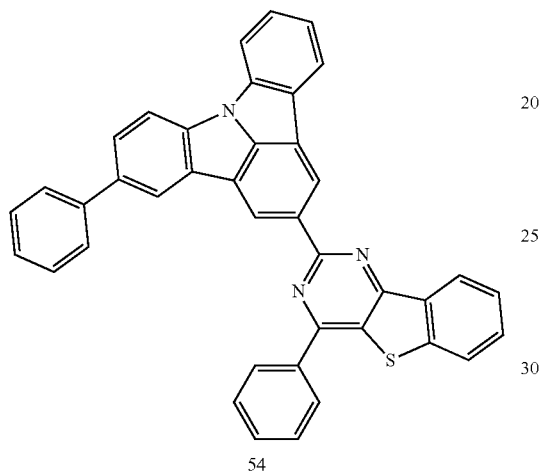

54

Compound 54 (yield: 61%) was obtained in the same manner as in Synthesis Example 1 except that Intermediate 35-1 and Intermediate E were used instead of Intermediate 2-1 and Intermediate A, respectively, in synthesizing Compound 2. The compound thus obtained was confirmed by using LC-MS and NMR.

$C_{40}H_{23}N_3S$: M+ 577.16

$^1$H NMR (CDCl$_3$, 300 MHz) δ(ppm) 8.19 (d, 1H), 8.05 (d, 1H), 7.99 (d, 1H), 7.93 (d, 1H), 7.89 (s, 2H), 7.84 (d, 2H), 7.77-7.75 (m, 3H), 7.58-7.41 (m, 11H), 7.20 (t, 1H)

Synthesis Example 6: Synthesis of Compound 65

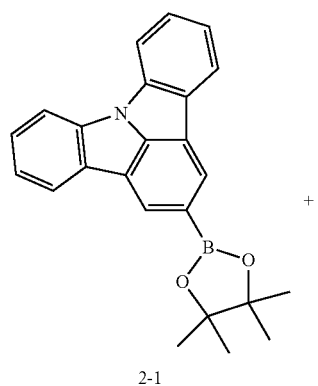

2-1

-continued

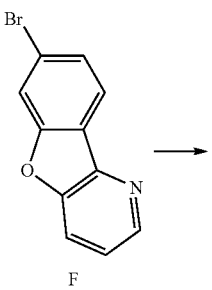

F

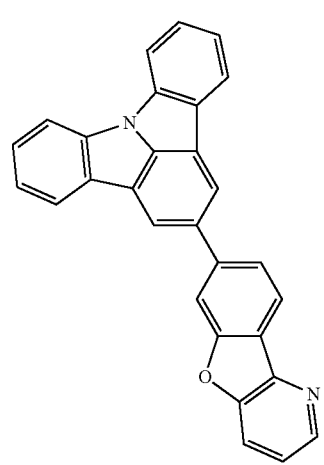

65

Compound 65 (yield: 65%) was obtained in the same manner as in Synthesis Example 1 except that Intermediate F was used instead of Intermediate A in synthesizing Compound 2. The compound thus obtained was confirmed by using LC-MS and NMR.

$C_{29}H_{16}N_2O$: M+ 408.13

$^1$H NMR (CDCl$_3$, 300 MHz) δ(ppm) 8.43 (d, 1H), 8.19 (d, 2H), 8.03 (d, 1H), 7.82 (d, 1H), 7.76 (s, 1H), 7.65-7.50 (m, 6H), 7.33 (d, 1H), 7.23-7.20 (m, 3H)

Synthesis Example 7: Synthesis of Compound 67

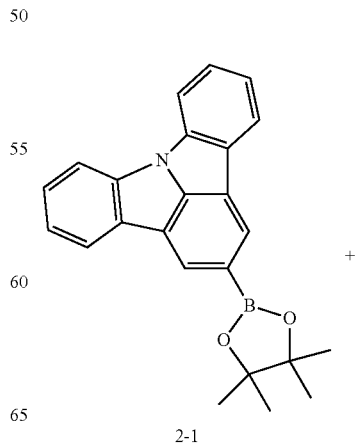

2-1

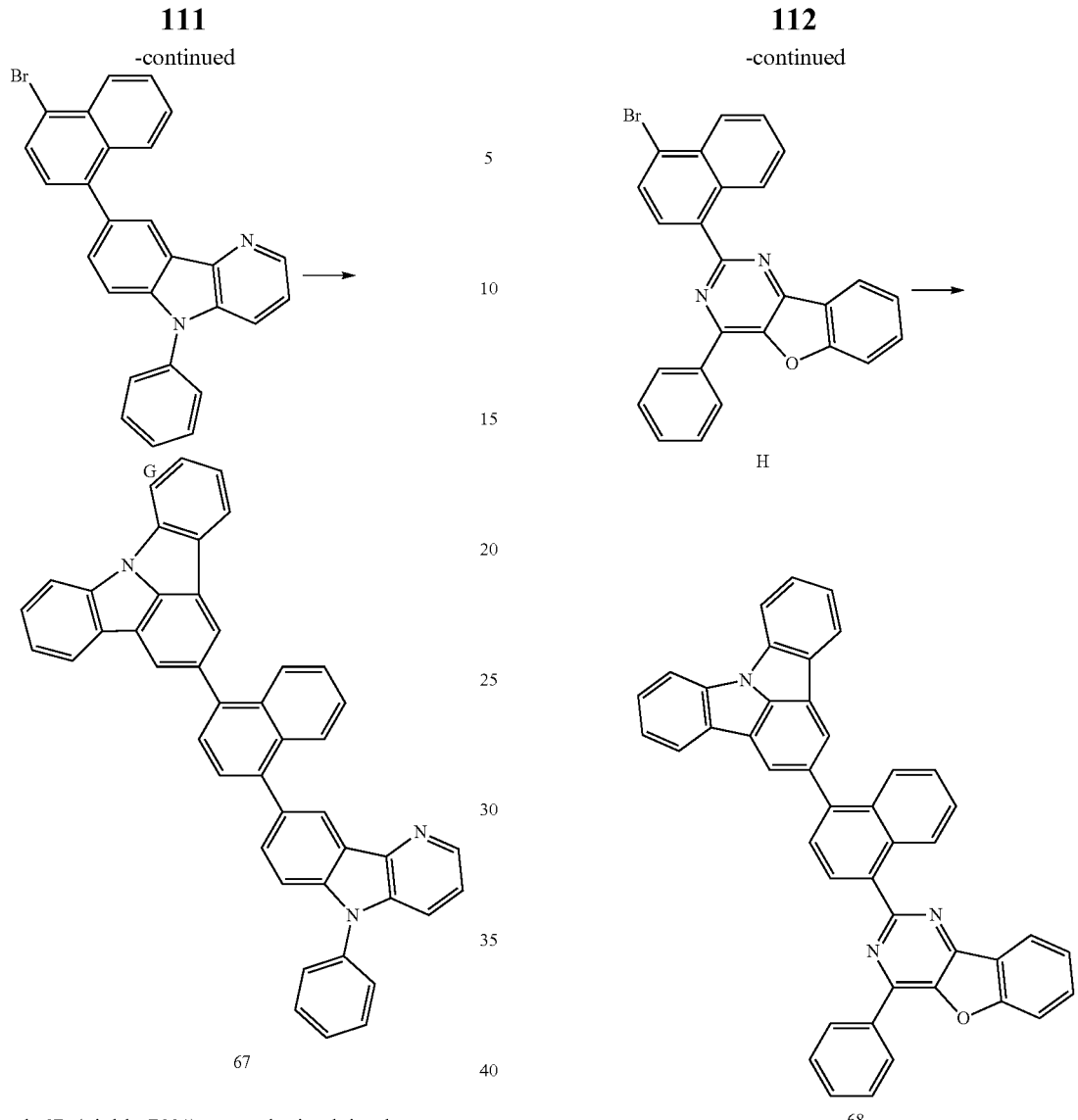

Compound 67 (yield: 70%) was obtained in the same manner as in Synthesis Example 1 except that Intermediate G was used instead of Intermediate A in synthesizing Compound 2. The compound thus obtained was confirmed by using LC-MS and NMR.

$C_{45}H_{27}N_3$: M+ 609.22

$^1$H NMR (CDCl$_3$, 300 MHz) δ(ppm) 9.00 (d, 2H), 8.43 (d, 1H), 8.30 (d, 1H), 8.19 (d, 2H), 8.13 (d, 1H), 7.97 (d, 1H), 7.89 (s, 1H), 7.65-7.50 (m, 13H), 7.39 (t, 2H), 7.22-7.20 (m, 3H)

Synthesis Example 8: Synthesis of Compound 68

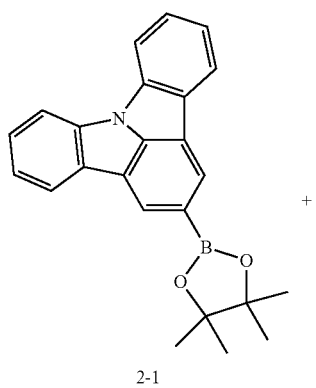

Compound 68 (yield: 61%) was obtained in the same manner as in Synthesis Example 1 except that Intermediate H was used instead of Intermediate A in synthesizing Compound 2. The compound thus obtained was confirmed by using LC-MS and NMR.

$C_{44}H_{25}N_3O$: M+ 611.20

$^1$H NMR (CDCl$_3$, 300 MHz) δ(ppm) 9.02 (d, 2H), 8.95 (d, 1H), 8.30 (d, 1H), 8.19 (d, 2H), 8.06 (d, 1H), 7.86-7.84 (m, 3H), 7.70-7.49 (m, 14H), 7.97 (d, 1H), 7.89 (s, 1H), 7.65-7.50 (m, 14H), 7.22-7.20 (m, 3H)

Evaluation Example 1: Evaluation on HOMO, LUMO, and Triplets (T1) Energy Levels

HOMO, LUMO, and T1 energy levels of Compounds 2, 5, 54 to 68, A, B, C, and D were evaluated according to the method indicated in Table 2, and results thereof are shown in Table 3.

TABLE 2

| | |
|---|---|
| HOMO energy level evaluation method | A potential (Volts, V) - current (Amperes, A) graph of each compound was obtained by using cyclic voltammetry (CV) (electrolyte: 0.1 molar (M) Bu$_4$NClO$_4$/solvent: 2-MeTHF/electrode: 3 electrode system (working electrode: GC, reference electrode: Ag/AgCl, auxiliary electrode: Pt)). Subsequently, from reduction onset of the graph, a HOMO energy level of the compound was calculated. |
| LUMO energy level evaluation method | Each compound was diluted at a concentration of $1 \times 10^{-5}$ M in 2-methyltetrahydrofuran (2-MeTHF), and an UV absorption spectrum thereof was measured at room temperature by using a Shimadzu UV-350 spectrometer. A LUMO energy level thereof was calculated by using an optical band gap (Eg) from an edge of the absorption spectrum. |
| T1 energy level evaluation method | A mixture (each compound was dissolved in an amount of 1 milligram (mg) in 3 cubic centimeters (cc) of 2-MeTHF) of 2-MeTHF and each compound was loaded into a quartz cell. Subsequently, the resultant quartz cell was loaded into liquid nitrogen (77 Kelvins (K)) and a photoluminescence spectrum thereof was measured by using a device for measuring photoluminescence. The obtained spectrum was compared with a photoluminescence spectrum measured at room temperature, and peaks observed only at a low temperature were analyzed to calculate T1 energy levels. |

TABLE 3

| Compound No. | HOMO (eV) (calc.) | LUMO (eV) (calc.) | T1 energy level (eV) |
|---|---|---|---|
| Compound 2 | −5.652 | −2.203 | 2.441 |
| Compound 5 | −5.561 | −1.983 | 2.591 |
| Compound 54 | −5.596 | −1.972 | 2.770 |
| Compound 68 | −5.602 | −2.054 | 2.413 |
| Compound A | −5.985 | −1.975 | 2.911 |
| Compound B | −5.874 | −2.512 | 2.142 |
| Compound C | −5.712 | −1.554 | 2.971 |
| Compound D | −5.623 | −1.502 | 2.892 |

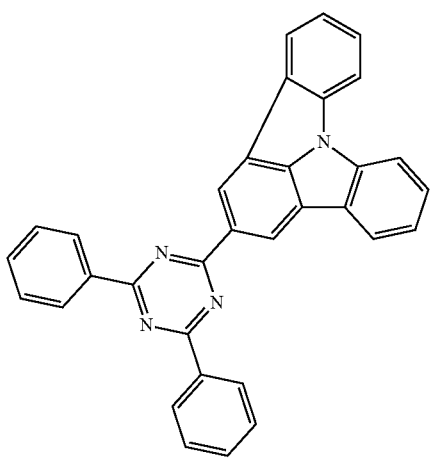

A

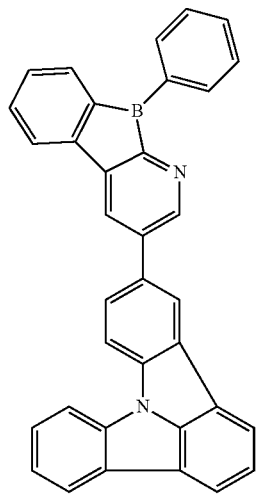

B

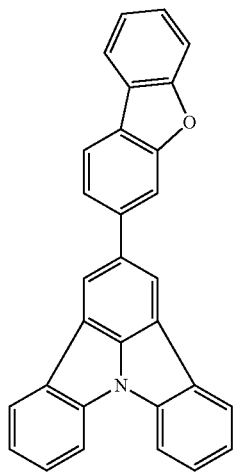

C

-continued

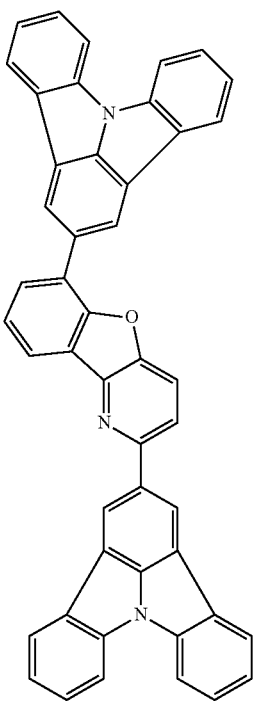

From Table 3, it is confirmed that the compounds prepared in Synthesis Examples have electric characteristics that are suitable for use as a material for forming an organic light-emitting device.

Example 1

A glass substrate, on which an anode having a structure of ITO/Ag/ITO (70/1,000/70 Å) was formed, was cut to a size of 50 millimeters (mm)×50 mm×0.7 mm, sonicated in isopropyl alcohol, acetone, and pure water, in each solvent for 5 minutes, and cleaned by the exposure to ultraviolet rays for 30 minutes, and ozone. The glass substrate was mounted on a vacuum-deposition apparatus.

2-TNATA was vacuum-deposited on the anode of the glass substrate to form a hole injection layer having a thickness of 600 Angstroms (Å). Subsequently, 4,4'-Bis[N-(1-naphthyl)-N-phenylamino]biphenyl (NPB) was vacuum-deposited on the hole injection layer to form a hole transport layer having a thickness of 1,000 Å, thereby forming a hole transport region.

Thereafter, Compound 54 (a host) and $Ir(ppy)_3$ (a dopant) (referred to as Compound PD1 herein) were co-deposited at a weight ratio of 91:9 on the hole transport layer to form an emission layer having a thickness of 250 Å.

BCP was vacuum-deposited on the emission layer to form a hole blocking layer having a thickness of 50 Å. $Alq_3$ was vacuum-deposited on the hole blocking layer to form an electron transport layer having a thickness of 350 Å. LiF was vacuum-deposited on the electron transport layer to form an electron injection layer having a thickness of 10 Å, thereby forming an electron transport region.

Mg and Ag were vacuum-deposited on the electron injection layer at a weight ratio of 90:10 to form a cathode having a thickness of 120 Å, thereby completing manufacture of an organic light-emitting device.

Examples 2 to 5 and Comparative Examples 1 to 4

Organic light-emitting devices were manufactured according to Examples 2 to 5 and Comparative Examples 1 to 4 as in Example 1, except that a thickness of the hole transport layer was different for each Example according to Table 4. As a host and a dopant in forming an emission layer, hosts and dopants listed in Table 4 were used for each Example.

Evaluation Example 2: Evaluation of Characteristics of Organic Light-Emitting Device A driving voltage, current density, luminance, efficiency, emission color, and lifespan of the organic light-emitting devices manufactured according to Examples 1 to 5 and Comparative Examples 1 to 4 were measured by using Kethley SMU 236 and luminance meter PR650, and results thereof are shown in Table 4. $T_{97}$ lifespan in Table 4 indicates a period of time (hr) taken for the luminance to reach 97% with respect to 100% of an initial luminance of 500 nit.

TABLE 4

|  | Thickness of Hole Transport Layer (Å) | EML Host | Dopant | Driving Voltage (V) | Current Density (mA/cm$^2$) | Luminance (cd/m$^2$) | Efficiency (cd/A) | Emission color | LT$_{97}$ (hr) |
|---|---|---|---|---|---|---|---|---|---|
| Example 1 | 1,000 | Compound 54 | Ir(ppy)$_3$ | 5.4 | 10 | 6,781 | 68.4 | Green | 76 |
| Example 2 | 1,000 | Compound 65 | Ir(ppy)$_3$ | 5.8 | 10 | 6,354 | 65.7 | Green | 74 |
| Example 3 | 1,350 | Compound 2 | PtOEP | 5.8 | 10 | 3,754 | 35.1 | Red | 116 |
| Example 4 | 1,350 | Compound 5 | PtOEP | 6.0 | 10 | 3,121 | 32.2 | Red | 110 |
| Example 5 | 1,350 | Compound 67 | PtOEP | 5.6 | 10 | 3,654 | 38.1 | Red | 114 |
| Comparative Example 1 | 1,000 | Compound A | Ir(ppy)$_3$ | 8.5 | 10 | 4,231 | 47.2 | Green | 37 |
| Comparative Example 2 | 1,000 | Compound C | Ir(ppy)$_3$ | 7.0 | 10 | 4,712 | 40.1 | Green | 32 |
| Comparative Example 3 | 1,000 | Compound D | Ir(ppy)$_3$ | 7.7 | 10 | 4,552 | 45.0 | Green | 35 |
| Comparative Example 4 | 1,350 | Compound B | PtOEP | 8.2 | 10 | 1,786 | 20.1 | Red | 51 |

2
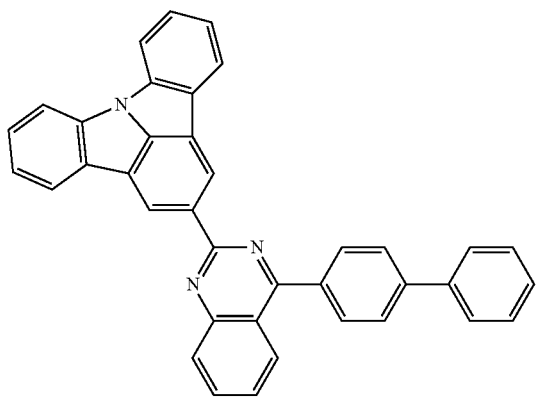
5
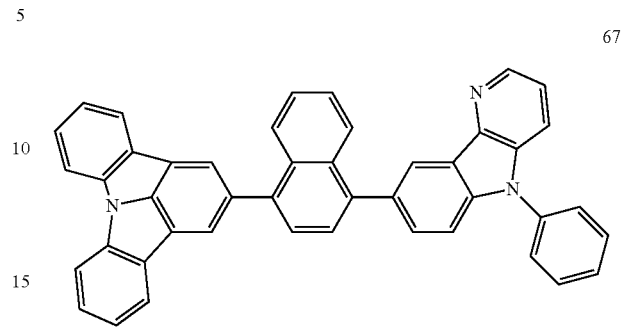
5
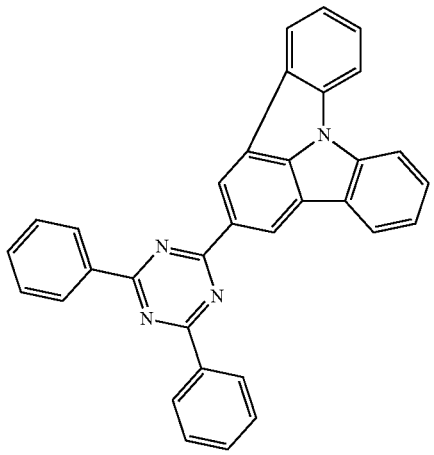
54
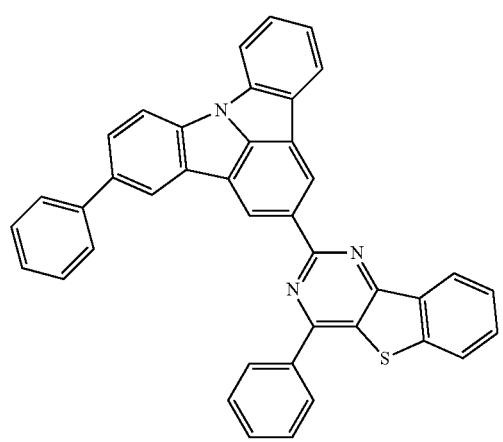
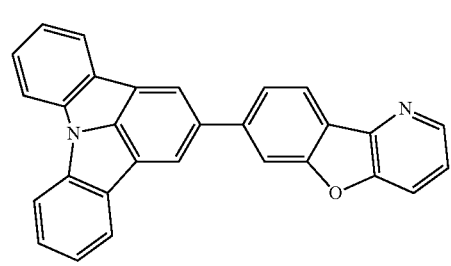
67
A
B
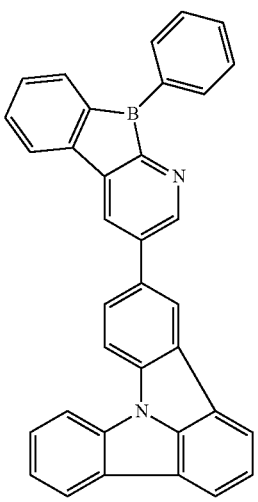

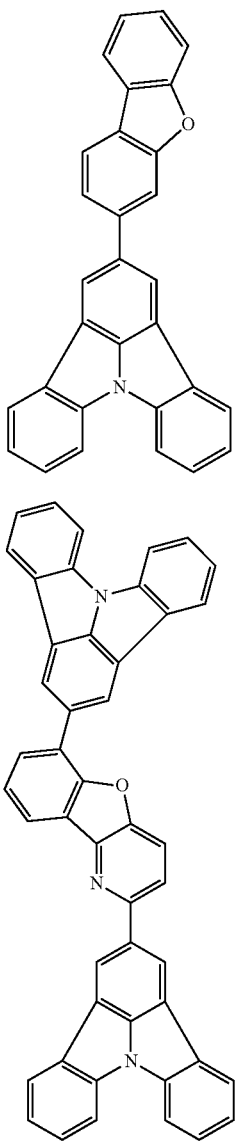

Referring to Table 4, it is confirmed that the organic light-emitting devices according to Examples 1 and 2 have a low driving voltage, high efficiency, and long lifespan compared to the organic light-emitting devices according to Comparative Examples 1 to 3, and the organic light-emitting devices according to Examples 3 and 4 have a low driving voltage, high efficiency, and long lifespan compared to the organic light-emitting devices according to Comparative Example 4.

As described above, according to the one or more of the above exemplary embodiments, the condensed cyclic compound according to embodiments has excellent electric characteristics and thermal stability. Accordingly, an organic light-emitting device including the condensed cyclic compound may have a low driving voltage, high efficiency, high luminance, and long lifespan.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the FIGURES, it will be understood by those of ordinary skill in the art that various changes in form and details may be made therein without departing from the spirit and scope as defined by the following claims.

What is claimed is:

1. A condensed cyclic compound represented by Formula 1A:

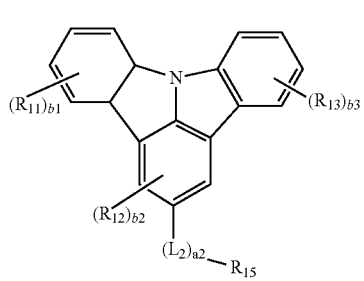

Formula 1A wherein in Formula 1A, $L_2$ is a phenylene or a naphthylene group, each optionally substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cyclopentenyl group, a cyclohexenyl group, a cycloheptenyl group, a phenyl group, a naphthyl group, $Si(Q_{23})(Q_{24})(Q_{25})$, or any combination thereof, wherein $Q_{23}$ to $Q_{25}$ are each independently a hydrogen, a $C_1$-$C_{20}$ alkyl group, a $C_1$-$C_{20}$ alkoxy group, a phenyl group, or a naphthyl group, a2 is 1 or 2, provided that when $R_{15}$ is of Formulae 2-89, 2-91, 2-93, 2-96 or 2-98, then a2 is 0, $R_{11}$ to $R_{13}$ are each independently a hydrogen, a deuterium, F, Cl, Br, I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a $C_1$-$C_{20}$ alkyl group, or a $C_1$-$C_{20}$ alkoxy group;

wherein $R_{15}$ is a group represented by one of Formulae 2-1, 2-7, 2-19, 2-89, 2-91, 2-93, 2-96, and 2-98,

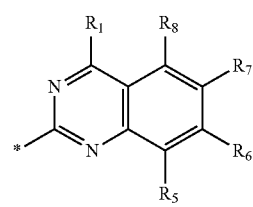

Formula 2-1

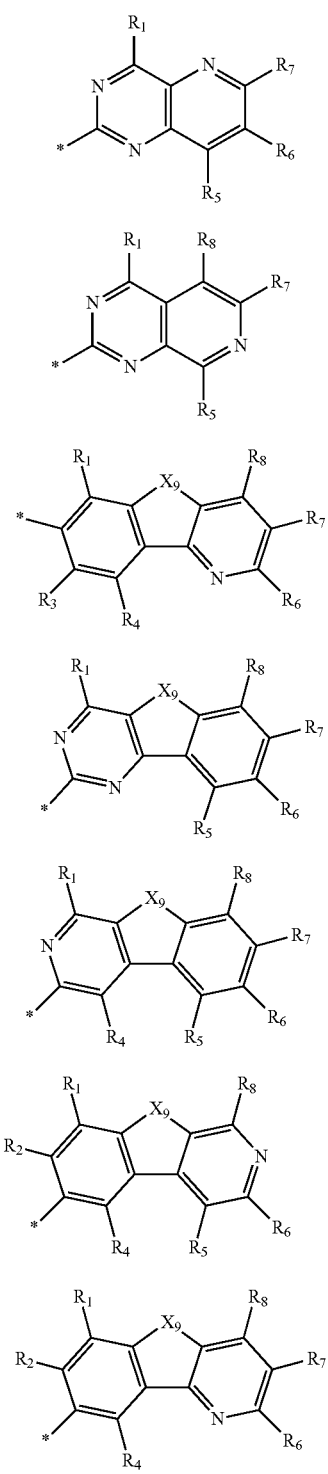

wherein in Formulae 2-1, 2-7, 2-19, 2-89, 2-91, 2-93, 2-96, and 2-98, $X_9$ is O, S, or N($R_9$), $R_1$ to $R_8$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, phenyl, biphenyl, terphenyl, a $C_1$-$C_{20}$ alkyl group, or a $C_1$-$C_{20}$ alkoxy group;

wherein $R_9$ is a phenyl or a naphthyl group, each optionally substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C1-$C_{20}$ alkyl group, a C1-$C_{20}$ alkoxy group, a cyclopentyl group, a cyclohexyl group, a cyclopentenyl group, a cyclohexenyl group, a cycloheptenyl group, a phenyl group, a naphthyl group, or any combination thereof;

b1 and b3 are each independently an integer selected from 1 to 4, b2 is an integer selected from 0 to 3.

2. The condensed cyclic compound of claim 1, wherein when present, $L_2$ is a phenylene group or a naphthylene group, each optionally substituted with at least one of deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, —Si($Q_{23}$)($Q_{24}$)($Q_{25}$), or any combination thereof;

wherein $Q_{23}$ to $Q_{25}$ are each independently a hydrogen, a $C_1$-$C_{10}$ alkyl group, a $C_1$-$C_{10}$ alkoxy group, a phenyl group, a naphthyl group, or any combination thereof.

3. The condensed cyclic compound of claim 1, wherein the $R_{15}$ is a group represented by one of Formulae 3-1 to 3-5, 3-13 to 3-21, 3-24 to 3-25, 3-34 to 3-35, and 3-38 to 3-39:

Formula 3-1

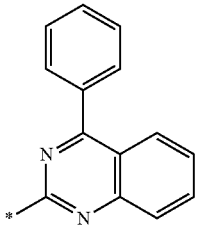

Formula 3-2

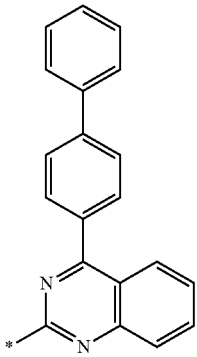

Formula 3-3
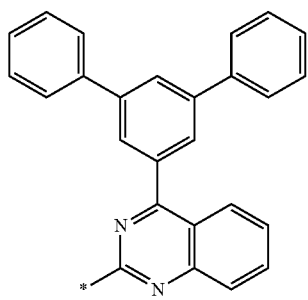
Formula 3-4
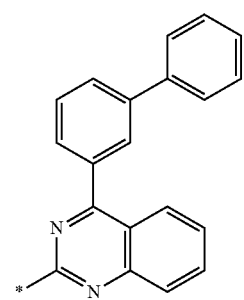
Formula 3-5
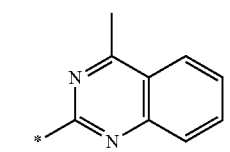
Formula 3-13
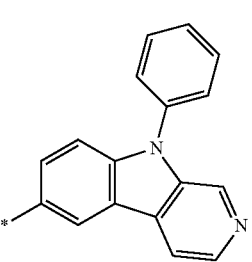
Formula 3-14
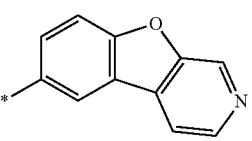
Formula 3-15
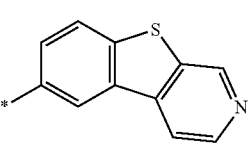
Formula 3-16
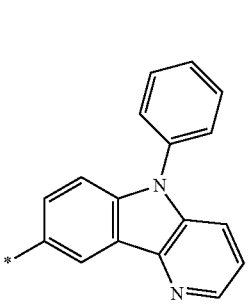
Formula 3-17
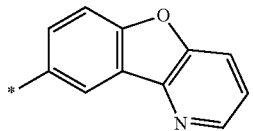
Formula 3-18
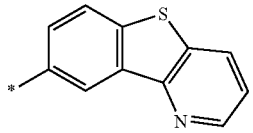
Formula 3-19
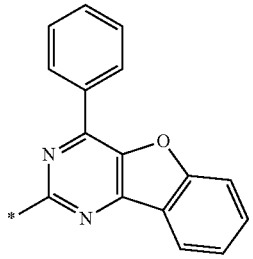
Formula 3-20
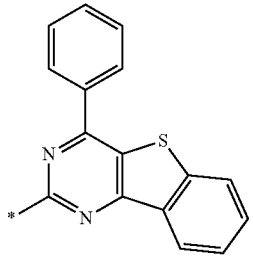
Formula 3-21
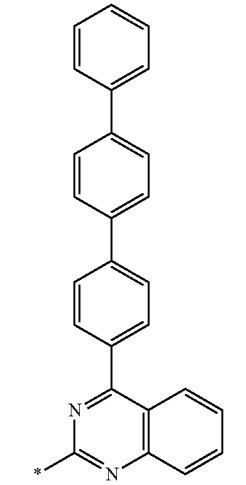
Formula 3-24
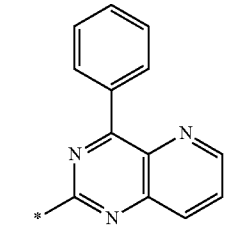

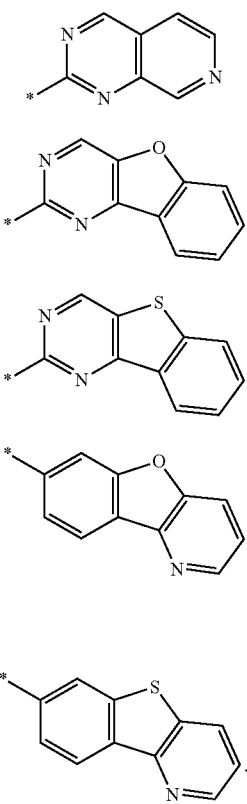

Formula 3-25

Formula 3-34

Formula 3-35

Formula 3-38

Formula 3-39

4. The condensed cyclic compound of claim 1, wherein the condensed cyclic compound is represented by one of Formulae 1-1, 1-3, and 1-4:

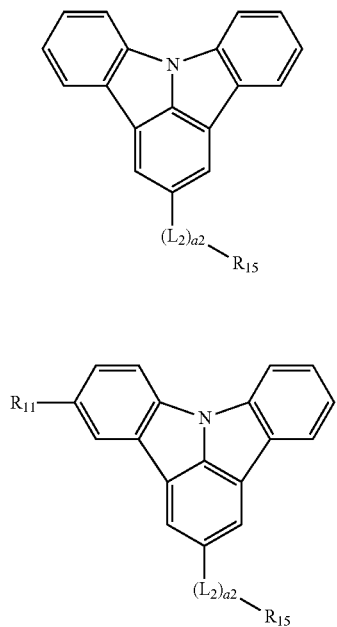

Formula 1-1

Formula 1-3

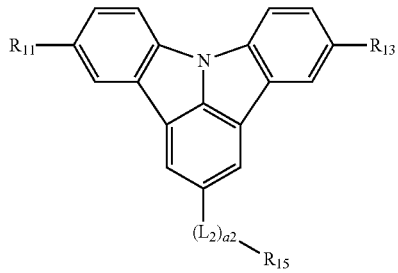

Formula 1-4 wherein in the Formulae 1-1, 1-3, and 1-4,
the descriptions for $L_2$, a2, $R_{11}$, $R_{13}$, and $R_{15}$ are the same as in claim 1.

5. An organic light-emitting device comprising:
a first electrode;
a second electrode; and
an organic layer disposed between the first electrode and the second electrode,
wherein the organic layer comprises an emission layer and at least one condensed cyclic compound represented by Formula 1 of claim 1.

6. The organic light-emitting device of claim 5, wherein the emission layer comprises the at least one condensed cyclic compound of claim 1.

7. The organic light-emitting device of claim 6, wherein the first electrode is an anode,
the second electrode is a cathode,
and the organic layer comprises:
i) a hole transport region disposed between the first electrode and the emission layer, wherein the hole transport region comprises at least one selected from the group consisting of a hole injection layer, a hole transport layer, and an electron blocking layer, and
ii) an electron transport region disposed between the emission layer and the second electrode, wherein the electron transport region comprises at least one selected from the group consisting of a hole blocking layer, an electron transport layer, and an electron injection layer.

8. The organic light-emitting device of claim 6, wherein the emission layer further comprises a phosphorescent dopant, and wherein an amount of the at least one condensed cyclic compound of claim 1 in the emission layer is greater than an amount of the phosphorescent dopant.

9. A condensed cyclic compound selected from the group consisting of:

1

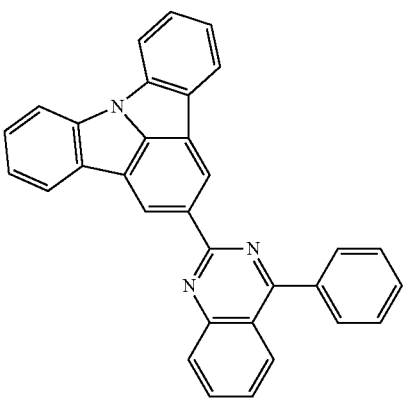

127
-continued
2
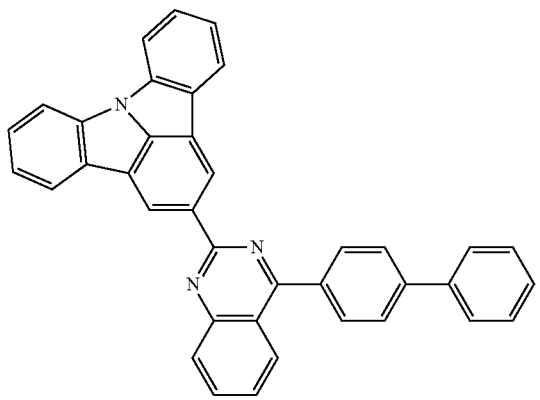
5
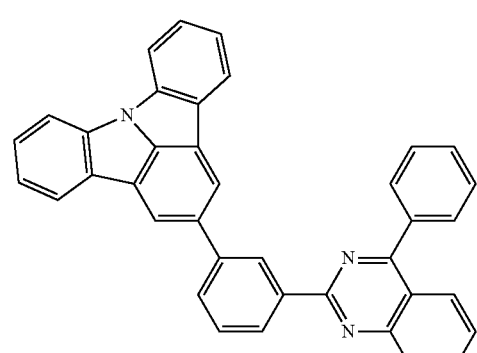
6
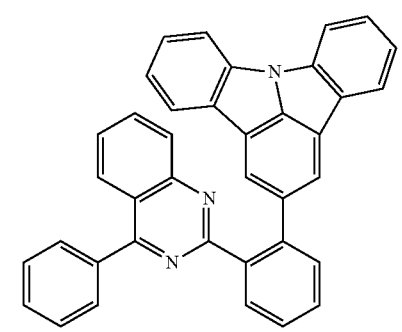
7
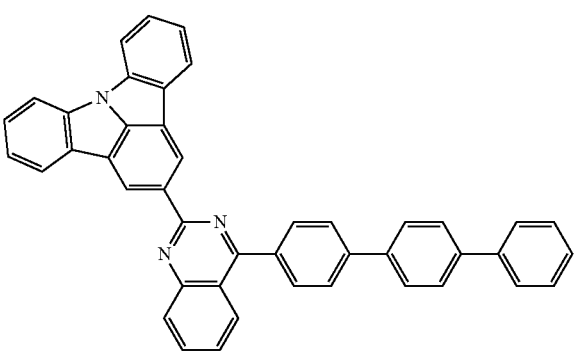
128
-continued
9
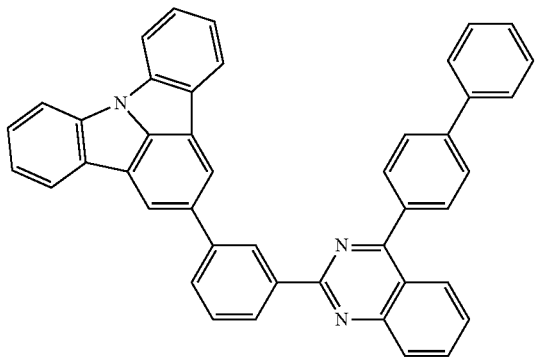
10
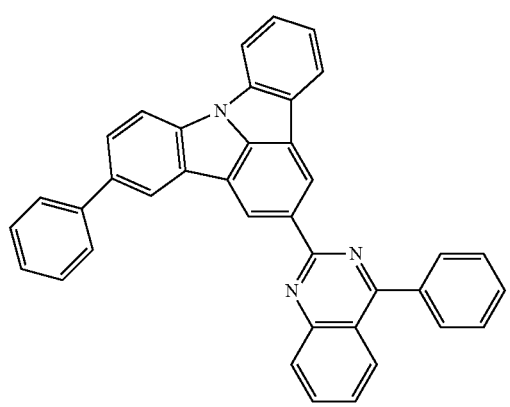
22
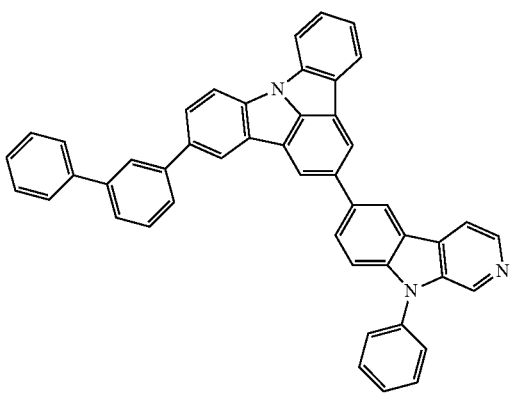

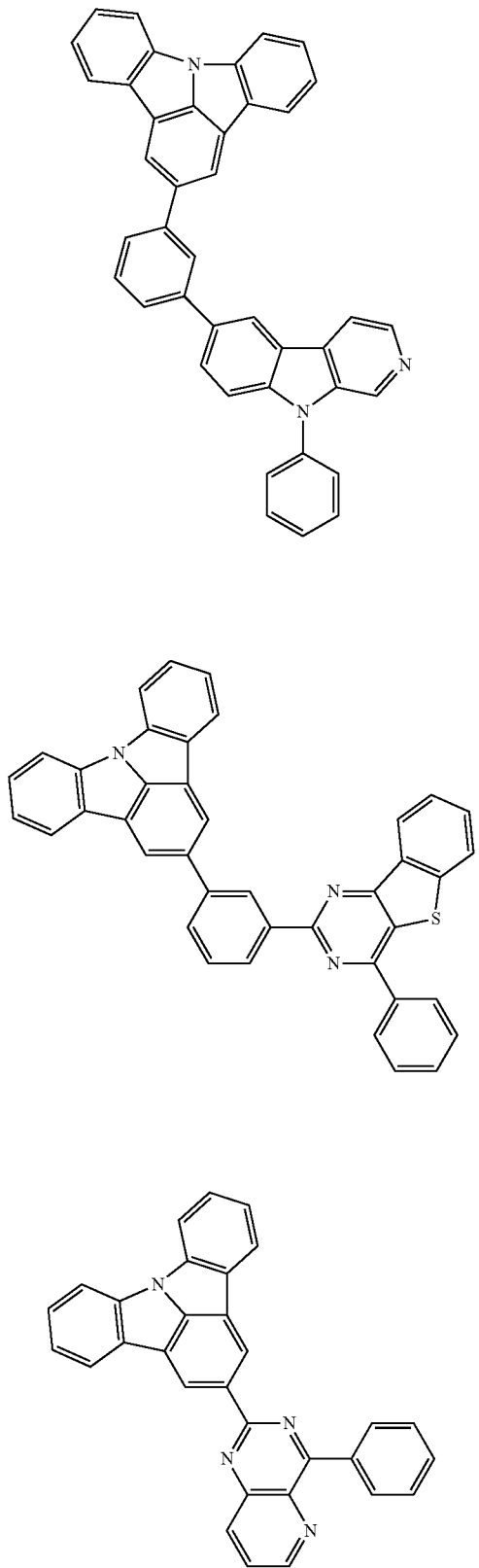
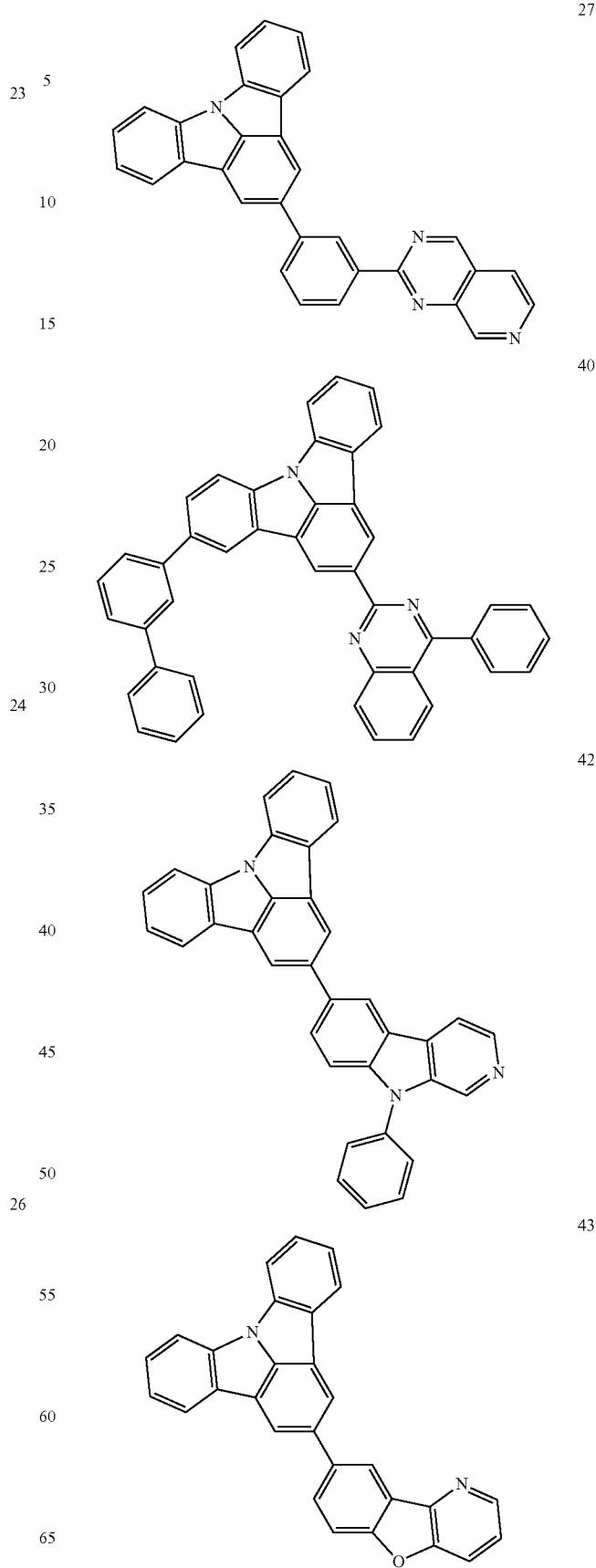

44
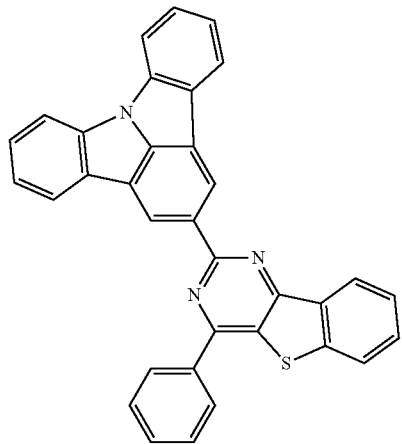
49
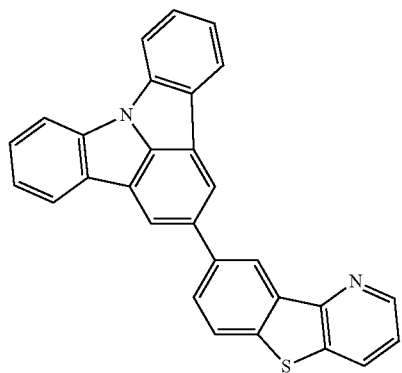
50
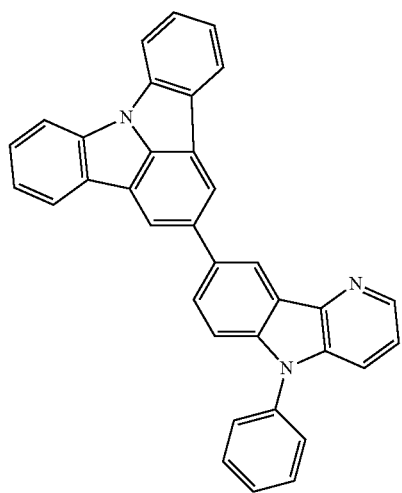
51
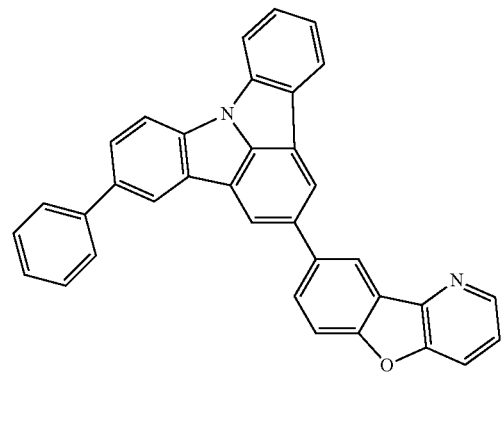
53
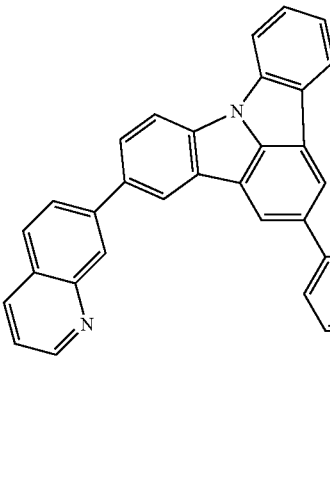
54
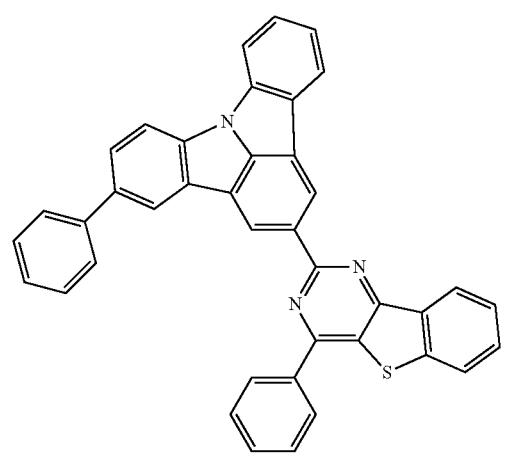

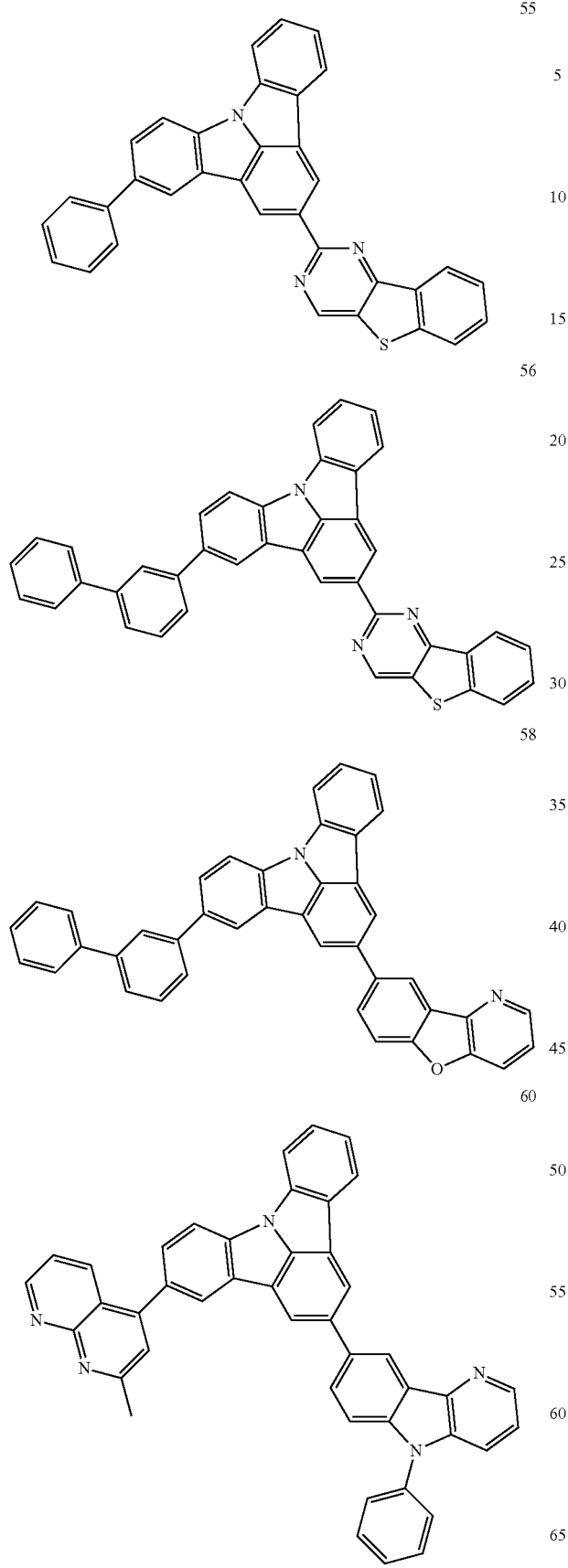
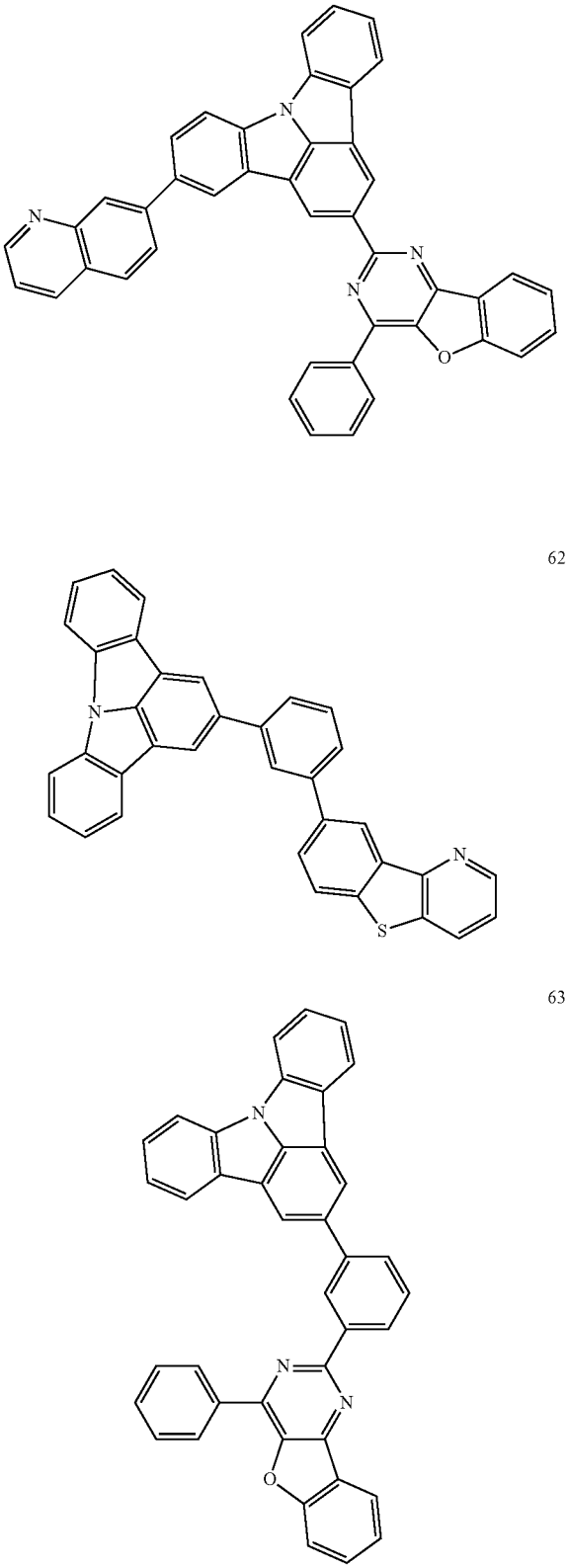

64
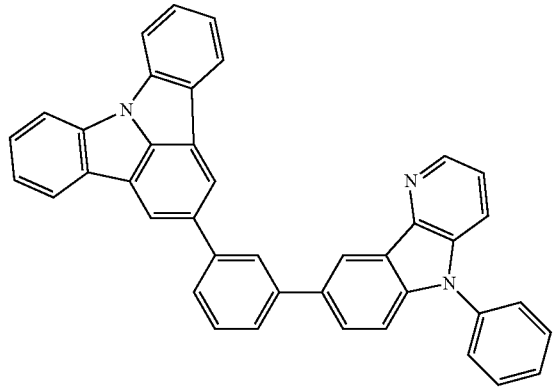
65
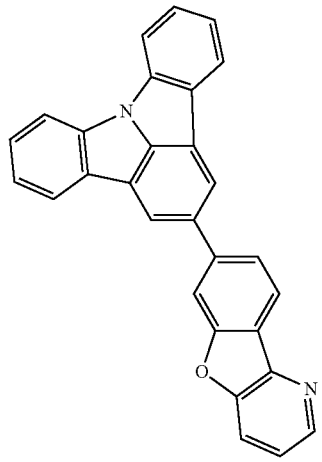
67
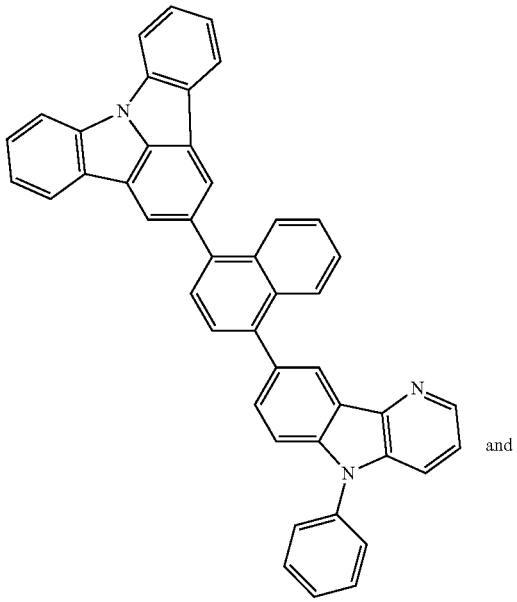
and
68
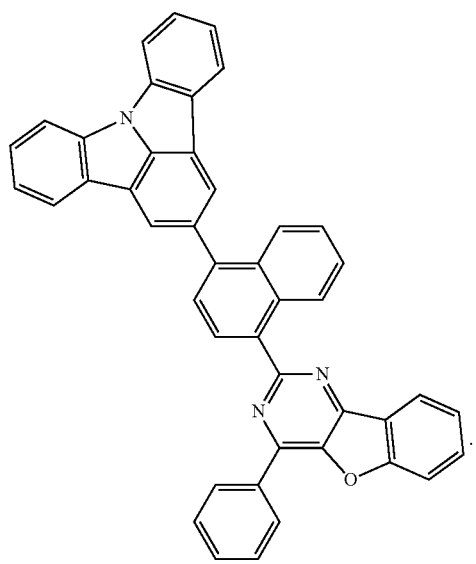
.
* * * * *